(12) United States Patent
Šarlija et al.

(10) Patent No.: US 12,053,288 B2
(45) Date of Patent: Aug. 6, 2024

(54) SENSING SYSTEM WITH FEATURES FOR DETERMINING AND PREDICTING BRAIN AGE AND OTHER ELECTROPHYSIOLOGICAL METRICS OF A SUBJECT

(71) Applicant: NeuroGeneces Inc., Santa Fe, NM (US)

(72) Inventors: Marko Šarlija, Zagreb (HR); Michael Kenneth Comerford, III, Santa Fe, NM (US); Karen Crow, Santa Fe, NM (US)

(73) Assignee: NeuroGeneces Inc., Santa Fe, NM (US)

( * ) Notice: Subject to any disclaimer, the term of this patent is extended or adjusted under 35 U.S.C. 154(b) by 0 days.

(21) Appl. No.: 18/137,250

(22) Filed: Apr. 20, 2023

(65) Prior Publication Data
US 2023/0337961 A1   Oct. 26, 2023

Related U.S. Application Data

(60) Provisional application No. 63/402,756, filed on Aug. 31, 2022, provisional application No. 63/333,832, filed on Apr. 22, 2022.

(51) Int. Cl.
*A61B 5/377* (2021.01)
*A61B 5/00* (2006.01)
(Continued)

(52) U.S. Cl.
CPC .......... *A61B 5/377* (2021.01); *A61B 5/0205* (2013.01); *A61B 5/4812* (2013.01); *A61B 5/725* (2013.01);
(Continued)

(58) Field of Classification Search
CPC ..... A61B 5/377; A61B 5/0205; A61B 5/4812; A61B 5/725; A61B 5/7267; A61B 5/7275;
(Continued)

(56) References Cited

U.S. PATENT DOCUMENTS

| | | |
|---|---|---|
| 7,486,993 B2 | 2/2009 | Gilmer et al. |
| 2010/0094155 A1 | 4/2010 | Prichep |

(Continued)

FOREIGN PATENT DOCUMENTS

| | | | | |
|---|---|---|---|---|
| CN | 106127769 | 11/2016 | | |
| KR | 102336111 B1 * | 12/2021 | ............. | A61B 5/372 |

(Continued)

OTHER PUBLICATIONS

Martínez-Martínez et al., "Regularized extreme learning machine for regression problems", Neurocomputing, 74, 3716-3721, published Jul. 23, 2011 (Year: 2011).*

(Continued)

*Primary Examiner* — Matthew Kremer
*Assistant Examiner* — Jonathan Drew Moroneso
(74) *Attorney, Agent, or Firm* — Fish & Richardson P.C.

(57) ABSTRACT

Some systems, devices and methods detailed herein provide a system for use in determining metrics of a subject. The system can provide, as an output, a function-metric value determined based on a defined relationship between physiological measures and a chronological age.

19 Claims, 17 Drawing Sheets

(51) Int. Cl.
  *A61B 5/0205* (2006.01)
  *A61B 5/024* (2006.01)
  *A61B 5/291* (2021.01)
  *A61B 5/31* (2021.01)
  *A61B 5/369* (2021.01)
  *A61B 5/374* (2021.01)
  *A61B 5/384* (2021.01)
  *G06F 3/01* (2006.01)
  *G06N 3/02* (2006.01)
  *G06N 3/06* (2006.01)
  *G06N 3/08* (2023.01)
  *G16H 50/70* (2018.01)

(52) U.S. Cl.
  CPC .......... *A61B 5/7267* (2013.01); *A61B 5/7275* (2013.01); *A61B 5/02416* (2013.01); *A61B 5/291* (2021.01); *A61B 5/31* (2021.01); *A61B 5/369* (2021.01); *A61B 5/374* (2021.01); *A61B 5/384* (2021.01); *A61B 5/4806* (2013.01); *A61B 5/4809* (2013.01); *A61B 5/4815* (2013.01); *A61B 5/72* (2013.01); *A61B 5/7235* (2013.01); *G06F 3/015* (2013.01); *G06N 3/02* (2013.01); *G06N 3/06* (2013.01); *G06N 3/08* (2013.01); *G16H 50/70* (2018.01)

(58) Field of Classification Search
  CPC ....... A61B 5/02416; A61B 5/291; A61B 5/31; A61B 5/374; A61B 5/384; A61B 5/4809; A61B 5/4815; A61B 5/72; A61B 5/7235; A61B 5/369; A61B 5/4806; A61B 5/015; A61B 5/38; A61B 5/383; A61B 5/6814; A61B 5/6843; A61B 2562/0219; A61B 5/378; A61B 5/4064; A61B 5/4088; A61B 5/4818; A61B 5/6803; A61B 5/4842; G06F 3/015; G06N 3/02; G06N 3/06; G06N 3/08; G06N 3/0985; G06N 5/01; G06N 7/01; G06N 20/10; G16H 50/70; G16H 10/60; G16H 50/20; A61N 1/0529; H04R 1/105; H04R 2460/13

See application file for complete search history.

(56) References Cited

U.S. PATENT DOCUMENTS

| | | | |
|---|---|---|---|
| 2014/0289172 A1* | 9/2014 | Rothman | A61B 5/369 706/11 |
| 2019/0099582 A1* | 4/2019 | Crow | A61B 5/375 |
| 2019/0192069 A1* | 6/2019 | Garcia Molina | A61B 5/4812 |
| 2019/0274632 A1* | 9/2019 | Kochura | G06N 20/00 |
| 2020/0101262 A1* | 4/2020 | Garcia Molina | A61B 5/1495 |
| 2020/0105398 A1* | 4/2020 | Chen | G06F 3/015 |
| 2020/0155020 A1 | 5/2020 | Alberts et al. | |
| 2020/0337625 A1 | 10/2020 | Aimone et al. | |
| 2020/0337645 A1* | 10/2020 | Kremen | A61B 5/316 |
| 2021/0045676 A1* | 2/2021 | Lee | A61B 5/4815 |
| 2021/0169417 A1 | 6/2021 | Burton et al. | |
| 2021/0216826 A1* | 7/2021 | Hsieh | A61B 5/055 |
| 2021/0296001 A1* | 9/2021 | Aoyama | A61B 5/291 |
| 2022/0167908 A1* | 6/2022 | D'Arcy | A61B 5/398 |
| 2022/0192556 A1* | 6/2022 | Sankar | A61B 5/1118 |
| 2022/0225920 A1* | 7/2022 | Read | A61N 1/36082 |
| 2022/0314002 A1* | 10/2022 | Arcot Desai | G16H 50/20 |
| 2022/0344018 A1* | 10/2022 | Goldstein | G16H 50/30 |
| 2022/0361788 A1* | 11/2022 | Shah | G16H 50/20 |
| 2023/0000424 A1* | 1/2023 | Tseng | G06T 7/0016 |
| 2023/0065543 A1* | 3/2023 | Plath | G16H 50/50 |
| 2023/0169648 A1* | 6/2023 | Kasai | A61B 5/4088 382/128 |
| 2023/0200697 A1* | 6/2023 | Kuan | G16H 50/20 706/25 |

FOREIGN PATENT DOCUMENTS

| | | | |
|---|---|---|---|
| WO | WO 2014172775 | 10/2014 | |
| WO | WO 2015186963 | 12/2015 | |
| WO | WO 2016205811 | 12/2016 | |
| WO | WO 2017212333 | 12/2017 | |
| WO | WO 2019070939 | 4/2019 | |
| WO | WO-2019166859 A1 * | 9/2019 | |
| WO | WO-2020085553 A1 * | 4/2020 | ........... A61B 5/0482 |
| WO | WO 2021255710 | 12/2021 | |

OTHER PUBLICATIONS

Of Shahriari et al., "Taking the Human Out of the Loop: A Review of Bayesian Optimization", Proceedings of the IEEE, 4, 148-175, published Dec. 10, 2015 (Year: 2015).*

Kang et al., Korean Patent Document KR 102336111 B1, translation provided by Clarivate Analytics (Year: 2021).*

Lee et al., WIPO Publication 2020/085553 A1, translation provided by Clarivate Analytics (Year: 2020).*

Brink-Kjaer et al., "Predicting age with deep neural networks from polysomnogram," 2020 42nd Annual International Conference of the IEEE Engineering in Medicine & Biology Society (EMBC), Jul. 20, 2020, 146-149.

Nygate et al., "EEG-Based Deep Neural Network Model for Brain Age Prediction and Its Association with Patient Health Conditions," Sleep, May 2021, 44(Supplement, 543):A214.

Ouyang et al., "Effects of Aerobic Exercise on Brain Age and Health in Older Adults: A Single-Arm Clinical Trial," medRxiv., Jun. 2022, 33 pages.

Sun et al., "Brain age from the electroencephalogram of sleep," Neurobiology of Aging, Feb. 1, 2019, 74:112-120.

Yook et al., "Predicting brain age based on sleep EEG and DenseNet," 2021 43rd Annual International Conference of the IEEE Engineering in Medicine & Biology Society (EMBC), Nov. 1, 2021, 245-248.

International Search Report and Written Opinion in International Appln. No. PCT/US2023/019286, dated Jul. 28, 2023, 15 pages.

AARP.org [online], "Brain Health and Dietary Supplements: Where's the Evidence? 2019 AARP Brain Health and Dietary Supplements Survey," Aug. 14, 2019, retrieved on Apr. 29, 2024, retrieved from URL: <https://www.aarp.org/pri/topics/health/prevention-wellness/brain-health-and-dietary-supplements-survey.html>, 5 pages.

AARP.org [online], "The Real Deal on Brain Health Supplements: GCBH Recommendations on Vitamins, Minerals, and Other Dietary Supplements," Global Council on Brain Health, 2019, retrieved on Apr. 29, 2024, retrieved from URL: <https://www.aarp.org/content/dam/aarp/health/brain_health/2019/06/gcbh-supplements-report-english.doi.10.26419-2Fpia.00094.001.pdf>, 31 pages.

AICPA.org [online], "CPA Exam Pass Rates," American Institute of Certified Public Accountants (AICPA), 2020, retrieved on Apr. 29, 2024, retrieved from URL: <https://web.archive.org/web/20210514075642/https://www.aicpa.org/becomeacpa/cpaexam/psychometricsandscoring/passingrates.Htm>, 1 page.

Alliedmarketresearch.com [online], "Cognitive and Memory Enhancer Drugs Market by Product (Aricept, Razadyne, Namenda, Exelon, Provigil, Ritalin, and Adderall) and Application (Disease Treatment, Academic Performance, and Athletic Performance)—Global Opportunity Analysis and Industry Forecast, 2017-2023," Allied Market Research, Feb. 2018, retrieved on May 8, 2024, retrieved from URL: <https://web.archive.org/web/20191022060835/https://www.alliedmarketresearch.co m/cognitive-and-memory-enhancer-drugs-market>, 26 pages.

Alzint.org [online], "Dementia statistics," Alzheimer's Disease International, 2020, retrieved on Apr. 29, 2024, retrieved from URL: <https://www.alzint.org/abouUdementia-facts-figures/dementia-statistics/>, 4 pages.

Bellesi et al., "Enhancement of sleep slow waves: underlying mechanisms and practical consequences," Front Syst Neurosci., Oct. 28, 2014, 8(208):1-17.

Buzsaki et al., "Neuronal Oscillations in Cortical Networks," Science, Jun. 25, 2004, 304(5679):1926-1929.

(56) References Cited

OTHER PUBLICATIONS

Casal et al., "Sleep-wake stages classification using heart rate signals from pulse oximetry," Heliyon, Oct. 2019, 5(10):e02529, 12 pages.

Center4Research.org [online], ""Study Drug" Abuse by College Students: What You Need to Know," National Center for Health Research, 2021, retrieved on Apr. 30, 2024, retrieved from URL: <https://www.center4research.org/study-drug-abuse-college-students/>, 6 pages.

Chauvette et al., "Sleep Oscillations in the Thalamocortical System Induce Long-Term Neuronal Plasticity," Neuron., Sep. 20, 2012, 75(6):1105-1113.

Clemow et al., "The potential for misuse and abuse of medications in ADHD: A review," Postgrad Med., Sep. 2014, 126(5):64-81. doi:10.3810/pgm.2014.09.2801.

Coates et al., "Owning Ethical Innovation: Claims about Commercial Wearable Brain Technologies," Neuron., May 22, 2019, 102(4):728-731.

Coma-Del-Corral et al., "Reliability of Telemedicine in the Diagnosis and Treatment of Sleep Apnea Syndrome," Telemedicine and e-Health, Jan. 2013, 19(1):7-12.

d'Angelo et al., "Lifestyle use of drugs by healthy people for enhancing cognition, creativity, motivation and pleasure," British Journal of Pharmacology, Oct. 2017, 174(19):3257-3267.

Danker-Hopfe et al., "Interrater reliability for sleep scoring according to the Rechtschaffen & Kales and the new AASM standard," Journal of Sleep Research, Mar. 2009, 18(1):74-84.

Dehkordi et al., "Sleep Stage Classification in Children Using Photoplethysmogram Pulse Rate Variability," Computing in Cardiology 2014, Cambridge, MA, USA, Sep. 7-10, 2014, pp. 297-300.

Diekelmann et al., "The memory function of sleep," Nature Reviews Neuroscience, Feb. 2010, 11(2):114-126.

Diekelmann et al., "The whats and whens of sleep-dependent memory consolidation," Sleep Medicine Reviews, Oct. 2009, 13(5):309-321.

DNAScience.plos.org [online], "Alzheimer's Treatments in the Pipeline and the False Promise of Prevagen: Distinguishing Hope from Hype," Apr. 1, 2021, retrieved on May 8, 2024, retrieved from URL: <https://dnascience.plos.org/2021/04/01/alzheimers-treatments-in-the-pipeline-and-thefalse-promise-of-prevagen-distinguishing-hope-from-hype/>, 12 pages.

FTC.gov [online], "Lumosity to Pay $2 Million to Settle FTC Deceptive Advertising Charges for Its "Brain Training" Program," Jan. 5, 2016, retrieved on Apr. 30, 2024, retrieved from URL: <https://www.ftc.gov/news-events/news/press-releases/2016/01/lumosity-pay-2-million-settle-ftc-deceptive-advertising-charges-its-brain-training-program>, 3 pages.

Globalnewswire.com [online], "Global Brain Health Supplements Market to Garner $5.81 Billion by 2023 at 8.8% CAGR, Says Allied Market Research," Allied Market Research, Apr. 24, 2019, retrieved on Apr. 29, 2024, retrieved from URL: <https://www.globenewswire.com/news-release/2019/04/24/1808633/0/en/GlobalBrain-Health-Supplements-Market-to-Gamer-5-81-Billion-by-2023-at-8-8-CAGR-SaysAllied-Market-Research.html>, 2 pages.

Grandviewresearch.com [online], "Brain Health Supplements Market Size, Share & Trends Analysis Report By Product (Natural Molecules, Herbal Extract), By Application (Memory Enhancement, Depression & Mood), By Region, And Segment Forecasts, 2021-2028," Grand View Research, Jan. 2021, retrieved on May 8, 2024, retrieved from URL: <https://web.archive.org/web/20210126043111/https://www.grandviewresearch.com/industry-analysis/brain-health-supplements-market>, 13 pages.

Grifantini, "Tracking Sleep to Optimize Health," IEEE Pulse, Oct. 16, 2020, 11(5):12-16.

Haoran et al., "Semi-Supervised End-to-End Automatic Sleep Stage Classification Based on Pseudo-Label," 2021 IEEE international Conference on Power Electronics, Computer Applications (ICPECA), Shenyang, China, Jan. 22-24, 2021, 83-87.

Henin et al., "Closed-Loop Acoustic Stimulation Enhances Sleep Oscillations But Not Memory Performance," eNeuro, Nov. 2019, 6(6):1-15.

Investopedia.com [online], "Best Series Exam 7 Prep Courses," Feb. 26, 2021, retrieved on May 8, 2024, retrieved via Wayback Machine URL: <https://web.archive.org/web/20210417081004/https://www.investopedia.com/best-series-7-exam-prep-courses-5077599>, 13 pages.

KaplanFinancial.com [online], "How Hard is the FINRA Series 7 Exam?," Kaplan Financial Education, Aug. 26, 2019, retrieved on May 8, 2024, retrieved from URL: <https://www.kaplanfinancial.com/resources/getting-started/how-hard-is-the-series-7-exam>, 7 pages.

Klosh et al., "The SIESTA Project Polygraphic and Clinical Database," IEEE Engineering in Medicine and Biology Magazine, May 2001, 20(3):51-57.

Lakhan et al., "Prescription stimulants in individuals with and without attention deficit hyperactivity disorder: Misuse, cognitive impact, and adverse effects," Brain Behav. Sep. 2012, 2(5):661-677.

Leminen et al., "Enhanced Memory Consolidation Via Automatic Sound Stimulation During Non-REM Sleep," Sleep, 2017, 40(3):1-10.

Liang et al., "Are Wearable EEG Devices More Accurate than Fitness Wristbands for Home Sleep Tracking? Comparison of consumer sleep trackers with clinical devices," 2017 IEEE 6th Glob Conf. Consum. Electron, Nagoya, Japan, Oct. 24-27, 2017, 5 pages.

Marshall et al., "Boosting slow oscillations during sleep potentiates memory," Nature, Nov. 30, 2006, 444(7119):610-613.

Marshall et al., "The contribution of sleep to hippocampus-dependent memory consolidation," Trends Cogn Sci., Oct. 2007, 11(10):442-450.

Navarrete et al., "Examining the optimal timing for closed-loop auditory stimulation of slow-wave sleep in young and older adults," Sleep, Jun. 2020, 43(6):1-14.

Ngo et al., "Auditory Closed-Loop Stimulation of the Sleep Slow Oscillation Enhances Memory," Neuron., May 8, 2013, 78(3):545-553.

Ngo et al., "Driving Sleep Slow Oscillations by Auditory Closed-Loop Stimulation—A Self-Limiting Process," Journal of Neuroscience, Apr. 29, 2015, 35(17):6630-6638.

Ong et al., "Auditory stimulation of sleep slow oscillations modulates subsequent memory encoding through altered hippocampal function," Sleep, May 2018, 41(5):1-11.

Ong et al., "Effects of phase-locked acoustic stimulation during a nap on EEG spectra and declarative memory consolidation," Sleep Med., Apr. 2016, 20:88-97.

O'Reilly et al., "Montreal Archive of Sleep Studies: an open-access resource for instrument benchmarking and exploratory research," J Sleep Res., Dec. 2014, 23(6):628-635.

Owen et al., "Putting brain training to the test," Nature, Jun. 10, 2010, 465(7299):775-778.

Pace-Schott et al., "Age-related changes in the cognitive function of sleep," Progress in Brain Research, 2011, 191:75-89.

Paller et al., "Memory reactivation and consolidation during sleep," Learning & Memory, Nov. 2004, 11(6):664-670.

Papalambros et al., "Acoustic Enhancement of Sleep Slow Oscillations and Concomitant Memory Improvement in Older Adults," Frontiers in Human Neuroscience, Mar. 8, 2017, 11(109):1-14.

Papalambros et al., "Acoustic enhancement of sleep slow oscillations in mild cognitive impairment," Ann Clin Transl Neural., Jul. 2019, 6(7):1191-1201.

Papalambros et al., "Enhancing slow-wave activity in mild cognitive impairment using acoustic stimulation during sleep," Sleep Medicine, Dec. 2017, 40:e251-e252.

Penzel et al., "Dynamics of Heart Rate and Sleep Stages in Normals and Patients with Sleep Apnea," Neuropsychopharmacology, Jun. 24, 2003, 28(1):S48-S53.

Radha et al., "Sleep stage classification from heart-rate variability using long short-term memory neural networks," Sci Rep., Oct. 2, 2019, 9(1):1-11.

Rasch et al., "About Sleep's Role in Memory," Physiol. Rev., Apr. 2013, 93(2):681-766.

(56) References Cited

OTHER PUBLICATIONS

Salfi et al., "Boosting Slow Oscillations during Sleep to Improve Memory Function in Elderly People: A Review of the Literature," Brain Sci., May 15, 2020;10(5).

Santostasi et al., "Phase-Locked Loop for Precisely Timed Acoustic Stimulation during Sleep," J Neurosci Methods, Feb. 2016, 259:101-114.

Shmerling, "FDA curbs unfounded memory supplement claims," Harvard Health Publishing, Aug. 16, 2019, 3 pages.

Skirbekk, "Age and Individual Productivity: A Literature Survey," Vienna Yearbook of Population Research, Aug. 2003, 38 pages.

Sohrabi et al., " The Relationship Between Memory Complaints, Perceived Quality of Life and Mental Health in Apolipoprotein Eε4 Carriers and Non-Carriers," J Alzheimer's Dis., May 2009, 17(1):69-79.

Steriade, "Grouping of Brain Rhythms in Corticothalamic Systems," Neuroscience, Jan. 2006, 137(4):1087-1106.

Talih et al., "Probable Nootropic-induced Psychiatric Adverse Effects: A Series of Four Cases," Innovations in Clinical Neuroscience, Nov. 2015, 12(11-12):21-25.

Technavio.com [online], "Cognitive Assessment and Training Market by End-user and Geography—Forecast and Analysis 2021-2025," Jul. 2021, retrieved on May 8, 2024, retrieved from URL: <https://web.archive.org/web/20210724043841/https://www.technavio.com/report/co gnitive-assessment-and-training-market-industry-analysis>, 5 pages.

TheBarExaminer.ncbex.org [online], "2020 Statistics," The Bar Examiner, 2021, retrieved on May 8, 2024, retrieved from URL: <https://thebarexaminer.org/article/spring-2021/2020-statistics/>, 1 page.

TheBarExaminer.ncbex.org [online], "Persons Taking and Passing the 2020 Bar Examination," The Bar Examiner, 2020, retrieved on May 8, 2024, retrieved from URL: <https://thebarexaminer.ncbex.org/2020-statistics/persons-taking-and-passing- the-2020-bar-examination/>, 4 pages.

TheRecovery Village.com [online], "Adderall for Studying," The Recovery Village, Jan. 21, 2021, retrieved on May 8, 2024, retrieved from URL: <https://web.archive.org/web/20210622210526/https://www.therecoveryvillage.com/ adderall-addiction/adderall-studying/>, 12 pages.

TheRecovery Village.com [online], "College Study Drugs," The Recovery Village, available on or before Apr. 25, 2022, retrieved on May 8, 2024, retrieved from URL: <https://web.archive.org/web/20220525133807/https://www.therecoveryvillage.com/ drug-addiction/study-drugs/>, 4 pages.

Timofeev, "Neuronal plasticity and thalamocortical sleep and waking oscillations," Progress in Brain Research, Jan. 2011, 193:121-144.

USMLE.org [online], "Performance Data—2020," US Medical Licensing Examination, 2021, retrieved on May 8, 2024, retrieved from URL <https://www.usmle.org/performance-data/>, 8 pages.

Varela et al., "The Brainweb: Phase Synchronization and Large-scale Integration," Nature Reviews Neuroscience, Apr. 2001, 2(4):229-239.

Weigenand et al., "Timing matters: open-loop stimulation does not improve overnight consolidation of word pairs in humans," Eur J Neurosci., Sep. 2016, 44(6):2357-2368.

Wilhelm et al., "The sleeping child outplays the adult's capacity to convert implicit into explicit knowledge," Nat. Neurosci., 2013, 16(4):391-393.

Yuda et al., "Sleep Stage Classification by a Combination of Actigraphic and Heart Rate Signals," J Low Power Electron Appl., Nov. 13, 2017, 7(28):1-7.

Zuniga et al., "Subjective Memory Impairment and Well-Being in Community-Dwelling Older Adults," Psychogeriatrics, Jan. 2016, 16(1):20-26.

* cited by examiner

SENSING SYSTEM WITH FEATURES FOR DETERMINING AND PREDICTING BRAIN AGE AND OTHER ELECTROPHYSIOLOGICAL METRICS OF A SUBJECT

RELATED APPLICATIONS

This application claims priority to U.S. Provisional Application No. 63/333,832, filed on Apr. 22, 2022 and U.S. Provisional Application No. 63/402,756, filed on Aug. 31, 2022. The entire contents of which are hereby incorporated by reference.

STATEMENT OF GOVERNMENT INTEREST

This invention was made with Government support under 1R41AG085773-01, 2151469, and FA864922P1178 awarded by the National Institutes of Health, the National Science Foundation and the Department of the Air Force, respectively. The Government has certain rights in the invention.

TECHNICAL FIELD

This document describes systems and computer-implemented methods for providing improved determination of a physiological metrics of a subject.

BACKGROUND

Neurodegenerative disorders and diseases can be difficult to detect for early intervention, and the early signs of neurodegeneration can go unnoticed until intervention may be too late. Early detection of accelerated decline in brain anatomy and function can lead to early intervention, which is the time when interventions are most effective. Neurodegenerative disorders such as Alzheimer's, Huntington's, Parkinson's, and others can occur as people get older. Neurodegeneration can occur at various different chronological ages for different people based on a variety of factors such as such as demographics (e.g., gender, race, ethnicity or family histories), health conditions, health diagnoses, current or prior behaviors (e.g., smoking, alcohol consumption, exercise, diet, among others), historical behaviors, and environmental factors.

While a chronological age can be easily determined, a person's brain age may differ from their chronological age. In some instances, neurodegeneration can cause a person's brain age to be greater (i.e., older) than their chronological age. Accordingly, brain age has been used as a biomarker of aging, due to the effects of age on the structural and functional properties of the human brain.

Current solutions to determine a person's brain age use structural and functional MRI scans or laboratory-based polysomnographic (PSG) recordings, which are costly, inappropriate as a large-scale screening tool, and inappropriate for continuous monitoring over multiple nights.

The four phases of sleep include a stage referred to as deep sleep, slow wave sleep (SWS), or N3 sleep. Each of the four phases of sleep have physiologic characteristics and benefits that can differ between the phases. Deep sleep has a role in declarative memory consolidation, as well as a restorative role associated with energy restoration, immunity, hormone regulation, and cleaning of metabolites.

Closed-loop auditory stimulation of sleep slow oscillations (SOs) is an approach to deep sleep enhancement. However, sensory (e.g., auditory) stimulation during sleep is often applied at times that do not correctly correspond to the aimed sleeping patterns of a subject, such as the positive SO peak. Additionally, bioelectrical signals (e.g., electroencephalogram or EEG signals) can include signal noise that is challenging to filter in real time because filtering introduces shape and phase distortions in bioelectrical signals (e.g., EEG).

SUMMARY

This document describes techniques, methods, and systems for determining physiological metrics of a subject and for real-time prediction of events of a subject's brain function. Some embodiments of systems and methods detailed herein include providing improved device and method that extract and analyze biological features during sleep from EEG and other biosensors, and user characteristics (e.g., gender, race, ethnicity or family histories), health conditions, health diagnoses, current behaviors, and historical behaviors (e.g., use of alcohol, drugs, exercise, etc.) and environmental factors. The biological features and user characteristics can be analyzed and compared to biological features and user characteristics of the same by age group, by the same gender, or by other groups or factors to calculate physiological metrics of the subject and provide a level of confidence for the calculated metrics. For example, the other groups can include groups based on activity level, geographic location, education level, professional level, lifestyle groups, pre-menopausal and post-menopausal groups, menstrual cycle groups, among others. In some aspects, the physiological metrics can be a biological brain age of the subject.

In some embodiments, a system for use in determining metrics of a subject is provided. The system includes one or more processors and a memory storing instructions that, when executed by the processors, cause the processors to perform operations. The operations may include: receiving physiological measures of the subject recorded at least partly while the subject is asleep. The instructions also include receiving demographic data for the subject, the demographic data may include a chronological age for the subject when the physiological measures were recorded. The instructions also include generating, using the physiological measures and from the demographic data, segmented training-data that specifies a plurality of epochs of time and data for the subject in each epoch. The instructions also include generating, using the segmented training-data, sleep-structure features for the subject. The instructions also include selecting a subset of the sleep-structure features as selected features. The instructions also include generating, using the selected features, one or more function-metric classifiers may include training a model that defines at least one relationship between the physiological measures and the chronological age, the function-metric classifier configured to: receive, as input, new physiological measures. The instructions also include provide, as output, a function-metric value determined based on the defined relationship between the physiological measures and the chronological age.

Implementations may include one or more of the following features. The demographic data includes at least one of the group consisting of an identifier, a gender, sociodemographic data, medical data, behavioral data, and lifestyle data that have been entered by the subject into an input device of the system. The physiological measures of the subject may include at least one of the group consisting of a frontal electroencephalography (EEG) channel, two frontal EEG channels, forehead photoplethysmography (PPG), blood oxygen saturation ($SPO_2$), electromyography (EMG), electrooculography (EOG), electrodermal activity (EDA), and actigraphy data. The physiological measures of the subject can be recorded at least partly while the subject is asleep and provided with at least one stimuli of the group consisting of audio stimuli, light stimuli, vibratory, electrical stimuli, open-loop stimuli, and closed-loop stimuli; and the physiological measures may include timing info defining timing of stimuli provided to the subject.

Implementations may include one or more of the following features. Generating, using the physiological measures and from the demographic data, segmented training-data may include: applying band-pass filters to at least some of the physiological measures; combining at least two frontal/prefrontal EEG signals to create a virtual frontal/prefrontal EEG signal; detecting artifacts in the acquired signals, e.g. movement artifacts; extracting heartbeat times from PPG signals by detecting peaks in the PPG signals; segmenting the physiological measures into a plurality of epochs of time; generating, for each epoch of time, at least one of the group may include of multiple time-domain features, frequency domain features, and nonlinear or complex signal descriptives; accessing tagging data that tags each epoch of time with a sleep stage from the group may include of wakefulness, rapid eye movement (rem) sleep, non-rem sleep stage 1 (n1), non-rem sleep stage 2 (n2), non-rem sleep stage 3 (n3), and non-rem sleep stage 4 (n4). Generating, using the segmented training-data, sleep-structure features for the subject may include: determining macrostructure features for the subject describing at least one of the group may include of sleep-stage duration, sleep-stage percentage, sleep-stage transition probability, sleep fragmentation, and awakenings; determining microstructure features for the subject describing at least one of the group may include of stage-specific EEG features, waveform-specific EEG features, and stimulus-response EEG features; determining cardiac features for the subject using at least one of the group may include of heartbeat times and tagging data that tags epochs of time with sleep stage; and determining respiratory features for the subject describing at least one of the group may include of blood oxygenation, heart rate, heart beat times, and sleep apnea, using at least one of the group may include of blood oxygen saturation ($SPO_2$) and the tagging data.

Implementations may include one or more of the following features. Selecting a subset of the sleep-structure features as selected features may include: transforming at least one of a plurality of features selected from the group may include of macrostructure features, microstructure features, cardiac features, and respiratory features; and aggregating sleep-structure features from multiple sleep-sessions. Selecting a subset of the sleep-structure features as selected features may include sequentially calculating the cross-validated mean absolute error (MAE) with a regression model, where the regression model is an extreme learning machine (ELM) regressor, a least absolute shrinkage and selection operator (LASSO), or a regression model trained under the Gradient Boosting framework (e.g. gradient boosted trees).

Implementations may include one or more of the following features. Training the model that defines at least one relationship between the physiological measures and the chronological age may include determining hyperparameters for the model using a Bayesian optimization algorithm targeting a repeated k-fold cross-validation using at least one of the group may include of a regression problem; a regression with a loss function based on a residual-label covariance analysis; a deep label distribution learning algorithm based on neural networks; a cascade of a multi-class classification model (e.g. a support vector machine) followed by several regression models where each is trained for a specific demographic or physiological class (group). Training a model that defines at least one relationship between the physiological measures and the chronological age may include refining the model to reduce age-dependent bias. The classifier is further configured to provide, as output, at least one of the group may include of a confidence value, a variance-from-chronological-age value, a model interpretation, an interpretation of the model's output, a human-readable instruction displayable to a user of an output device, and an automation-instruction that, when executed by an automated device causes the automated device to actuate. The operations further may include distributing the function-metric classifiers to a plurality of user devices that are configured to sense new physiological measures of other subjects at least partly while the other subjects are asleep. The operations further may include: receiving new physiological measures of the subject recorded at least partly while the subject is asleep and recorded after the function-metric classifiers have already been generated; submitting the new physiological measures to at least one of the function-metric classifiers as the input; and receiving as output from the at least one function-metric classifier the function-metric value.

In an example embodiment, a method for providing stimulation to a subject is provided. The method can include receiving a data-stream for the subject, the data-stream comprising a real-time EEG signal generated by one or more EEG sensors gathering data of ongoing brain activity of the subject; identifying in the data-stream a record of a current slow oscillation (SO) that contains data of an incomplete SO of the ongoing brain activity; extracting one or more SO features for the current SO from the record of the current SO; determining, from the SO features, one or more predicted SO values, the predicted SO values each being a prediction of a future event at which the current SO will exhibit a target morphology.

Implementations may include one or more of the following features. The method can include engaging a stimulation device to provide the subject with a stimulation signal based on the predicted SO values such that the subject receives the stimulation signal while the brain activity of the subject is generating the current SO. The method can include determining a delay interval based on the predicted SO values; delaying for the delay interval; and sending an activation command to the stimulation device upon expiration of the delay interval. The method can include engaging the stimulation device comprises determining that the current SO is a typical SO. The method where the one or more SO features that are extracted are selected from the group (SO group) may include of i) a positive-to-negative zero-crossing (zx1), ii) a negative-to-positive zero-crossing (zx2), iii) a point after zx1 at which a slope of the data-stream falls under a negative threshold (steady1), iv) SO negative peak timing (neg_time), v) a point before zx2 at which the data-stream falls under a defined positive threshold (steady), vi) a SO positive peak timing (pos_time), and vii) a points at which data-stream value exceeds a defined percentage of the SO negative peak amplitude (neg_percent). The one or more predicted SO values are also selected from the SO group. The one or more SO values are different than the SO group. The method can include determining, from the SO features, one or more predicted SO values may include submitting, to a so-classifier, the SO features and receiving the predicted SO values. The so-classifier is created via training on a dataset of training-so features and matching training-so values. The dataset is constructed to exclude atypical training-so features. The classifier is retrained using the SO features of a single night's sleep during the single night's sleep. The classifier is trained for a specific morphological type of SO. The classifier is trained for the subject using training data from the subject. The classifier is trained in real-time using the data from a current sleep session. The method can include determining of one or more predicted SO values is responsive to determining that the subject is in a particular sleep stage Implementations of the described techniques may include hardware, a method or process, or computer software on a computer-accessible medium.

In an example embodiment, a system for providing stimulation to a subject is provided. The system can include a data acquisition device that can include a body, one or more EEG sensors, and at least one stimuli generator. The system also includes one or more processors and memory storing instructions that, when executed by the processors, cause the processors to perform operations. The operations may include: receiving a data-stream for the subject, the data-stream may include a real-time EEG signal generated by the one or more EEG sensors gathering data of ongoing brain activity of the subject; identifying in the data-stream a record of a current slow oscillation (SO) that contains data of an incomplete SO of the ongoing brain activity; extracting one or more SO features for the current SO from the record of the current SO; and determining, from the SO features, one or more predicted SO the predicted SO timings each being a prediction of a future event (e.g., time, amplitude, category) at which the current SO will exhibit a target morphology.

Implementations may include one or more of the following features. The system where the body is a headband that includes a curved shape that is configured to extend around each ear of a subject and under a nape of the back of a subject's head. The operations may include: engaging the at least one stimuli generator to provide the subject with a stimulation signal at the predicted SO values such that the subject receives the stimulation signal while the brain activity of the subject is generating the current SO. The stimuli generator generates audio stimuli. The operations may include: determining, from the SO features, one or more predicted SO values may include submitting, to a so-classifier, the SO features and receiving the predicted SO values. The one or more SO features that are extracted are selected from the group (SO group) may include of i) a positive-to-negative zero-crossing (zx1), ii) a negative-to-positive zero-crossing (zx2), iii) a point after zx1 at which a slope of the data-stream falls under a negative threshold (steady1), iv) SO negative peak timing (neg_time), v) a point before zx2 at which the data-stream falls under a defined positive threshold (steady), vi) a SO positive peak timing (pos_time), and vii) a points at which data-stream value exceeds a defined percentage of the SO negative peak amplitude (neg_percent). The method where engaging the stimulation device may include: determining a delay interval based on the predicted SO values; delaying for the delay interval; and sending an activation command to the stimulation device upon expiration of the delay interval. Implementations of the described techniques may include hardware, a method or process, or computer software on a computer-accessible medium.

Implementations may include one or more of the following features. The method where engaging the stimulation device may include: determining a delay interval based on the predicted SO values; delaying for the delay interval; and sending an activation command to the stimulation device upon expiration of the delay interval. Implementations of the described techniques may include hardware, a method or process, or computer software on a computer-accessible medium.

Particular implementations can, in certain instances, realize one or more of the following advantages. For example, the described systems and methods can advantageously provide users with the ability to assess their functional metrics in a single night's sleep or over multiple nights' sleep. This can provide the user a short-term result based on a single night's sleep and a longer term result based on multiple nights' sleep data that can be compared to identify trends. By providing a result based on multiple nights' sleep, the described systems and methods can advantageously mitigate the issue of night-to-night variability in the used biological sleep features. The users can also be provided with assessments of their physiological metrics that are consistent with early signs of cognitive decline. Additionally, the determined brain age from the described systems and methods can be obtained and provided to the subject when the subject is in their normal sleep environment (e.g., at home). This provides data to the user when they are not disturbed by anxiety, not in an unfamiliar environment or uncomfortable bed, or other factors that would impact their ability to sleep normally. The described systems and methods do not involve a technician installing multiple uncomfortable leads on the subject, which can be advantageous for the subject because the system is much accessible as well as being more time and cost effective than a sleep-study, MRI, or other brain function tests that take place in a clinical environment. The system can also be used to monitor effectiveness of clinical or wellness interventions. For example, the system can assess if a medication, drug, or other intervention slowed the progression of brain age for the subject. The system can assess if taking up meditation, improving sleep hygiene, exercising, or joining peer groups have an impact on the progression of brain age.

Because SO-spindle coupling is believed to be impaired during traumatic brain injury (TBI), this technology can be used to aid in diagnosing or measuring severity of TBI. Limited diagnostic methods are previously available to detect and characterize TBI. CT and MRI scans can detect bleeding from TBI but struggle with detection of non-structural damage. The symptoms of mild TBI (mTBI) lack specificity making diagnosis challenging. However, accurate diagnosis is important to prevent repetitive injury and the risk of "second impact syndrome" in which a subject suffers a second impact injury before the previous injury is fully healed. In order to facilitate accurate diagnosis, an objective, sensitive, non-invasive way to assess TBI is required, which can be provided by this technology. Memory consolidation is believed to be dependent upon the synchronization of the hippocampus, thalamus and medial prefrontal cortex (mPFC) bidirectional communication during Slow Wave Sleep (SWS). TBI is believed to impure this synchronization. Therefore, this technology can provide a functional assessment of TBI and identify lingering impacts, and users (e.g., clinicians, patients, researchers) can trust this assessment as objective, sensitive, a product of a non-invasive process.

For example, the described systems and methods can advantageously provide precisely timed stimulation events based on a robust estimation of the filter distortion based on the currently detected event in real-time. Additionally, the described systems and methods advantageously provide a functional relationship between the morphology of the currently detected event and the expected filter distortion. The systems and methods described herein advantageously provide a within-event approach to stimulation timing (e.g., a within-SO approach), such that the prediction of an outcome (e.g., the timing of the SO positive peak) within an ongoing event is tailored based on the characteristics of the ongoing event, and not only limited to previous events. Additionally, the described systems and methods can advantageously provide the decision on whether or not to apply the sensory stimulation based on the morphology of the currently detected event in real-time.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

This document describes techniques, methods, and systems for determining physiological metrics of a subject. Some embodiments of systems and methods detailed herein include providing improved device and method that extract and analyze biological features during sleep from EEG and other biosensors, and user characteristics (e.g., gender, race, ethnicity or family histories), health conditions, health diagnoses, current behaviors, and historical behaviors (e.g., use of alcohol, drugs, exercise, environmental factors, etc.). The biological features and user characteristics can be analyzed and compared to biological features and user characteristics of the same by age group to calculate physiological metrics of the subject and provide a level of confidence for the calculated metrics. In some aspects, the physiological metrics can be a biological brain age of the subject.

This document describes techniques, methods, and systems for determining the timing of a subject's electrophysiological events with sufficient speed and precision that the predictions can be used for the timing of, for example, stimulus to the subject via a worn medical or wellness device as the subject sleeps. For example, some types of auditory, electrostimulative, or tactile stimulation can call for timing precision in order to be delivered during particular points in a slow wave oscillation (SO) of brain activity (e.g., coordinated activity of large populations of neurons consisting of an alternation of active periods of Up states and silent periods of Down states), and this technology can be used to predict, based on sensing of early portions of the SO, timing of events later in the same SO. This can allow for accurate and fast real-time sensing, predicting, and stimulating, in a way that is not possible with, for example, post-sensing processing of SO data done after a sleep session, or from data from prior SOs in the same sleep session, or other sensing sessions.

Figure 1:
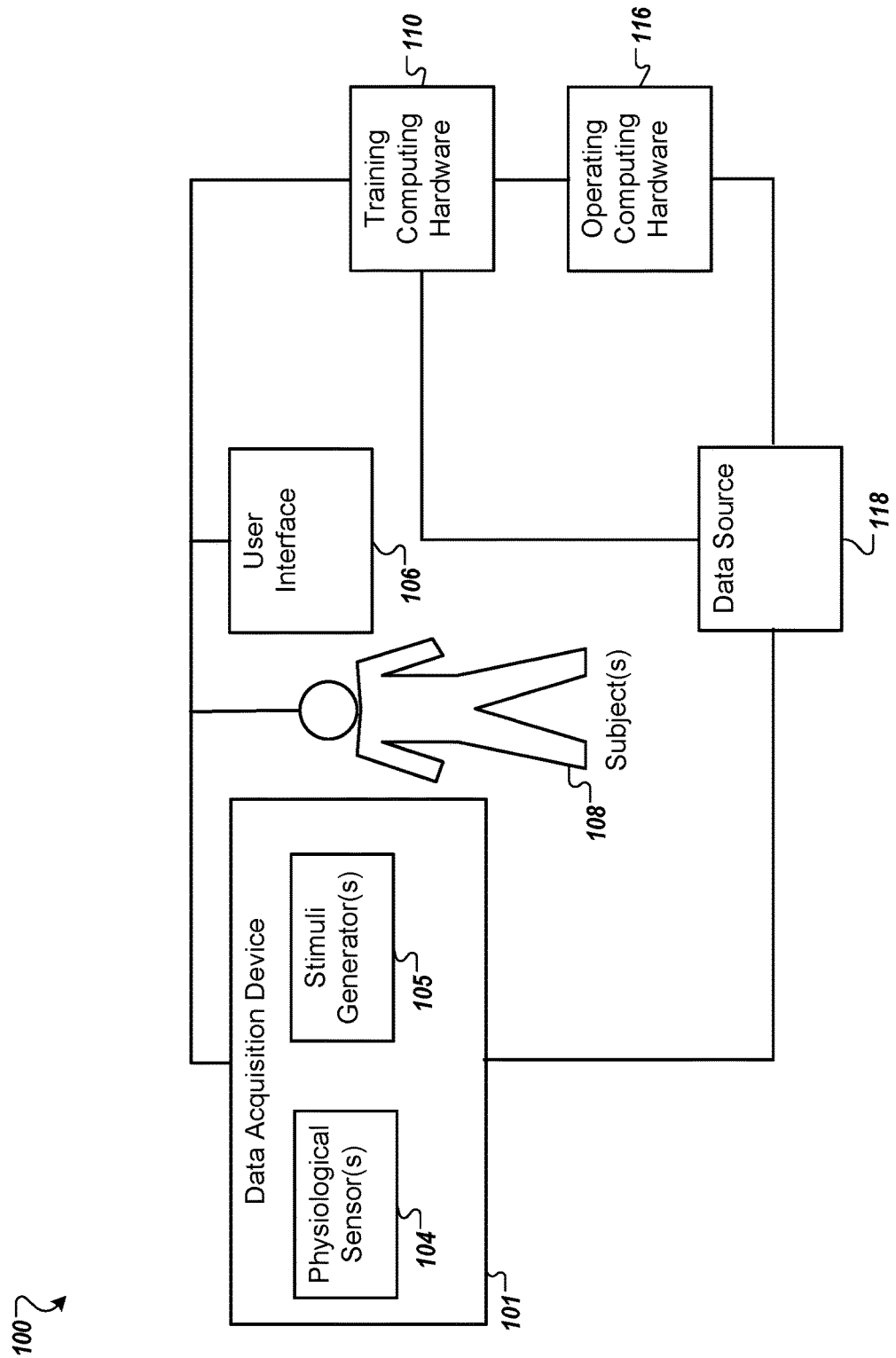
FIG. 1 shows an example system for determining a functional metric of a subject, consistent with embodiments of this disclosure.

Referring to the figures, FIG. 1 illustrates an example of a system 100 for determining physiological metrics of a subject. The system 100 can include a data acquisition device 101 that has one or more physiological sensors 104 and one or more stimuli generators 105. The system 100 can include a user interface 106, training computer hardware 110, operating computing hardware 116, and a data source 118. The system 100 can be configured to collect data from one or more subjects 108, as will be described in further detail below.

In some aspects, the data acquisition device 101 can be worn by the subject 108 to collect data from the one or more physiological sensors 104. For example, the data acquisition device 101 can be configured to detect, measure, monitor, and record brain activity using electroencephalography (EEG), eye activity using electrooculography (EOG), muscle activity using electromyography (EMG), cardiac activity using electrocardiography (ECG), respiration rate (e.g., using respiratory inductance plethysmography (RIP), pressure sensor, and/or a temperature sensor), oxygen saturation (e.g., using pulse oximetry), heart rate (HR), blood flow, actigraphy during sleep, or any combination thereof. The stimuli generators 105 can generate audio stimuli, optical stimuli, visual stimuli, tactile stimuli, or combinations thereof to the subject 108, and the physiological sensors 104 can collect data that reflects the subject's 108 response to the stimuli.

The data collected by the data acquisition device 101 can be communicated throughout the system 100. For example, the data from the data acquisition device 101 can be displayed at the user interface 106, sent to the training computing hardware 110, sent to the operating computing hardware 116, and sent to the data source 118. Each of the data acquisition device 101, the user interface 106, the training computing hardware 110, and the operating computing hardware 116 can perform one or more of the processing steps described in further detail below (see e.g., FIGS. 4-6).

Figure 2:
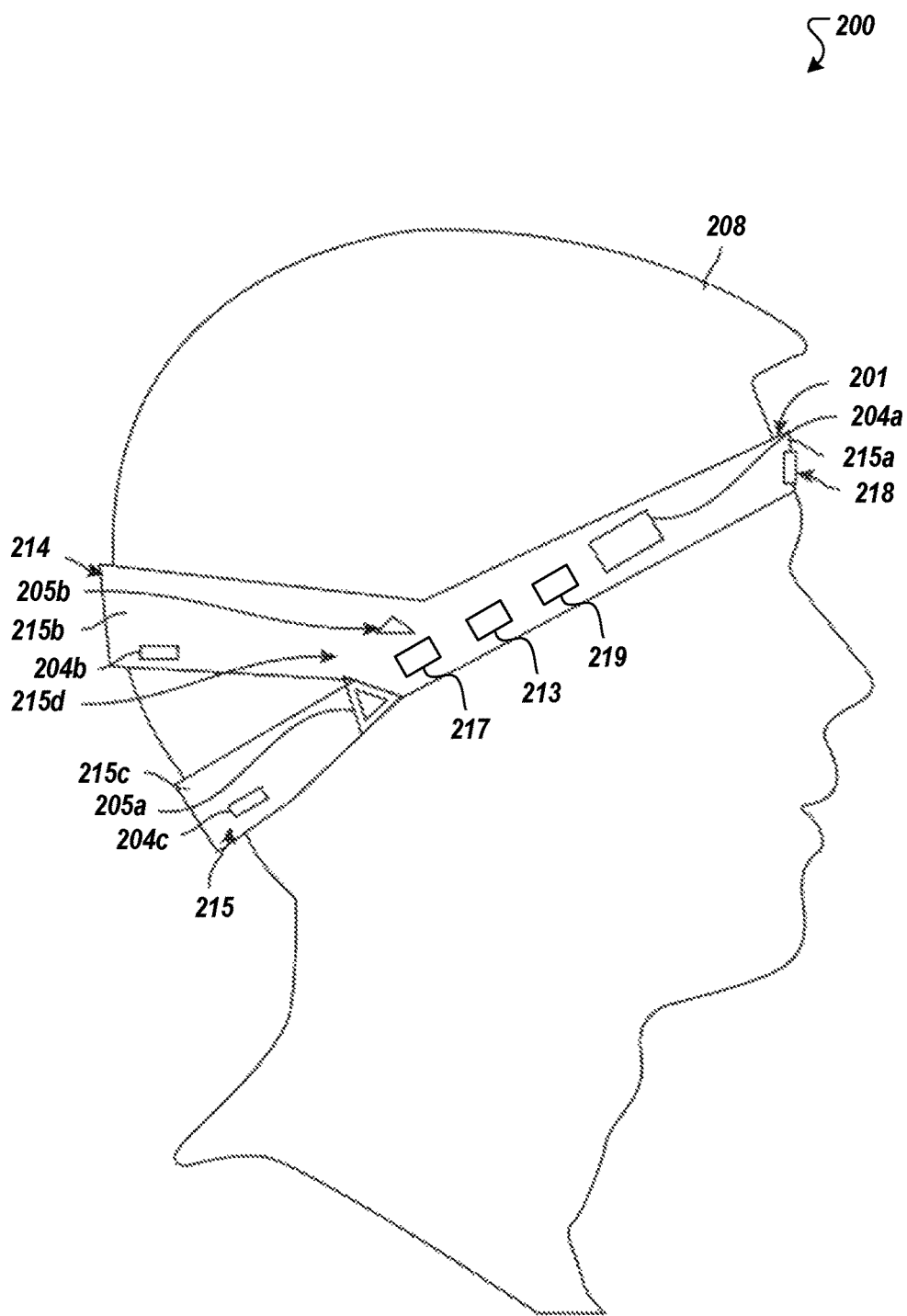
FIG. 2 shows an example data acquisition device on the head of a subject.

Referring now to FIG. 2, an example of a data acquisition system 200 that includes a data acquisition device 201 is shown. In some aspects, the data acquisition device 201 can be the data acquisition device 101 of FIG. 1. The data acquisition device 201 can be a head-worn sensing device that includes one or more sensors. The data acquisition device 201 can have a body 214 that can be a breathable material, for example a mesh material. The breathable material can allow the skin beneath the body 214 to breathe. The breathable material can be elastic and/or inelastic. The elastic properties of the body 214 can be configured to inhibit or prevent the data acquisition device 201 from slipping during use, such as when the user moves during sleep (e.g., when the user shifts position or when one of their limbs or another person contacts the data acquisition device 201). The body can extend partially or completely around a perimeter of a head 208 of a subject.

The data acquisition device 201 can be a removably attachable headband, cap, hat, strip (e.g., adhesive or hook-and-loop style fastening strip), biased band, or any combination thereof. The data acquisition device 201 can have the shape of a closed or open loop (e.g., annular or semi-annular shape). The data acquisition device 201 can extend partially or completely around a perimeter of the head 208.

The data acquisition device 201 can have a body 214 comprising multiple bands 215, for example, a first band 215a, a second band 215b, and a third band 215c. The first, second, and third bands 215a, 215b, 215c can be separate bands and/or can be different band portions of a single unitary band. For example, the first, second, and/or third bands 215a, 215b, 215c can be attached to or integrated with one another at attachment region 215d. The data acquisition device 201 can form a headband. The first band/band portion 215a can form a front band/strap. The second and third bands/band portions 215b, 215c can form back bands/straps. The data acquisition device 201 can have a 'split band' in the back of the head 208 formed by the second and third straps 215b, 215c, where the bottom band (e.g., the third band 215c) can be configured to cup under the curve of the back of the head to reduce any potential slippage/movement of the headband.

A band adjuster 205a can enable back straps (e.g., bands 215b and 215c) to adjust to contour to person's head. The band adjuster 205a can allow the second band 215b to be adjusted independently from the third band 215c. The band adjuster 205a can allow the third band 215c to be adjusted independently from the second band 215b. The band adjuster 205a can allow the angle between the second and third bands 215b, 215c to be adjusted. Alternatively or additionally, the data acquisition device 201 can have another band adjuster 205b that can have the same functionality as the band adjuster 205a. The data acquisition device 201 can have one or more length adjustment mechanisms configured to allow the length of the one or more bands to be increased, decreased, and/or locked into position. For example, the data acquisition device 201 can have a first length adjustment mechanism 204a for the first band/band portion 215a, a second length adjustment mechanism 204b for the second band/band portion 215b, a third length adjustment mechanism 204c for the third band/band portion 215c, or any combination thereof.

The elastic body and slip resistant edges can be configured to keep one or more sensors of the data acquisition device 201 in position during use such that there is strong contact and less resistance to movement at the point where the sensors come into contact with the skin. This can advantageously ensure that the device sensors can have reliable contact with the skin.

Alternatively or additionally, the data acquisition device 201 can have one or multiple expandable mechanisms 204a, 204b, 204c configured to keep the sensors of the data acquisition device 201 in position during use such that there is strong contact and less resistance to movement at the point where the sensors come into contact with the skin. The expandable mechanism can allow the sensors to contact the skin with precise pointed pressure (e.g., from pressure provided by the expandable mechanism). The expandable mechanism can be behind one or more sensors of the data acquisition device 201, for example, behind all of the sensors of the data acquisition device, or behind any lesser number of sensors of the data acquisition device 201. The expandable mechanism can be an inflatable bladder. The expandable mechanism (e.g., the inflatable bladder) can be configured to expand to press one or more sensors into the skin. The expandable mechanism can remain expanded during use.

The expandable mechanism can be expanded from an unexpanded configuration to an expanded configuration. The unexpanded configuration can have a first volume and the expanded configuration can have a second volume larger than the first volume. The first volume can be zero or greater than zero. The second volume can be, for example, about 1 mL to about 50 mL, including every 1 mL increment within this range. The expandable mechanism can be expanded until a predetermined pressure threshold is detected between the skin and one or more of the device sensors, for example, by one or more pressure sensors associated with the expandable mechanism. The expandable mechanism (e.g., inflatable bladder) can advantageously enable the data acquisition device 201 to create skin-sensor contacts that have known and reproducible skin-sensor contact pressures or other measurable quantity that can characterize the contact between the sensors and the skin, or that otherwise fall within an acceptable tolerance such that the device can accurately and precisely record various physiological activity of the subject (e.g., brain activity).

The data acquisition device 201 can be configured to measure and collect one or more physiological parameters during sleep. For example, the data acquisition device 201 can be configured to detect, measure, monitor, and record brain activity, eye activity, muscle activity (e.g., body posture, limb movements), cardiac activity (e.g., heart rate, heart rate variability (HRV)), respiration activity (e.g., respiration rate), blood oxygen saturation, blood flow rates, or any combination thereof. For example, the data acquisition device 201 can be configured to detect, measure, monitor, and record brain activity using electroencephalography (EEG), eye activity using electrooculography (EOG), muscle activity using electromyography (EMG), cardiac activity using electrocardiography (ECG), respiration rate (e.g., using respiratory inductance plethysmography (RIP), pressure sensor, and/or a temperature sensor), oxygen saturation (e.g., using pulse oximetry), heart rate (HR), blood flow, actigraphy during sleep, or any combination thereof.

The data acquisition device 201 can be configured to detect, measure, monitor, and record pressure and temperature, for example, using one or more pressure sensors and/or one or more temperature sensors. The data acquisition device 201 can perform polysomnography (PSG) tests and can collect polysomnographic data. The data that is collected is referred to throughout as acquired data, raw data, and/or sleep data.

The data acquisition device 201 can have one or more data acquisition modules 218 (also referred to as electronics modules 218), for example, 1 to 5 data acquisition modules 218, including every 1 module increment within this range (e.g., 2 electronics modules). For example, the data acquisition device 201 can have one electronics module 218. In another example, the data acquisition device 201 can have a plurality of data acquisition modules 218 spaced apart around the data acquisition device 201 to provide sensors at a variety of positions around the head 208 of the subject to optimize data collection.

The one or more data acquisition modules 218 can be configured to monitor and record one or more physiological activities during sleep. For example, the data acquisition modules 218 can be configured to detect, measure, monitor, and record brain activity, eye activity, muscle activity, cardiac activity, respiration activity, blood oxygen saturation, blood flow, actigraphy, or any combination thereof (e.g., using EEG, EOG, EMG, ECG, RIP, pulse oximetry, or any combination thereof, respectively). The one or more data acquisition modules 218 can be computer interfaces, for example, brain computer interfaces (BCIs).

The data acquisition modules 218 can have one or more electrodes, sensors (e.g., biosensors), accelerometers, or any combination thereof. For example, the data acquisition modules 218 can have one or more EEG biosensors, EOG biosensors, EMG biosensors, ECG biosensors, respiration rate biosensors, pulse oximetry biosensors, HRV biosensors, temperature sensors, pressure sensors, or any combination thereof, including one or more reference sensors and/or one or more ground electrodes.

The data acquisition modules 218 can have a single-channel and/or a multi-channel EEG system. The multi-channel EEG system can be operated as a single channel EEG system. The EEG system (single or multi-channel) can include one or more EEG sensors. The data acquisition device 201 (e.g., the data acquisition modules 218) can have 1 to 10 EEG sensors, including every 1 EEG sensor within this range (e.g., 4 EEG electrodes). The data acquisition modules 218 can have more than 10 sensors (e.g., 1 to 100 EEG sensors). The data acquisition modules 218 can have an EEG sensor array or an EEG sensor network (e.g., of 2 to 10 or more sensors). One of the EEG sensors can be a ground electrode. The EEG system can have one or multiple reference electrodes (e.g., one or two reference electrodes). The electronics module 218 can have, for example, three channels of frontal EEG and one EEG reference sensor or three channels of prefrontal EEG and one EEG reference sensor. The EEG electrodes can be positioned on the forehead, for example, the EEG electrodes can be placed at forehead positions such as Fp1 and Fp2. The EEG electrodes can be placed according to the international 10-20 system.

The data acquisition modules 218 can have 2, 3, or 4 EOG sensors. Two EOG sensors can detect/measure movement of one or both eyes. For example, two EOG sensors can be positioned to detect/measure eye movement of the left and right eyes (e.g., a first EOG sensor can be positioned on the right outer edge of the right eye and a second EOG sensor can be positioned on the left outer edge of the left eye), two EOG sensors can be positioned to detect/measure eye movement of only the left eye (e.g., a first EOG sensor can be positioned on the right outer edge and a second EOG sensor can be positioned on the left outer edge of the left eye), or two EOG sensors can be positioned to detect/measure eye movement of only the right eye (e.g., a first EOG sensor can be positioned on the right outer edge and a second EOG sensor can be positioned on the left outer edge of the right eye). Three EOG sensors can be positioned to detect/measure eye movement of the left and right eyes (e.g., a first EOG sensor can be positioned on the right outer edge of the right eye, a second EOG sensor can be positioned on the left outer edge of the left eye, and a third EOG sensor can be positioned between the left and right eyes). The three EOG sensors can selectively detect/measure eye movement of the left and/or right eyes, with the first and third EOG sensors configured to detect/measure movement of the right eye, with the second and third EOG sensors configured to detect/measure movement of the left eye, and with the first and second EOG sensors configured to detect/measure movement of the left and right eyes together. Four EOG sensors can be positioned to detect/measure eye movement of the left and right eyes (e.g., first and second EOG sensors can be positioned on first and second sides of the left eye and third and fourth EOG sensors can be positioned on first and second sides of the right eye). The "outer edges" of the eyes can be in line with the eyes, above the eyes and/or below the eyes.

The data acquisition system 200 can have 1 to 6 EMG sensors, including every 1 EMG electrode increment within this range (e.g., 2 EMG electrodes).

The data acquisition system 200 (e.g., the data acquisition device 201 and/or the data acquisition modules 218) can have 1 to 10 ECG sensors, including every 1 ECG electrode increment within this range (e.g., 1, 2, or 3 ECG electrodes). The ECG sensors can be used to measure HRV. The ECG sensors can be used to determine HRV.

The data acquisition system 200 (e.g., the data acquisition device 201 and/or the data acquisition modules 218) can have 1 to 10 heart rate sensors, including every 1 heart rate sensor increment within this range (e.g., 1, 2, or 3 heart rate sensors). The heart rate sensors can be used to measure HRV. The heart rate sensors can be used to determine HRV.

The data acquisition system 200 (e.g., the data acquisition device 201 and/or the data acquisition modules 218) can have one or multiple pressure sensors (e.g., pressure transducers) and/or temperature sensors (e.g., thermocouples) configured to monitor respiration. For example, the data acquisition device 201 can have 1 to 4 pressure sensors, including every 1 pressure sensor increment within this range (e.g., 1 or 2 pressure sensors). The data acquisition device 201 can have 1 to 4 temperature sensors, including every 1 temperature sensor increment within this range (e.g., 1 or 2 temperature sensors). The pressure and/or temperature sensors can be positionable near the nostrils and can be configured to detect the pressure/temperature changes that occur when a user inhales and exhales. The pressure and/or temperature sensors can be attached to or integrated with the data acquisition device 201 such that when the data acquisition device 201 is removably secured to a head, the pressure and/or temperature sensors are positioned in a breathing flow path (e.g., near the nostrils and/or mouth, for example, for mouth breathers).

The data acquisition device 201 can have a pulse oximetry sensor that can be removably attachable to an ear, for example, to an ear lobe. The data acquisition system 200 can have a pulse oximetry sensor that can be removably attachable to a finger. The finger pulse oximetry sensor can be in wired or wireless communication with the data acquisition device 201 (e.g., to the electronics module 218) and/or to the data display device. The ear pulse oximetry sensor can be attached to or integrated with the data acquisition device 201. The pulse oximetry sensor (ear and finger sensor) can be a component of a clip. The clip can attach to (e.g., clip to) an ear lobe or a finger. The clip can be attached to or integrated with the data acquisition device 201, for example, to the body 214. The pulse oximetry sensor can be placed on the forehead. The forehead pulse oximetry can be attached to or integrated in the data acquisition device 201.

The data acquisition device 201 can have one or more pressure sensors (e.g., 1, 2, 3, 4, 5, 6 or more) configured to detect when the data acquisition device 201 is attached to a head, for example, by measuring the amount of force exerted against each of the pressure sensors. The data acquisition system 200 can be configured to detect whether the data acquisition device 201 is properly positioned on the head, for example, by detecting and/or comparing the different pressures measured by the one or more pressure sensors (e.g., by calculating one or more pressure differentials). The pressure sensors can also be used to determine whether the position can be improved or further optimized, for example, for more accurate and/or reliable data collection. The data acquisition device 201 can be activated (e.g., automatically or manually) when positioned on the head 208 as a result of one or more pressure sensors exceeding a pressure threshold. The data acquisition device 201 can be activated (e.g., automatically or manually) when positioned on the head 208 as a result of one or more differential pressure differentials (e.g., between two sensors) falling below a differential pressure threshold.

For example, a first pressure sensor can be on a first side of the data acquisition device 201 and a second pressure sensor can be on a second side of the data acquisition device 201. The pressure sensors can be separated by about 1 degree to about 180 degrees as measured from a center of the data acquisition device 201 (e.g., along a longitudinal and/or transverse axis), including every 1 degree increment within this range. The center of the data acquisition device 201 can fall between two inner sides of the device such that the device center is not on the body and/or edges of the data acquisition device 201. A 180 degree separation can correspond to a configuration in which the first and second pressure sensors are diametrically opposed from one another. Angles less than 180 degrees can correspond to configurations in which the first and second pressure sensors are on opposite sides of the device, determined for example relative to a reference axis. Angles less than 180 degrees can correspond to configurations in which the first and second pressure sensors are on the same side of the device, determined for example relative to a reference axis. The first and second pressure sensors can be used to determine a side-to-side or a front-to-back pressure differential of the data acquisition device 201 (i.e., the pressure levels on the left side, right side, front side, and/or back side of the data acquisition device 201). Four pressure sensors can be used to determine side-to-side and/or front-to-back pressure differentials of the device when removably attached to a head. The angles between sensors can be from about 1 degree to about 180 degrees, including every 1 degree increment within this range.

The data acquisition system 200 (e.g., the data acquisition device 201, a user's device, and/or a remote server) can determine whether the data acquisition device 201 is properly or improperly positioned by analyzing the pressure readings of the one or more pressure sensors. The data acquisition system 200 can assess the quality of the data signals from the data acquisition modules 218 to ensure proper stability and contact of data acquisition modules 218 is occurring to ensure high quality data is being obtained by the data acquisition device 201. If properly positioned, the data acquisition device 201 can automatically begin collecting data (e.g., immediately or after one or more additional conditions are satisfied). The data acquisition device 201 can collect data when not positioned properly, however, some of the data may have accuracy, precision and/or reliability issues, or some of the data may be missing altogether (e.g., pulse oximetry data). The data acquisition system 200 can notify the user that the data acquisition device 201 is not positioned properly. Additionally or alternatively, the data acquisition system 200 can be configured to determine whether the data acquisition device 201 is properly positioned by measuring the voltage drop across one or more sensors of the data acquisition modules 218).

The data acquisition device 201 can begin collecting data when one or more conditions are satisfied (e.g., 1 to 5 or more conditions). The data acquisition device 201 can begin collecting data when a proper position is detected. The data acquisition device 201 can begin collecting data when the data acquisition system 200 detects that the user is in a sleeping position and/or when the user is in a sleeping location, for example, for a predetermined amount of time (e.g., immediately (no time), or after 1 min to 5 min or more have elapsed). The sleeping location can be established or otherwise settable by the user. For example, the data acquisition device 201 can begin collecting data after first, second, third, and/or fourth conditions are satisfied. The data acquisition device 201 can begin collecting data immediately after any one condition or combination of conditions is satisfied. The first condition can correspond to correct device placement (e.g., of the data acquisition device 201). The second condition can correspond to user input (e.g., selection of a command prompt). The third condition can correspond to a position of the device relative to the environment, for example, whether the orientation of the data acquisition device 201 is in a position indicative of a sleeping position of the user (e.g., lying down, either prone, supine, or on side). The fourth condition can correspond to a location of the user (e.g., on a bed). Sleep data collection can begin when the pressure sensors detect that the data acquisition device 201 is properly attached to a head or when the data acquisition modules 218 begin collecting data.

The data acquisition device 201 can have one or more temperature sensors (e.g., 1, 2, 3, 4 or more temperature sensors) configured to monitor a user's body temperature. The temperature sensors can be temperature transducers (e.g., thermocouples). The temperature sensor can be attached to or integrated with the data acquisition device 201. The temperature sensors can be configured to detect when the data acquisition device 201 is attached to a head, for example, by detecting a body temperature. An environment temperature sensor can be configured to measure environmental temperature. The environment temperature sensor can be one of the temperature sensors of the data acquisition device 201. The environment temperature sensor can be a temperature sensor of a sleeping location (e.g., house or apartment). The data acquisition system 200 can determine a user's optimum sleeping temperature and suggest a sleeping temperature for the user, for example, from about 60 degrees Fahrenheit to about 85 degrees Fahrenheit, including every 1 degree increment within this range.

The data acquisition system 200 (e.g., the data acquisition device 201 and/or the data acquisition modules 218) can have one or more accelerometers (e.g., one accelerometer). The accelerometer can be attached to the data acquisition device 201 or can be wirelessly connected (e.g., located at the subject's wrist, finger, or other location). In some aspects, the accelerometer can detect limb movements of the subject. The accelerometer can detect a user's positional state, for example, a user's movement. The accelerometer can be a two-axis accelerometer. The accelerometer can be a three-axis accelerometer. The accelerometer can be configured to detect head, body, and/or limb movements, or any combination thereof. The accelerometer can be used to detect lack of movement as well, for example, the length of time in a single position without movement or with movement within a specified tolerance (e.g., voltage level or movement amount, for example, 5 cm or less).

The electronics modules (e.g., data acquisition modules 218) can include, for example, three channels of frontal EEG and one EEG reference sensor to detect brain wave activity, a heart rate sensor to monitor cardiac activity (e.g., RR variability), an accelerometer (e.g., two or three axis accelerometer) to detect head, body, and/or limb movements, or any combination thereof.

The electronics module 218 can be configured to contact a user's skin (e.g., a user's forehead) during use. The data acquisition device 201 can press the EEG sensors and/or ECG sensor(s) against the user's skin (e.g., forehead) when secured to the head 208, for example, with an elastic fit or with an interference fit. Alternatively or additionally, the sensors can be adhered to the user's skin (e.g., forehead) using an adhesive with or without the data acquisition device 201.

The electronics module 218 can be configured to measure brain activity, for example, during light sleep, during rapid eye movement (REM) sleep, during slow-wave sleep (SWS) (also referred to as deep sleep), or any combination thereof. The electronics module 218 can be configured to measure cardiac activity, for example, HRV such as RR intervals. The electronics module 218 can be configured to detect a user's motion and/or a user's lack of motion.

The electronics module components (e.g., channels, sensors, accelerometers) can be attached to or integrated with the data acquisition module 218. The data acquisition module 218 can be permanently attached to, removably attached to, or integrated with the data acquisition device 201 (e.g., to and/or with the body 214). Additionally or alternatively, the various activity-measuring components (e.g., channels, sensors, accelerometers) can be attached to or integrated with an attachment portion of the data acquisition device 201, for example the body 214 separate and apart from the module 218. The module 218 can be interchangeable with one or more other modules (not shown) having a different number of sensors, one or more different types of sensors, or otherwise having at least one different parameter-measuring capability relative to the electronics module 218. The module 218 can be interchangeable with another module having the same exact module or otherwise with another module having the same exact parameter-measuring capabilities. Different modules 218 can have different sizes relative to one another. Different modules 218 can have different shapes relative to one another.

The data acquisition device 201, a user device, and/or a remote server can analyze the sleep data collected, as described in further detail below. The data acquisition device 201, the user device, and/or a remote server can determine one or more parameters from the data collected, for example, using one or more programmable processors. The parameters can include total light sleep, total SWS (also referred to as total deep sleep), total REM sleep, total non-REM sleep (total light sleep and total SWS added together), total sleep (total REM and non-REM sleep added together), longest deep sleep duration, deep sleep amplitude, strength of deep sleep, heart rate, heart rate variability, total time in bed, time to fall asleep, time awake between falling asleep and waking up, various sleep microstructure features (e.g., number of sleep slow oscillation (SO) events described in further detail below), or any combination thereof. The time-based parameters (e.g., the "total," "duration," and "time" parameters) can be measured in the time domain, for example, using seconds, minutes, hours. Days, weeks and years can be used for accumulated and/or running totals.

The total time in bed parameter can be measured from a start point to an end point. The start point can correspond to when the user manually activates the data acquisition device 201, for example, by selecting a start instruction (e.g., "ready to sleep") on the display 22. The start point can correspond to when the data acquisition device 201 is activated (e.g., automatically or manually). The data acquisition device 201 can be automatically activated, for example, when a voltage is detected across two or more sensors of the module 218 (e.g., across two or more of the EEG electrodes). The voltage can indicate contact with skin and cause the data acquisition device 201 to begin measuring the total time in bed. The data acquisition device 201 can have a timer. The data acquisition device 201 can be automatically activated when positioned on the head 208 as a result of one or more pressure sensors exceeding a pressure threshold. The end point can correspond to when the user manually deactivates the data acquisition device 201, for example, by selecting an end instruction (e.g., "turn off alarm" or "get sleep report") on the display 22. The end point can correspond to when the device is automatically deactivated. The data acquisition device 201 can be automatically deactivated, for example, when the accelerometer indicates the user is walking around or has taken the data acquisition device 201 off their head.

The data acquisition system 200 can provide audio stimulation (also referred to as audio entrainment) using, for example, one or more sound wave generators 217 (e.g., 1 to 4 sound wave generators). The sound wave generators can be, for example, speakers. A portion of the data acquisition device 201 can be positionable over and/or engageable with a left and/or right ear of a user such that the sound wave generators 217 can emit sound into a user's ears. The sound wave generators 217 can be attached to, embedded in, or integrated with the device body. The sound wave generators 217 can be in wired or wireless communication with the data acquisition device 201, a user device, a remote server, or any combination thereof. The sound wave generators 217 can be micro speakers.

Additionally or alternatively, the data acquisition system 200 can provide audio stimulation via bone conduction by transmitting sound signals through bone to a user's inner ear. The data acquisition system 200 can have one or more actuator assemblies 213 to provide bone conduction sound transmission. The actuator assemblies 213 can have an actuator (e.g., a transducer). The actuator can be vibratable (e.g., the actuator can be configured to vibrate). The actuator assemblies 213 can have a transceiver coupled to the actuator. The transceiver can cause the actuator to vibrate to generate sound, for example, when the transceiver is electronically driven with sound signals (e.g., from a driver and/or a controller, for example, from the data acquisition device 201). The actuator can be a piezoelectric actuator. The piezoelectric actuator can be configured to move a mass to provide sound through bone. The actuator assemblies 213 (e.g., the actuator) can be positioned near the ear and/or on the cheek. For example, the actuator assemblies 213 can be positioned on a user's skin proximate the zygomatic bone, the zygomatic arch, the mastoid process, or any combination thereof. The data acquisition system 200 can have 1 to 6 actuator assemblies, or 1 to 6 actuators, including every 1 actuator assembly/actuator increment within these ranges.

The data acquisition system 200 can provide visual/optical stimulation (also referred to as light entrainment) using, for example, one or more light emitting sources 219 (e.g., 1 to 20 light emitting sources). A portion of the data acquisition device 201 can be positionable over and/or engageable with a left and/or right eye of a user such that the light sources 219 can emit light into a user's eyes (e.g., through the user's closed eyelids). The data acquisition device 201 can be configured to partially or completely cover one or both eyes. The data acquisition device 201 can be configured for temporary securement above or proximate to a user's eyes/eyelids. For example, a portion of the data acquisition device 201 can be configured to rest against and/or adhere to an eyebrow, the area proximate an eyebrow, the glabella, the nose (e.g., dorsal bridge, dorsal base, tip), cheek, or any combination thereof. The light sources 219 can be attached to, embedded in, or integrated with the data acquisition device 201.

The data acquisition system 200 can provide audio entrainment, optical entrainment, cranial electrotherapy stimulation (CES), or any combination thereof, in addition to or in lieu of the data collection and associated analyses described below.

Figure 3:
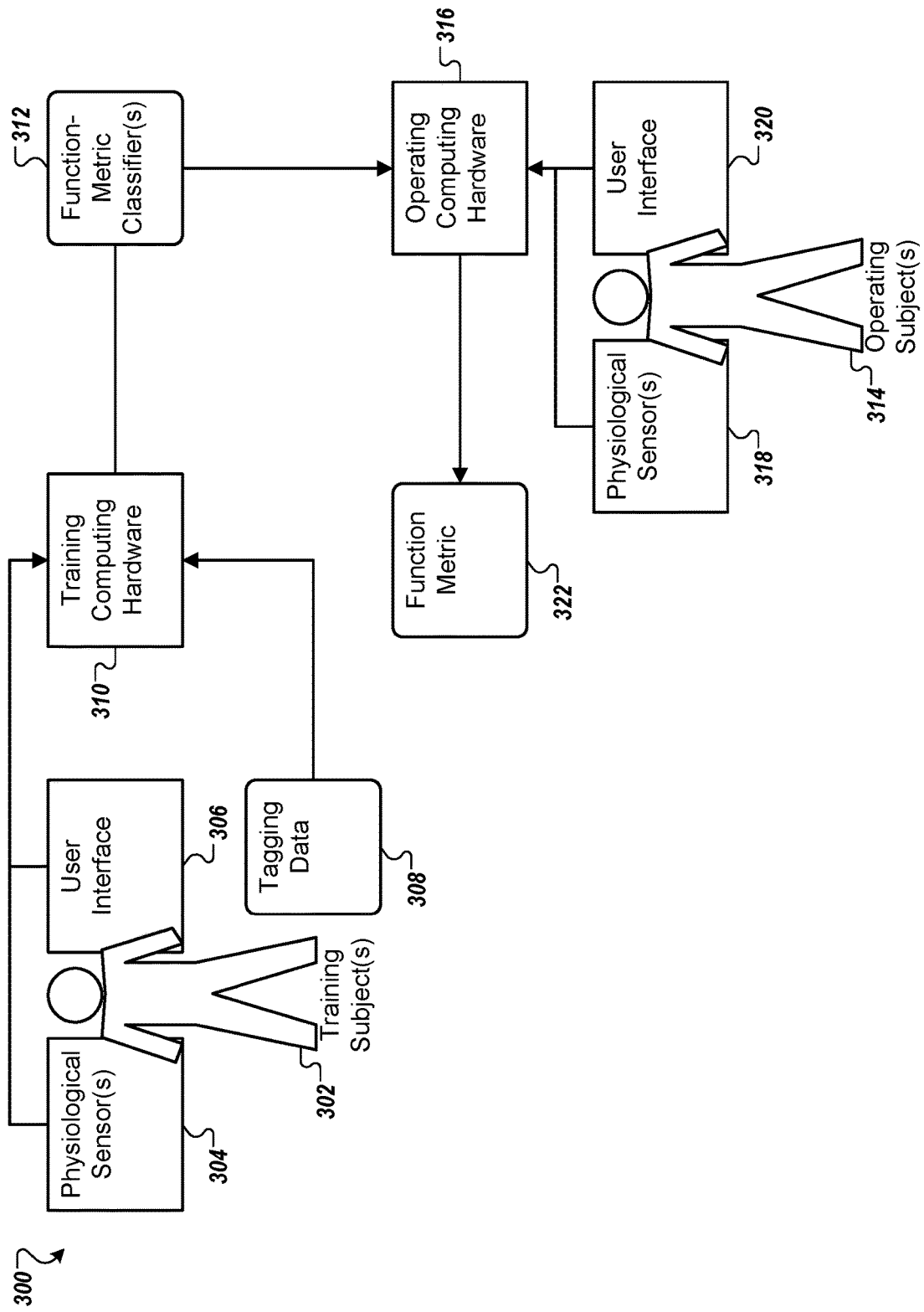
FIG. 3 shows an example system for determining metrics of a subject.

FIG. 3 shows an example system 300 for determining metrics of a subject, such as a brain age or a brain health score for a user of a head-worn sensing device (e.g., data acquisition device 201) as previously described. In this system, one or more training subjects 302 provide training data through physiological sensors 304 and user interfaces 306 (either directly or by another user such as an administrator or health-care provider), which can be combined with tagging data 308 by training computing hardware 310 to generate one or more function-metric classifiers 312. Operating subjects 314 can then use operating computing hardware 316 to collect data through physiological sensors 318 and/or user interfaces 320 to generate one or more function metrics 322.

Training subjects 302 are a group of subjects (e.g., human or other animals) that contribute data to be used as training data. For example, the subjects 302 may be patients who, under a program of informed consent, provide some of their medical records for research purposes. In another example, the subjects 302 may be generally healthy representatives of a population that have agreed to contribute training data. The training subjects 302 may be organized by physiological (e.g., healthy vs having a known medical issue, menopausal status, menstrual cycle phase), demographic details (e.g., age, gender, geographic location, location of residence, education level, professional level), and/or groups based on lifestyle factors (e.g., activity level, past or current behaviours). Thus, classifiers 312 may be created for the population as a whole, or for particular subpopulations (e.g., stratified by health status, age, or other factors expected to impact the operation of the classifiers). In some cases, each classifier 312 may be personalized, using a single subject 302 to create or modify a classifier, where the training subject 302 is also the operating subject 314 so that their personal classifier is used later in operation.

Physiological sensors 304 include one or more sensors that can sense one or more physiological phenomena of the subjects 302. In some cases, the sensors 304 can include sensors mounted in a head-worn device such as the data acquisition modules 218 of the data acquisition device 201 and the physiological sensors 104 of the data acquisition device 101. However, other arrangements are possible such as bespoke training sensors used only for the collection of training data, or use of data collected with other sensors for other purposes (e.g., use of some of, but not all, data generated in clinical sleep studies).

The user interface 306 can include hardware and corresponding software to present user interfaces to a user (e.g., subject 302 or another user) to collect data about the subject 306. This can include the demographic data described, can present information to the subject 302 about the use of data collected and aid in the development of informed consent, etc. The user interface 306 can include a personal computing device such as a desktop or laptop, a mobile computing device such as a phone, tablet, raspberry pi or other appropriate elements for user input and output.

Tagging data 308 includes data that annotates data from the physiological sensors 304 and/or the user interface 306. For example, a user (shown or not shown) and/or an automated system (shown or not shown) can annotate data from the physiological sensors 304 to mark the subject 302 as in states such as sleep-states. These tags in the tagging data 308 can also include other data that can be used in the creation of the classifiers.

The training computer hardware 310 can receive the tagging data 308, data from the physiological sensors 304, and/or data from the user interface 306 to generate one or more function-metric classifiers 312. Example processes for such classifier creation are described in greater detail elsewhere in this document. The classifier 312 can, given a particular set of inputs, generate one or more functional metrics. These functional metrics can include values that give an indication of the state and/or processes of training subjects 302 while they are being monitored with the physiological sensors 304. One example functional metric is brain age, which can include an indication of a subject's brain function as compared to their expected brain function based on their chronological age and functional metrics acquired from a plurality of subjects, though other types of metrics can be created. Another example functional metric is sleep quality and sleep quality related metrics such as an amount of slow wave sleep (SWS), stress recovery (e.g., pre-sleep stress level and post-sleep stress level). Slow-wave sleep (SWS) can be referred to as deep sleep, and can include stage three of non-REM sleep. SWS can include both stage 3 non-REM sleep and stage 4 non-REM sleep. SWS can include one of stage 3 non-REM sleep and stage 4 non-REM sleep.

Later, after the classifier has been created, one or more operating subjects can use the physiological sensors 318 and/or user interface 308 to provide new data to the operating computing hardware 316. The computing hardware can use this new data with the classifier 312 to create new functional metrics for the operating subjects. Said another way, the users 314 can wear a headband (e.g., data acquisition device 201) to bed as previously described, and they can be presented with a brain age or other metric created from one sleep session or from a group of sleep sessions (e.g., a weeks' worth of sleep). As will be appreciated, this can advantageously provide the users 314 with the ability to assess their functional metrics in a single night's sleep or over multiple nights' sleep to provide a short-term result based on a single night's sleep or a longer term result based on multiple nights' sleep data that can be compared to identify trends, changes over time, and can be aggregated to mitigate the night-to-night variability in values of the measured physiological phenomena. The users 314 can also be provided with assessments that are consistent with early signs of cognitive decline.

For example, an otherwise healthy user 314 can use a sleep wearable (e.g., data acquisition device 201) to assess their cognitive function periodically to assess their brain function. The user 314 could use the sleep wearable over the course of several years where they exhibit a normal brain age progression. The user 314 could all of the sudden see a dramatic increase in their brain-age progression. Even without other symptoms, they can then go to their doctor, who can run clinical sleep-study or conduct an MRI scan to discover one or more early developing signs of neurodegenerative diseases and/or neurodegenerative disorders.

Additionally, the determined brain age from the system 300 can be obtained and provided to the subject 314 when the subject is in their normal sleep environment (e.g., at home). This provides data to the user when they are not disturbed by anxiety, not in a comfortable bed or familiar environment, or other factors that would impact their ability to sleep normally. The system 300 does not involve a technician installing multiple uncomfortable leads on the subject 314 which can be advantageous for the subject 314 because the system 300 is much more accessible as well as being more time and cost effective than a sleep-study or other brain function tests that take place in a clinical environment that can include several leads attached to a subject that can have an impact on the subject's ability to achieve sleep results that are representative of the subject's normal sleep results. Additionally, the system 300 can be self-administered by the subject, without the intervention of a technician, while a sleep-study and a MRI include the intervention of a technician to assist in the testing protocol. The system 300 can provide a self-diagnostic test that provides the subject with a functional result that a sleep-study or MRI could not provide.

The system 300 can also be used to monitor effectiveness of clinical or wellness interventions. For example, the system 300 can assess if a medication, drug, or other intervention slowed the progression of brain age for the subject 314. The system 300 can assess if taking up meditation, improving sleep hygiene, exercising, or joining peer groups have an impact on the progression of brain age. The system 300 can assess if a combination therapy (e.g., administration of a drug Along with digital health intervention) has a greater impact on brain age than the impact of each individual intervention. The system 300 can provide auditory stimulation of sleep slow oscillations and assess the impact of the auditory stimulation on slow-wave sleep. In some aspects, the system 300 can assess the potency of a drug, the effectiveness of a vaccine, and an immune-response of a subject. In some aspects, the system 300 can be utilized in interventions related to behavioral and lifestyle changes including the reduction or elimination of tobacco (or other drug) consumption, changing eating habits, changing drinking habits, activity level, among others.

Figure 4:
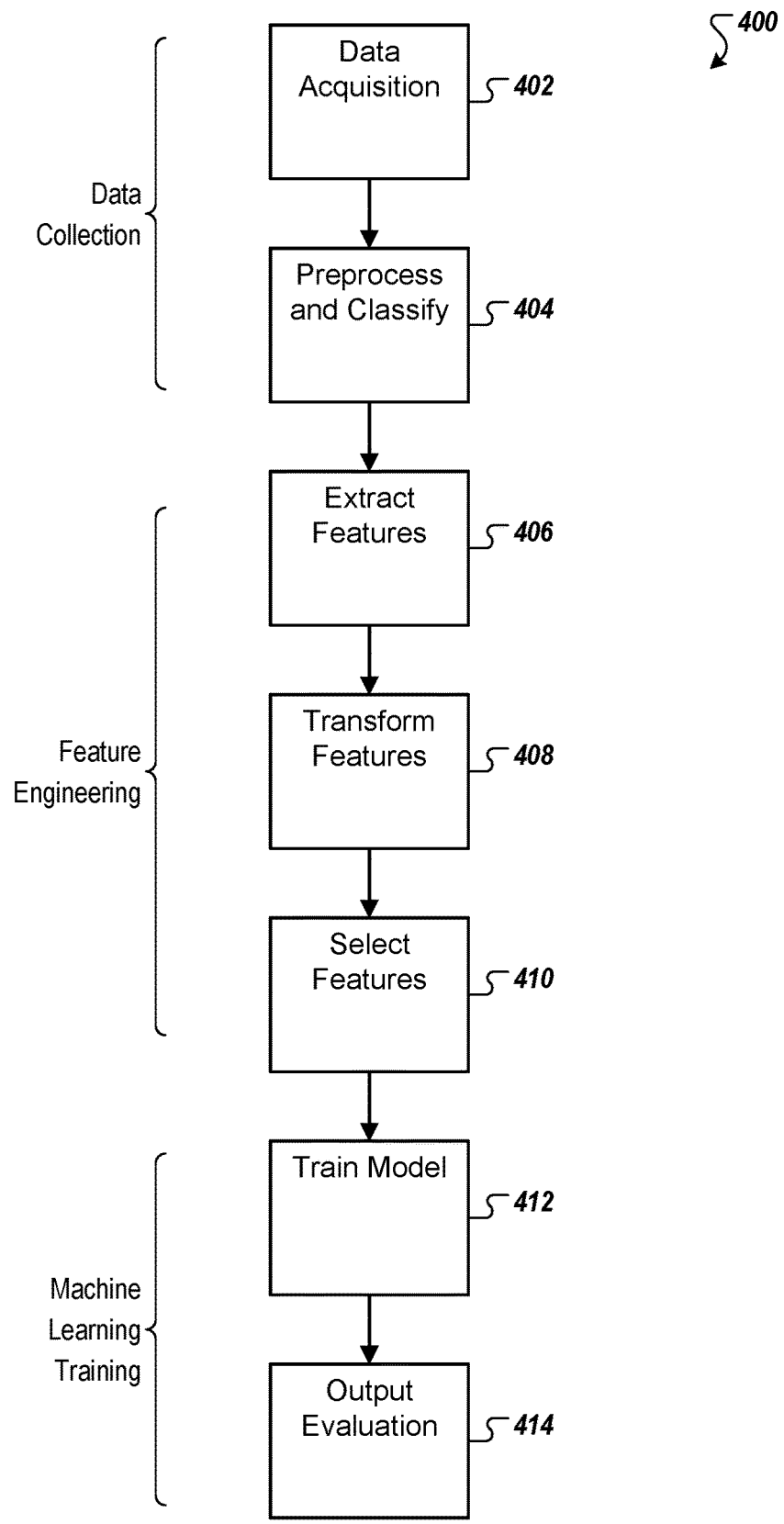
FIG. 4 shows an example process that can be used to produce classifiers able to evaluate subject data and generate function metrics.

FIG. 4 shows an example process 400 that can be used to produce classifiers that are able to evaluate subject data (e.g., sleep data) and generate functional metrics (e.g., brain age or brain health). For example, the process 400 can be performed by the elements of the system 300 and will be described with reference to those elements. However, other systems can be used to perform the process 400 or similar processes.

Generally speaking, the process 400 includes data collection 402-404, feature engineering 406-410, and machine learning training 412-414. In the data collection 402-404, data is gathered in formats in which it is generated or transmitted, then reformatted, decorated, aggregated, or otherwise processed for use. In the feature engineering 406-410, data is analyzed to find those portions of the data that are sufficiently predictive of a physiological function (e.g., brain function) to be used to train the classifiers. This can allow the discarding of extraneous or unneeded data, improving computational efficiency and/or accuracy. The machine learning training 412-414 can then use those features to build one or more models that characterize relationships in the data for use in future classifications.

In the data acquisition 402 for example, the computing hardware 310 can collect data from the sensors 304, from the user interface 306, and the tagging data 308. As will be understood, this acquisition may happen over various lengths of time and some data may be collected after other data is collected.

In the preprocessing and classifying 404 for example, the computing hardware 310 can perform operations to change the format or representation of the data. In some cases, this may not change the underlying data (e.g., changing integers to equivalent floating point numbers, marking epochs of time in time-series data), may destroy some underlying data (e.g., reducing the length of binary strings used to represent floating point numbers, applying filters to time-series data), and/or may generate new data (e.g., averaging two frontal EEG channels such as Fp1 and Fp2 to create a single, virtual prefrontal EEG signal; mapping annotations to the data).

In the feature extraction 406 for example, the computing hardware 310 can extract features from the processed and classified data. Some of these features can be related to sleep macrostructure, i.e. the decomposition of a sleep session into sleep stages (e.g., information about the proportion of sleep spent in a particular stage and the number of transitions between different sleep stages). Some of these features can be related to sleep microstructure, i.e. information about a sleep session based on the detection and analysis of specific waveforms and frequency components of the acquired data (e.g., number of SO events, information related to sleep spindles and SO-spindle coupling, averages of various EEG frequency components within a sleep stage, like average delta band (0.5-4 Hz) power during SWS or strength of deep sleep). Some of these features can be related to cardiac activity (e.g., heart rate, heartrate variability (HRV)). Some of these features can be related to respiratory activity and/or blood oxygenation (e.g., apnea-hypoxia index (AHI)). Some of this data can be related to stimulus-response activity (e.g., response by the subject to light, sound, electricity, or other stimulus including while asleep). Additionally, sleep microstructure features can include total numbers and stage-specific densities (i.e., number of events during a specific sleep stage divided by total duration of a specific sleep stage) of Sos, fast spindles, slow spindles, early-fast spindles, and late-fast spindles. Sleep microstructure features can include—Averages, standard deviations, and other statistical descriptives of SO morphological features (e.g., SO peak-to-peak amplitude, SO duration, SO negative peak amplitude). Sleep microstructure features can include averages, standard deviations, and other statistical descriptives of spindle features (e.g. spindle frequency, spindle duration, spindle amplitude). Sleep microstructure features can include averages, standard deviations, and other statistical descriptives of SO-spindle coupling features (e.g. relative SO-spindle phase, overlap between a spindle event and the SO up-phase), among other microstructure features and other microstructure feature combinations.

In the feature transformation 408 for example, the computing hardware 312 can modify the features in ways that preserve all data, destroy some data, and/or generate new data. For example, values may be mapped to a given scale (e.g., mapped to a log scale, mapped to scale of 0 to 1). In some cases, statistical aggregates can be created (e.g., mean values, standard variation). These aggregates may be generated from data for each sleep session, across the detected sleep stages, or may aggregate data across multiple sleep sessions.

In the feature selection 410 for example, the computing hardware 312 can select some of the features for use in training the model. This can include selecting a proper subset (e.g., some, but not all) of the features.

In the model training 412 for example, the computing hardware 312 can train one or more machine-learning models using the selected features. In some cases, one or more models are created that propose mappings between the features and tagged data indicating brain age for those features. Then, the computing hardware 312 modifies those mappings to improve the model's accuracy.

In the output evaluation 414 for example, the computing hardware 312 can generate one or more functions, sometimes called classifiers, which include a model. This inclusion can involve including the whole model, or may involve only including instructions generated from the model allowing for the classifier to have a smaller memory footprint than the model itself.

Described now will be one example implementation of the process 400. While a particular number, type, and order of details are selected for this implementation, it will be understood that other numbers, types, and order of details may be used to implement the process 400 or other processes that accomplish the same goals.

In the data acquisition 402 in this implementation, basic information about a subject can be acquired such as one or more of a subject's: name or identification (ID), age, gender, other sociodemographic data, health-related information, physiological information (e.g., menopausal status and menstrual cycle information), and information related to lifestyle or behaviors (including but not limited to sleep habits, tobacco/alcohol consumption, exercise, meditation, among others). This data can be user inputted or integrated from other devices.

The system(s) described above can enable the real-time open-loop or closed-loop delivery of stimuli, which include at least one or more of audio, light, vibratory, or electrical stimuli, as part of the data acquisition procedure.

The subject's raw biological information can be collected, which can include of at least one or more sleep recordings where each recording includes at least one frontal EEG channel and can include additional sensors such as: additional EEG channels, forehead PPG, blood oxygen saturation ($SpO_2$), EMG, EOG, EDA, and actigraphy (movement) sensors. In some cases, systems can use two frontal EEG channels (Fp1 and Fp2), with or without PPG, $SpO_2$, and actigraphy. The data can be collected from full night recordings and/or less-than full nights (e.g., naps).

The output of the data acquisition 402 can include each subject's raw biological signals and stimulus types and timings, from one or multiple recordings, as well as the subject's age and other basic information.

In the preprocessing and classifying 404 in this implementation, preprocessing and automated sleep-stage classification can include various operations that may be performed on the output of the data acquisition 402. For example, two bandpass-filtered (0.2-40 Hz) frontal EEG signals are averaged to obtain a single virtual frontal EEG channel. Heartbeat times are extracted from the filtered and demodulated PPG signal using peak detection.

The data is segmented into discrete overlapping and/or non-overlapping epochs and each epoch is described using a set of time-domain, frequency-domain and other EEG features typically used for sleep stage classification. Each epoch is classified as either wakefulness (W), rapid eye movement (REM) sleep, non-REM sleep stage 1 (N1), non-REM sleep stage 2 (N2), or deep sleep (N3), using an automatic sleep stage classification algorithm based on machine learning (ML) and the extracted sleep EEG features.

Manually annotated sleep stages can be used from a PSG database, but other implementations can use automatically-scored stages. The sleep stage classification algorithm may or may not use actigraphy and HRV data in addition to EEG data.

The output of the preprocessing and classifying 404 can include each subject's preprocessed biological data, from one or multiple recordings, segmented into time-based epochs. For example, the time-based epochs can be segmented into 10-second, 20-second or 30-second epochs, where each epoch is annotated by a sleep stage, or with probabilities of belonging to each of the possible sleep stages (i.e. softmax output).

In the feature extraction 406 in this implementation, sleep macrostructure features are computed. These macrostructure features are related to stage durations/percentages, stage transition probabilities, and fragmentation or awakenings. In an implementation where neural-network-based sleep stage probabilities (i.e. hypnodensity diagram) are available for each epoch, macrostructure features can include hypnodensity-based features, e.g. the maximum probability of wakefulness in a recording, or the maximum value of the product between the N2 and REM probability in a recording.

From the full preprocessed EEG signal, and the obtained sleep stage annotations, EEG-based stage-specific sleep microstructure features are computed. The microstructure features include stage-specific EEG features such as stage-specific averages, std deviations, and other statistical descriptives of the time-domain, frequency-domain and other EEG features.

From the full preprocessed EEG signal, and the obtained sleep stage annotations, waveform-specific EEG based microstructure features are created, related to slow oscillations (Sos), sleep spindles, SO-spindle coupling and density, and other EEG waveforms relevant in the context of aging. From the full preprocessed EEG signal, and the obtained sleep stage annotations, stimulus-response-related EEG features are created which are calculated by analyzing the EEG responses to stimuli which include at least one or more of audio, light, vibration, or electrical stimulation, which are delivered through the headband either in open-loop or in closed-loop while the subject is asleep.

From the obtained heartbeat times, and the obtained sleep stage annotations, an array of both stage-specific and general heart rate variability (HRV) features are computed, based on time-domain, frequency-domain and nonlinear HRV analysis. From the collected 402 data, and the obtained sleep stage annotations, time-domain features related to blood oxygenation and sleep apnea are computed.

Some implementations use just sleep macrostructure features and EEG-based microstructure features (both stage-specific and waveform-specific) and do not use stimulus-response-related EEG features.

The output of the feature extraction 406 can include each of the subject's recordings, either one or multiple, described with an array of sleep macrostructure, as well as EEG-based, HRV-based and $SpO_2$-based sleep microstructure features. Total number of features can be labeled $M_{full}$.

In the feature transformation 408 in this implementation, the computed features are transformed using a log-based transformation, in order to remove skewness in the feature distributions. For subjects with multiple recordings, each feature value is determined as the mean feature value across either all or a subset of the available recordings. Based on the dates of specific recordings, and recording quality assessment (outlier detection), the process determines which recordings to include in calculating the mean feature values. Additionally, when multiple subjects with multiple recordings are available, new features related to night-to-night variability in specific sleep features can be used as inputs to the BA model (e.g. std deviation of a given features across multiple recordings for the given subject). Alternatively, instead of averaging the features for subjects with multiple recordings, final estimate of the subjects' physiological metric (e.g. brain age) can be determined as the mean estimate of the subjects' physiological metric based on either all or a subset of the available recordings.

In some cases, just one full night's recording per subject is used. In some cases multiple night's recordings are used with feature averaging as the subject wears the headband for multiple nights or sleep sessions.

The output of the feature transformation 408 can include data for each subject described with $M_{full}$ transformed sleep macrostructure and microstructure features, which are based on either one or multiple recordings.

In the feature selection 410 in this implementation uses a sequential feature selection algorithm, or the "Maximum Relevance Minimum Redundancy" (MRMR) feature selection algorithm, and the available training data, to select a subset of features to be included in the final feature set. The criterion used to determine the optimal feature set is the cross-validated mean absolute error (MAE) in predicting the subjects' chronological age (CA). An example of the machine learning (ML) algorithm that can be used is the extreme learning machine (ELM) regressor with one or more hidden layers and the option of a functional link. At each iteration of the sequential feature selection algorithm, the average of a repeated k-fold cross-validated MAE is determined. The model hyperparameters are optimized using a Bayesian optimization algorithm. At each iteration of the cross-validation procedure, features are normalized using mean and std. deviation values which are determined based on data from the train folds. For example, gradient boosted trees, Minimum Redundancy Maximum Relevance (mRMR) techniques may be used. However, other machine learning or non-machine learning techniques can be used.

In some cases the ELM classifier and sequential feature selection only are used, but other machine learning and feature selection techniques may provide better results based on the particulars of the system and the used training data. For example, other feature selection strategies (such as MRMR) using another error metric such as cross-validated root mean square error (RMSE) may be used and other types of regressions may be used such as other nonlinear regression models such as support vector regression (SVR).

The output for the feature selection 410 can include each training subject, described with $M_{reduced}$ transformed sleep macrostructure and microstructure features, where $M_{reduced} \leq M_{full}$.

In the model training 412 in this implementation, a final set of $M_{reduced}$ features is used to train the prediction model. The model hyperparameters are determined using the Bayesian optimization algorithm, with the goal of optimizing the average model performance in repeated k-fold cross-validation. Multiple approaches are possible: classical regression; regression with a custom loss function based on residual-label covariance analysis; regression with adjustment of the age-dependent bias, a deep label distribution learning algorithm based on neural networks, a cascade of a multi-class classification model (e.g. a support vector machine) followed by several regression models where each is trained for a specific demographic or physiological class (group), etc.

Using the cross-validated BA estimates from an entire dataset, or a relevant subset of the available data, as well as BA estimates obtained in a left-out validation set and the subjects' chronological ages, a regression analysis of potential Brain Age Index (BAI) covariates is conducted. BAI is here defined as the difference between BA and CA. Potential BAI covariates include various demographic, lifestyle, and health-related variables, e.g. gender, race, having a sleep disorder, body mass index, drinking and smoking habits, cardiovascular health variables, psychological health variables, etc. Identification of statistically significant BAI covariates can be used to better inform the user and help provide personalized intervention recommendations In the output evaluation 414 in this implementation, output of the model is evaluated on new subjects. The subject's features are calculated according to steps 402-408, and a set of $M_{reduced}$ predefined features, which were chosen to be most relevant for brain age prediction by the ML part of the algorithm.

The trained brain age model from step 412 outputs a Brain Age estimate or other metric. In some cases, the output of the algorithm includes the estimated brain age. In some cases, a Brain Age estimate for a given subject is determined by averaging algorithm's outputs for multiple recordings from the same subject. In some cases, the output of the algorithm includes a degree of confidence in the output. Based on the number of nights of data, the multi-night variability of the data, and the tightness of the fit with the pre-built normative distribution curves, or any combination thereof, a confidence level is provided for each brain age prediction.

In some cases, the output of the algorithm includes excess brain age, which is the amount or percentage by which brain age exceeds chronological age. For example, the user is provided with an explanation of the output, i.e. model interpretations. Model interpretations are provided using explainable AI (XAI) techniques such as Shapley Additive Explanations (SNAP) and local interpretable model-agnostic explanations (LIME). A predefined number of most important features contributing to brain age excess are shown to the user, each feature in terms of one or more of the following: directionality and strength of contribution to brain age excess, mean feature value, normative distribution of the specific feature adjusted by age, gender, or other potentially confounding factors (e.g., sociodemographic, physiological). Such output can be shown to a medical expert who could propose and guide future interventions aimed at modifying the sleep features which are contributing to the objectively measured brain age excess. Based on model interpretation, and based on the user's demographic, health, lifestyle/behavioral variables, recommendations or tips can be provided to the user. Output to users can be in a variety of forms, including: mobile app, web app, emailed report, and others.

Figure 5:
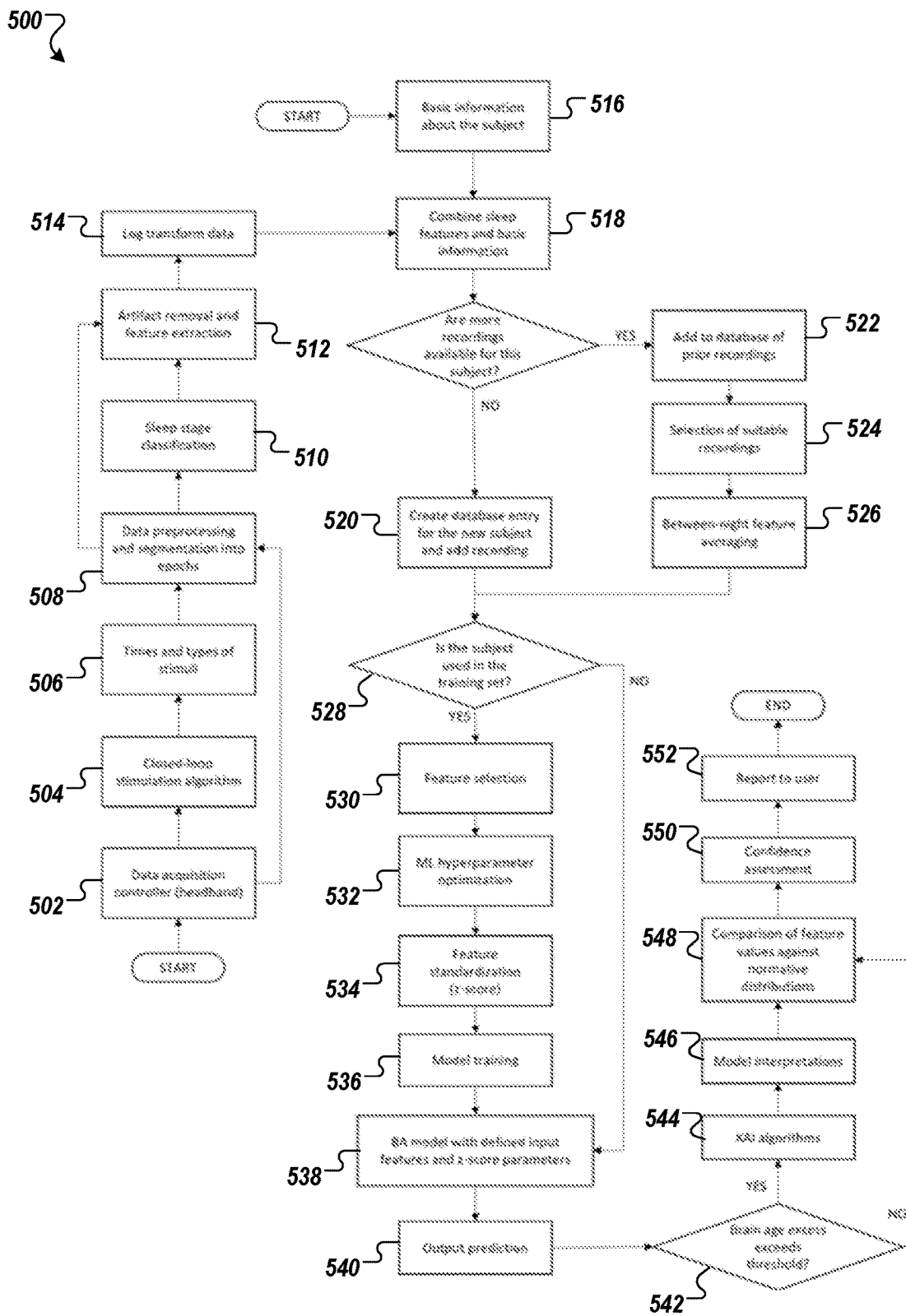
FIG. 5 shows an example process that can be performed by the system.

FIG. 5 shows an example process 500 that can be performed by the system 300. In the process 500, data is acquired 502 e.g., through a headband. A closed-loop stimulation algorithm is executed 504 to provide a subject with stimulation. Times and types of stimuli are recorded 506. Data is processed and segmented into epochs 508. Sleep stages in the data are classified by using an automated sleep stage classification algorithm 510. Artifacts are removed in the data and features are extracted 512. A log transformation is applied to at least some of the features 514. Basic information about the subject is collected 516. Sleep features and basic information are combined 518. If more recordings for the subject are available, they are added to a database of prior recordings 522. Suitable recordings are selected 524. Between-night features are averaged 526. If more recordings for the subject are not available, a new database entry is created for the new subject and the recording is added 520. It is determined if the subject is used in the training set 528. If the subject is in the training set, features are selected 530. Machine learning hyperparameters are optimized 532. Features are standardized 534. One or more models are trained 536. A brain age model is created with defined input features and z-score parameters 538. If the subject is not in the training set, an output is predicted 540. It is determined if the brain age excess exceeds a threshold 542. If the threshold is exceeded an XAI algorithm is executed on the data 544. Model interpretations are created 546. Feature values are compared against normative distributions 548. Confidences is assessed 550. A report is made to a user 552.

Figure 6:
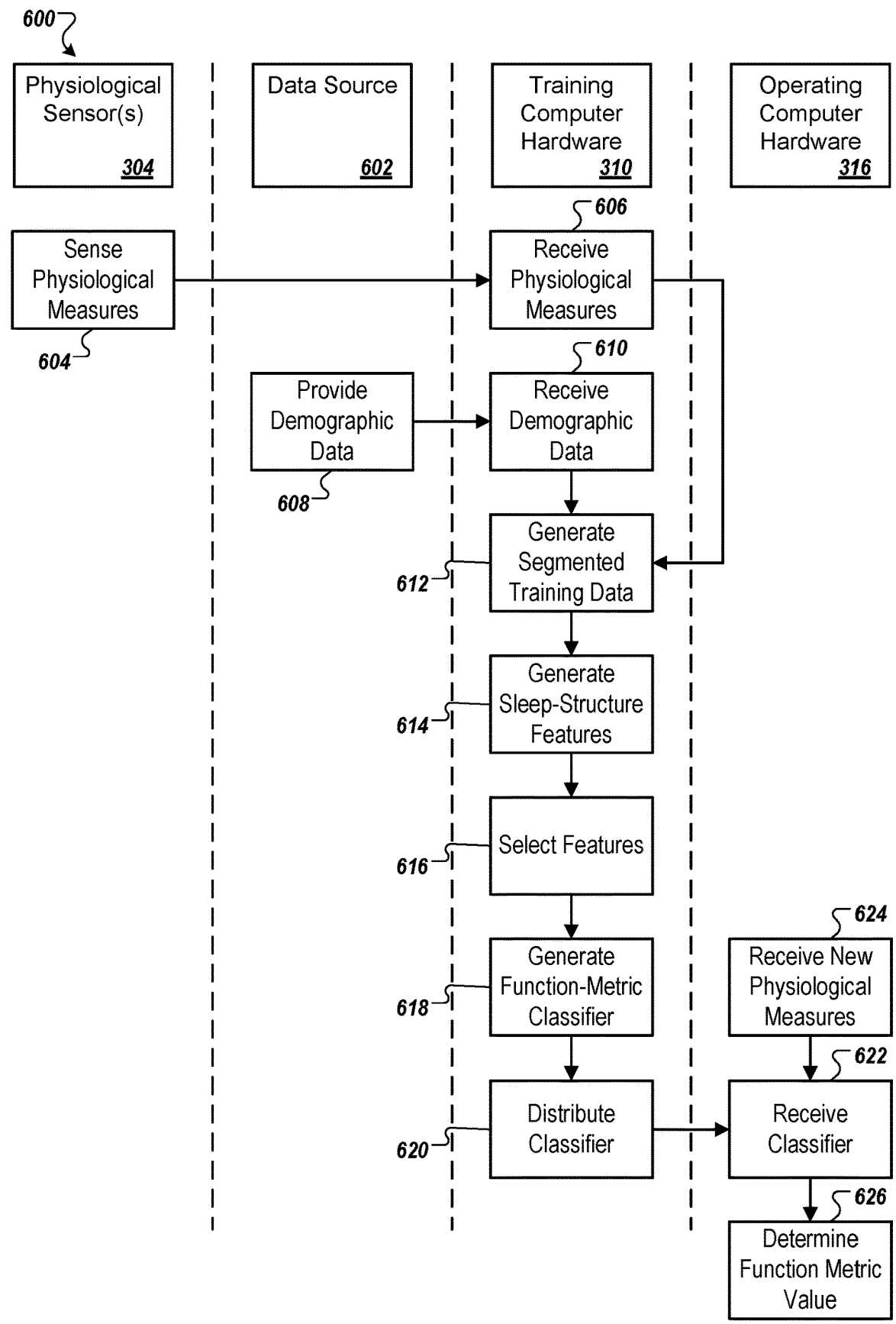
FIG. 6 shows an example process for determining metrics of a subject.

FIG. 6 shows an example process 600 for determining metrics of a subject. The process 600 can be performed, for example, by the physiological sensors 304, a data source 602, the training computer hardware 310, and the operations computer hardware 316, though other components may be used to perform the process 600 or other similar processes.

The sensors 304 sense physiological measures 604 and send the physiological measures to the training computer hardware 310. The training computer hardware 310 receives the physiological measures of the subject recorded at least partly while the subject is asleep. For example, one or more subjects can be sensed to build training data for the process 600. The physiological measures of the subject can include a variety of data, including a frontal electroencephalography (EEG) channel, a prefrontal (Fp) EEG channel, two frontal EEG channels, two prefrontal EEG channels, forehead photoplethysmography (PPG), blood oxygen saturation (SpO2), electromyography (EMG), electrooculography (EOG), electrodermal activity (EDA), and actigraphy data collected, for example, by one or more worn devices that are worn while the subjects sleep.

In some cases, the physiological measures of the subject were recorded at least partly while the subject is asleep. This can include instances where one or more devices provided the subject with at least one stimuli. The type of stimuli can include, but is not limited to, audio stimuli, light stimuli, electrical stimuli, open-loop stimuli, and closed-loop stimuli; and the physiological measures comprising timing info defining timing of stimuli provided to the subject The data source 602 provides demographic data 608 to the training computer hardware 310 and the training computer hardware 310 receives the demographic data for the subject. For example, the data sources 602 may include a database stored in one or more servers connected to the training computer hardware 310 over a data network such as the internet.

In some cases, the demographic data includes a chronological age for the subject when the physiological measures were recorded. This can be recorded, for example, in terms of years, months, days, etc., though other formats are possible. The demographic data can also or alternatively include data for subjects such as an identifier (their legal name, a unique identifier, etc.), a gender, sociodemographic data, health data, behavioral, and/or lifestyle data that have been entered by the subject into an input device.

The training computer hardware 312 generates 612, using the physiological measures and from the demographic data, segmented training-data. The segmented training-data can specify a plurality of epochs of time and data for the subject in each epoch. For example, each epoch may be defined as a time window of 15 seconds, 30 seconds, 1.125 minutes, etc. The epoch may overlap or may be separate such that they do not overlap and may begin at the ending of a previous epoch or after a period of time without an epoch defined.

To generate the segmented data, the hardware 312 can apply one or more band-pass filters to at least some of the physiological measures, e.g., to remove high and low values greater than and less than given thresholds. At least frontal EEG signals can be combined to create a virtual frontal EEG signal. Heartbeat times can be extracted from PPG signals by detecting peaks in the PPG signals. The physiological measures can be separated and/or segmented into a plurality of epochs of time such that each epoch includes the various measures of physiological function that occurred in the subject concurrently. For each epoch of time, features are generated that can include multiple time-domain features, frequency domain features, and other non-linear or complex signal descriptives (e.g., fractal dimension Lyapunov exponent, entropy measures, histogram-based features).

The hardware 312 can use tagging data that tags each epoch of time with a sleep stage. Various schemes for defining sleep stage can be used. In one scheme, the sleep stages are classified as wakefulness, rapid eye movement (REM) sleep, non-REM sleep stage 1 (N1), non-REM sleep stage 2 (N2), and non-REM sleep stage 3 (N3) and could include non-REM sleep stage 4 (N4). In one scheme, the sleep stages are classified as awake, REM, light sleep, and deep sleep. In one scheme, the sleep stages are classified as awake, REM and nREM. In these schemes, an epoch can be tagged as an unknown (not tagged) sleep stage, due to data loss, low data quality, or other reasons which would not allow the proper functioning of the sleep stage classification algorithm.

The training computer hardware 310 generates 614, using the segmented training-data, sleep-structure features for the subject. For example, the features of sleep-structure may conform to common sleep-structure types well known in the community (e.g., number of sleep SO events). In some cases, the features of the sleep-structure may include or only include otherwise-unknown structure types developed for this technology. Sleep-structure features can include, but are not limited to, macrostructure features, microstructure features, physiological features (e.g., cardiac features, respiratory features), and combinations thereof.

Macrostructure features are determined for the subject describing aspects of sleep including, but not limited to sleep-stage duration, sleep-stage percentage, sleep-stage transition probability, sleep fragmentation, and awakenings. Microstructure features are determined for the subject describing aspects of sleep including, but not limited to stage-specific EEG features, waveform-specific EEG features, and stimulus-response EEG features. Cardiac features are determined for the subject describing aspects of cardiac activity including, but not limited to heartbeat times and tagging data that tags epochs of time with sleep stage. Cardiac features can include time-domain, frequency-domain, nonlinear and complex HRV features, as well as stage-specific averages, standard deviations, and other statistical descriptives of those features.

Respiratory features are determined for the subject describing aspects of respiratory activity for the subject including, but not limited to blood oxygenation and sleep apnea, using at least one of the group consisting of blood oxygen saturation (SpO2) data, heartbeat times, and the tagging data. Respiratory features can include respiratory activity and/or blood oxygenation features (e.g. apnea-hypopnea index (AHI), respiratory rate, deoxygenation level), as well as stage-specific averages, standard deviations, and other statistical descriptives of those features.

The training computer hardware 310 selects 616 a subset of the sleep-structure features as selected features. For example, one or more analyses may be performed to identify identifying the subset of the sleep-structure features as those features most predictive of the chronological age of the demographic data.

This selection can include transforming one or more features such as macrostructure features, microstructure features, cardiac features, and respiratory features. In some cases, sleep-structure features can be aggregated from multiple sleep-sessions. In some cases, sleep-structure features are generated from only a single sleep session. To select the features, cross-validated mean absolute error (MAE) (e.g., finding and averaging the difference, without regard to the sign of the differences) with an extreme learning machine (ELM) regressor (e.g., using a feedforward neural network such as those with hidden nodes having parameters that are not tuned), or some other regression model suitable for the task, may be performed.

The training computer hardware 310 generates 618 one or more function-metric classifiers comprising training a model that defines at least one relationship between the physiological measures and the chronological age. For example, the model may predict new results based on old training data. The training can include determining hyperparameters of the model or hyperparameters that control learning processes for a model using a Bayesian optimization algorithm. This optimization algorithm can be configured to target various targets or loss functions, such as a model's performance in repeated k-fold cross-validation. The training can use, for example, a regression; a regression with a loss function based on a residual-label covariance analysis, or a deep label distribution algorithm.

The training can include refining the model reduce age-dependent bias. For example, it may be the case that some implementations may use models that exhibit a mathematical bias (e.g., generation of an output set in which data incorrectly skews, clusters, or oscillates around one or more attractor point in the output space, or that applies an weighting to a parameter or set of parameters that is either greater or smaller than the weighting exhibited by the ground truth) related to age or another demographic criteria. In such a case, the training of the model can include refining or other editing in a way that reduces the bias along this parameter or multiple parameters. This refining can include first identifying a parameter for which the model exhibits bias, then applying one or more modifications to the model and/or model output to reduce or eliminate. For example, it may be determined that the model performs well for users of a given age (e.g., 24 years and older) but less well for younger users (e.g., producing brain age estimates that are too high for users of 0 years to 24 years, with error increasing the closer to 0 years). In such a case, an output-conditioning function can be applied to all outputs or outputs for users of age 24 years or less. One such adjustment includes a linear adjustment (e.g., finding a constant value c, and multiplying that constant value by 24—the age of the subject, and then subtracting this value from the model's initial brain age estimate). However, other adjustments are possible including non-linear scaling.

The training computer hardware 310 distributes 620 the function-metric classifiers to a plurality of user devices (e.g., operating computer hardware 316) that are receive the classifier 622 and are configured to sense new physiological measures of other subjects at least partly while the other subjects are asleep. For example, with this classifier created, a manufacturer of a device such as a headband can include the classifier in the computing hardware of the headband or an application associated with the headband to run on a phone, computer, or other device.

The operating computer hardware 316 receives 624, as input, new physiological measures. For example, a new user may purchase or be given the headband, place the headband on their head, and then go to sleep as normal at night. The hardware 316 can receive, from one or more sensors, new physiological measures of the subject recorded at least partly while the subject is asleep and recorded after the function-metric classifiers have already been generated.

The operating computer hardware 316 provides 626, as output, a function-metric value determined based on the defined relationship between the physiological measures and the chronological age. For example, the user may be provided with a brain age or neurologic activity report showing the functional metric (e.g., brain age or otherwise) on a computer screen, via a mobile application, or in a printed report.

To create this metric for the user, the hardware 316 can submit the new physiological measures to at least one of the function-metric classifiers as the input; and receive as output from the at least one function-metric classifier the function-metric value. In addition to a single metric, the classifier can also provide other types of output including but not limited to a confidence value, a variance-from-chronological-age value, a model interpretation, a human-readable instruction displayable to a user of an output device, and an automation-instruction that, when executed by an automated device causes the automated device to actuate.

Figure 7:
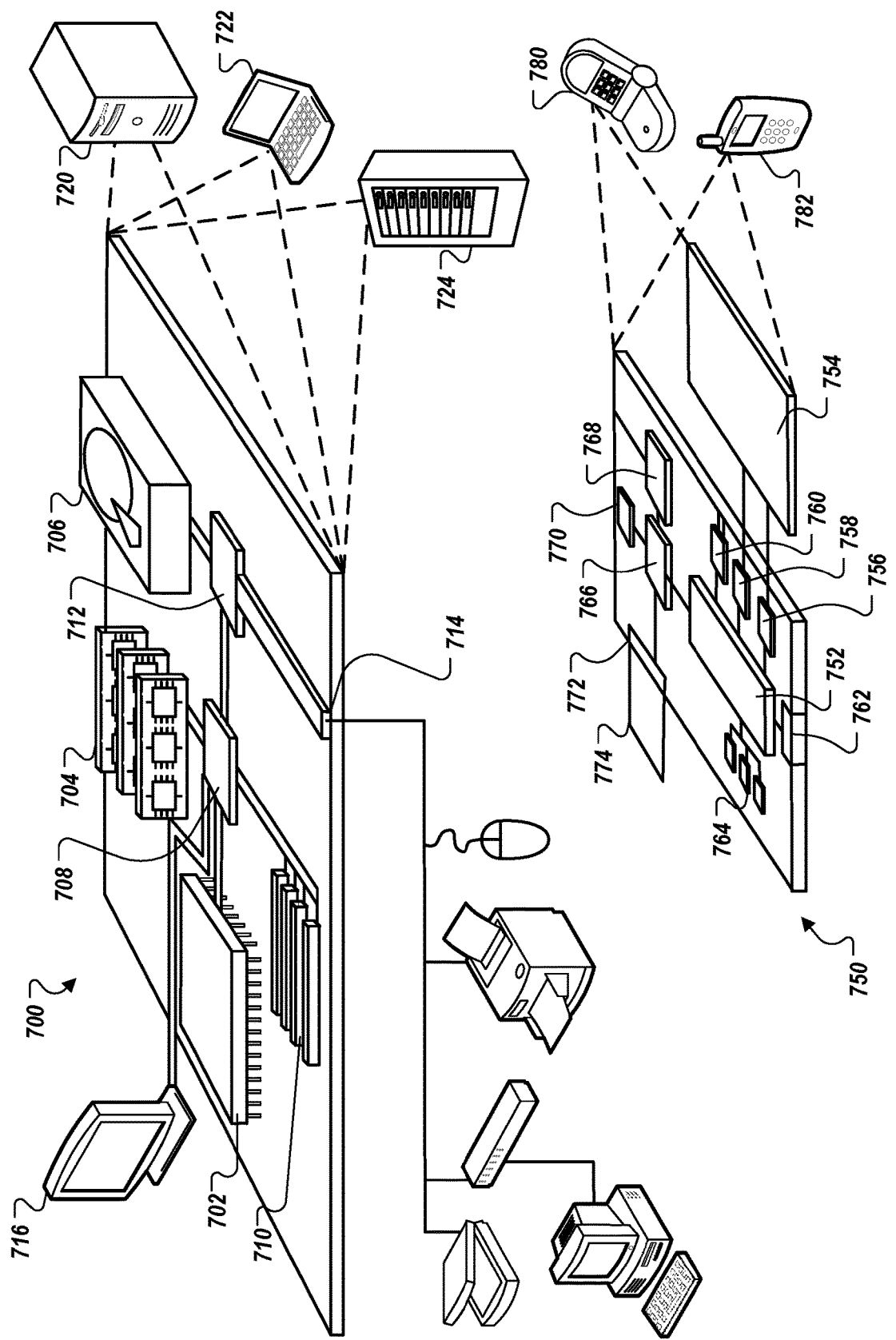
FIG. 7 is a block diagram of computing devices that may be used to implement the systems and methods described in this document, as either a client or as a server or plurality of servers.

FIG. 7 shows an example of a computing device 700 and an example of a mobile computing device that can be used to implement the techniques described herein. The computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 can also be another form of computer-readable medium, such as a magnetic or optical disk.

The storage device 706 is capable of providing mass storage for the computing device 700. In some implementations, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. In some implementations, the high-speed interface 708 is coupled to the memory 704, the display 716 (e.g., through a graphics processor or accelerator), and to the high-speed expansion ports 710, which can accept various expansion cards (not shown). In the implementation, the low-speed interface 712 is coupled to the storage device 706 and the low-speed expansion port 714. The low-speed expansion port 714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. In addition, it can be implemented in a personal computer such as a laptop computer 722. It can also be implemented as part of a rack server system 724. Alternatively, components from the computing device 700 can be combined with other components in a mobile device (not shown), such as a mobile computing device 750. Each of such devices can contain one or more of the computing device 700 and the mobile computing device 750, and an entire system can be made up of multiple computing devices communicating with each other.

The mobile computing device 750 includes a processor 752, a memory 764, an input/output device such as a display 754, a communication interface 766, and a transceiver 768, among other components. The mobile computing device 750 can also be provided with a storage device, such as a micro-drive or other device, to provide additional storage. Each of the processor 752, the memory 764, the display 754, the communication interface 766, and the transceiver 768, are interconnected using various buses, and several of the components can be mounted on a common motherboard or in other manners as appropriate.

The processor 752 can execute instructions within the mobile computing device 750, including instructions stored in the memory 764. The processor 752 can be implemented as a chipset of chips that include separate and multiple analog and digital processors. The processor 752 can provide, for example, for coordination of the other components of the mobile computing device 750, such as control of user interfaces, applications run by the mobile computing device 750, and wireless communication by the mobile computing device 750.

The processor 752 can communicate with a user through a control interface 758 and a display interface 756 coupled to the display 754. The display 754 can be, for example, a TFT (Thin-Film-Transistor Liquid Crystal Display) display or an OLED (Organic Light Emitting Diode) display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can provide communication with the processor 752, so as to enable near area communication of the mobile computing device 750 with other devices. The external interface 762 can provide, for example, for wired communication in some implementations, or for wireless communication in other implementations, and multiple interfaces can also be used.

The memory 764 stores information within the mobile computing device 750. The memory 764 can be implemented as one or more of a computer-readable medium or media, a volatile memory unit or units, or a non-volatile memory unit or units. An expansion memory 774 can also be provided and connected to the mobile computing device 750 through an expansion interface 772, which can include, for example, a SIMM (Single In Line Memory Module) card interface. The expansion memory 774 can provide extra storage space for the mobile computing device 750, or can also store applications or other information for the mobile computing device 750. Specifically, the expansion memory 774 can include instructions to carry out or supplement the processes described above, and can include secure information also. Thus, for example, the expansion memory 774 can be provided as a security module for the mobile computing device 750, and can be programmed with instructions that permit secure use of the mobile computing device 750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 764, the expansion memory 774, or memory on the processor 752. In some implementations, the computer program product can be received in a propagated signal, for example, over the transceiver 768 or the external interface 762.

The mobile computing device 750 can communicate wirelessly through the communication interface 766, which can include digital signal processing circuitry where necessary. The communication interface 766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple ACCess), CDMA2000, or GPRS (General Packet Radio Service), among others. Such communication can occur, for example, through the transceiver 768 using a radio-frequency. In addition, short-range communication can occur, such as using a Bluetooth, WiFi, or other such transceiver (not shown). In addition, a GPS (Global Positioning System) receiver module 770 can provide additional navigation- and location-related wireless data to the mobile computing device 750, which can be used as appropriate by applications running on the mobile computing device 750.

The mobile computing device 750 can also communicate audibly using an audio codec 760, which can receive spoken information from a user and convert it to usable digital information. The audio codec 760 can likewise generate audible sound for a user, such as through a speaker, e.g., in a handset of the mobile computing device 750. Such sound can include sound from voice telephone calls, can include recorded sound (e.g., voice messages, music files, etc.) and can also include sound generated by applications operating on the mobile computing device 750.

The mobile computing device 750 can be implemented in a number of different forms, as shown in the figure. For example, it can be implemented as a cellular telephone 780. It can also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a LCD (liquid crystal display) display screen for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

In various implementations, operations that are performed "in response to" or "as a consequence of" another operation (e.g., a determination or an identification) are not performed if the prior operation is unsuccessful (e.g., if the determination was not performed). Operations that are performed "automatically" are operations that are performed without user intervention (e.g., intervening user input). Features in this document that are described with conditional language may describe implementations that are optional. In some examples, "transmitting" from a first device to a second device includes the first device placing data into a network for receipt by the second device, but may not include the second device receiving the data. Conversely, "receiving" from a first device may include receiving the data from a network, but may not include the first device transmitting the data.

"Determining" by a computing system can include the computing system requesting that another device perform the determination and supply the results to the computing system. Moreover, "displaying" or "presenting" by a computing system can include the computing system sending data for causing another device to display or present the referenced information.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Further to the descriptions above, a user may be provided with controls allowing the user to make an election as to both if and when systems, programs or features described herein may enable collection of user information (e.g., information about a user's social network, social actions or activities, profession, a user's preferences, or a user's current location), and if the user is sent content or communications from a server. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

Figure 8:
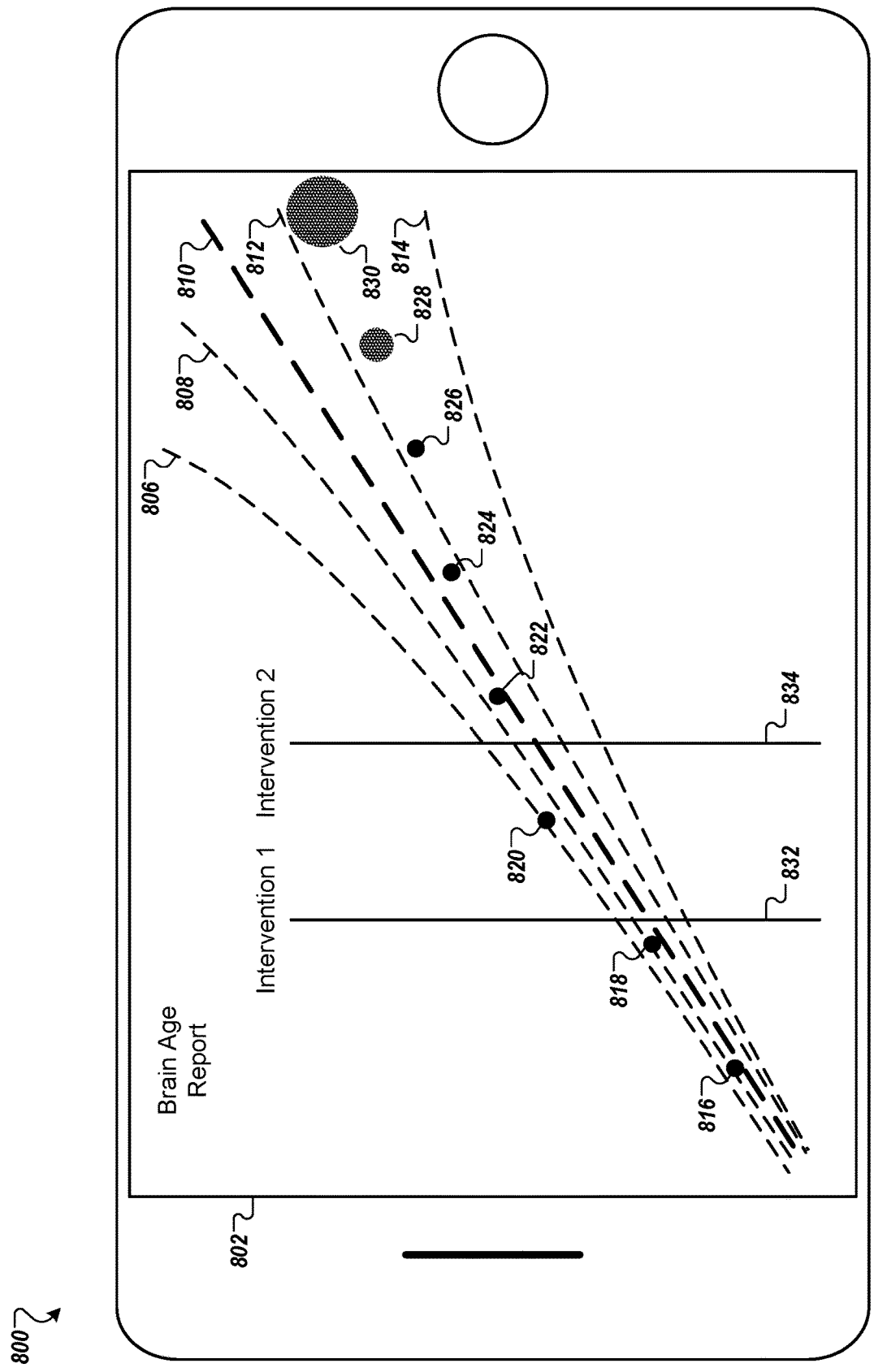
FIG. 8 is an example user interface showing a subject's brain age and estimated future brain age.

FIG. 8 is an example user interface 802 showing a subject's brain age and estimated future brain age. For example, the interface 802 may be displayed on the screen of a computing device 800, printed to a sheet of paper, and/or stored by computer memory. The interface 802 shows a record of historic measures of brain age as has been described in this document, though in some implementations, some of the brain age measures may come from the technology described in this document and some measures may be generated from other types of data gathering (e.g., sleep session in a clinical environment).

The interface 802 can include a graphic with population trend lines 806-814. For example, a trend line 810 can show the rate of brain age increase given chronological age increase for the population as a whole, or a specific subpopulation to which the subject is a member. Trend lines 808 and 812 can show trends that are greater and lower than average, for example, +/−1 standard deviation or +/−10%. Trend lines 806 and 814 can show trends that are greater and lower than average, for example, +/−2 standard deviations or +/−25%.

Measured brain age values can be shown with elements 816-826, plotted against the trend lines 806-814. As can be seen, this subject has a history of brain age that is greater than the average, and for elements 816-820, a trend of accelerating brain age compared to the reference population.

Based on the record of brain ages used to generate the elements 816-826, predicted function-metric for the subject can be estimated to represent a measure of predicted future physiological measures at a future chronological. For example, these future measures of brain age can be rendered as elements 828 and 830. In this example, the larger size and different shading indicates to the viewer the relative confidence of the estimates, compared to the measured values for elements 816-826.

Records of one or more interventions can also be graphically shown with elements 832 and 834. With this arrangement, a viewer can advantageously perceive the impact of the interventions (e.g., that intervention 1 had minimal impact on slowing brain age, but that intervention 2 was very successful at reversing the subject's trend).

Figure 9:
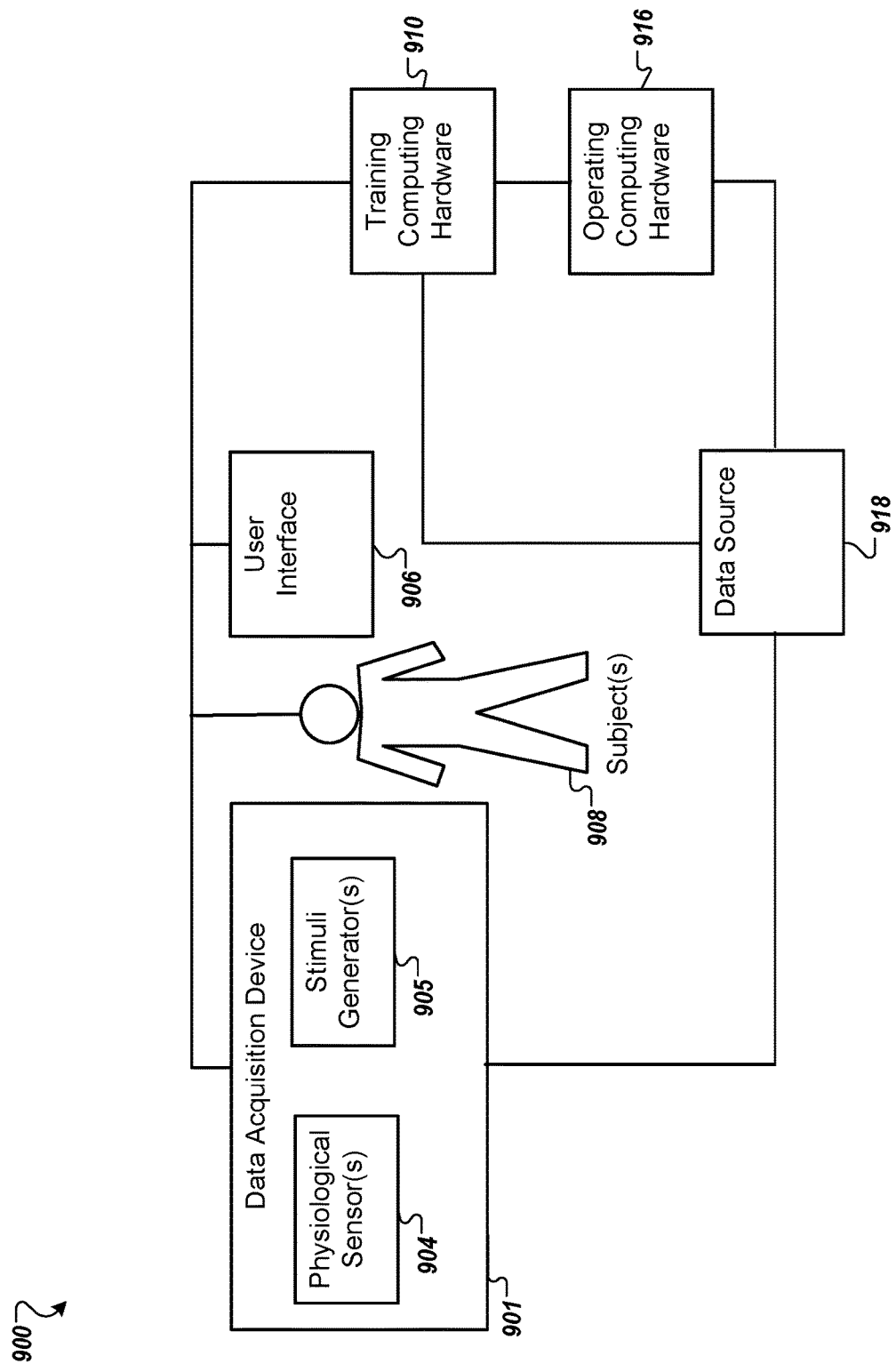
FIG. 9 shows an example system for determining a functional metric of a subject, consistent with embodiments of this disclosure.

Referring to the figures, FIG. 9 shows an example system 900 for determining timing of electrophysiological events of a subject, consistent with embodiments of this disclosure. The system 900 can include a data acquisition device 901 that has one or more physiological sensors 904 and one or more stimuli generators 905. The system 900 can include a user interface 906, training computer hardware 910, operating computing hardware 916, and a data source 918. The system 900 can be configured to collect data from one or more subjects 908, as will be described in further detail below.

In some aspects, the data acquisition device 901 can be worn by the subject 908 to collect data from the one or more physiological sensors 904. For example, the data acquisition device 901 can be configured to detect, measure, monitor, and record brain activity using electroencephalography (EEG), eye activity using electrooculography (EOG), muscle activity using electromyography (EMG), cardiac activity using electrocardiography (ECG), respiration rate (e.g., using respiratory inductance plethysmography (RIP), pressure sensor, and/or a temperature sensor), oxygen saturation (e.g., using pulse oximetry), heart rate (HR), blood flow, actigraphy during sleep, or any combination thereof. The stimuli generators 905 can generate audio stimuli, optical stimuli, visual stimuli, tactile stimuli, or combinations thereof to the subject 908, and the physiological sensors 904 can collect data that reflects the subject's 908 response to the stimuli.

The data collected by the data acquisition device 901 can be communicated throughout the system 900. For example, the data from the data acquisition device 901 can be displayed at the user interface 906, sent to the training computing hardware 910, sent to the operating computing hardware 916, and sent to the data source 918. Each of the data acquisition device 901, the user interface 906, the training computing hardware 910, and the operating computing hardware 916 can perform one or more of the processing steps described in further detail below (see e.g., FIGS. 12-14).

Figure 10A:
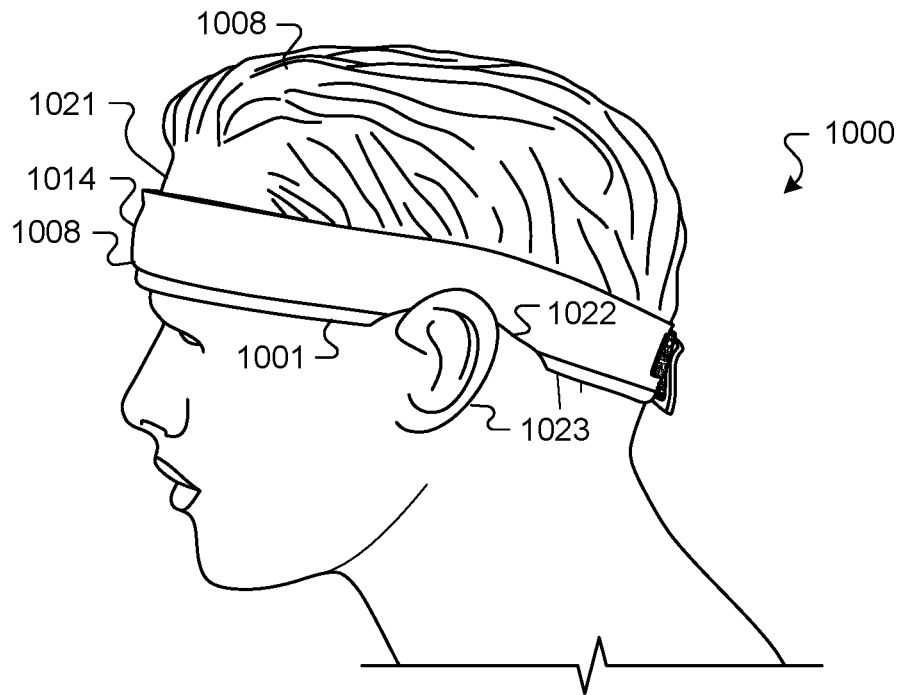
FIG. 10A shows an example data acquisition device on the head of a subject.
Figure 10B:
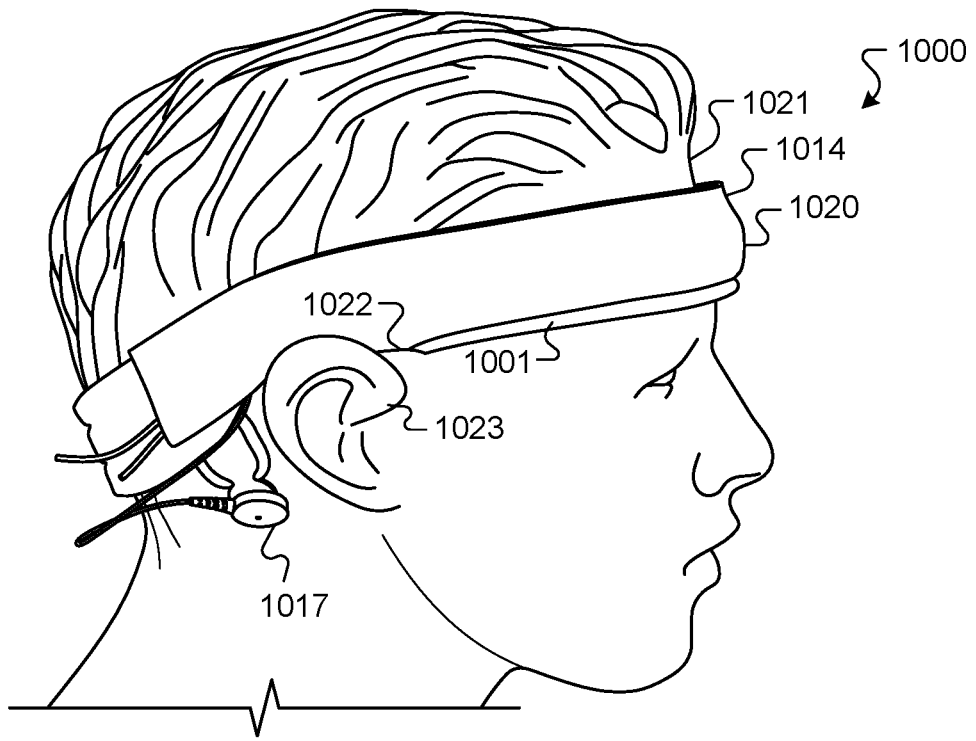
FIG. 10B shows the data acquisition device of FIG. 2A on the head of the subject.

FIGS. 10A and 10B show an example of a data acquisition system 1000 that includes a data acquisition device 1001 on the head of a subject. In some aspects, the data acquisition device 1001 can be the data acquisition device 901 of FIG. 9. The data acquisition device 1001 can be a head-worn sensing device that includes one or more sensors and one or more stimuli generators. The data acquisition device 1001 can have a body 1014 that can be a breathable material, for example a mesh material. The breathable material can allow the skin beneath the body 1014 to breathe. The breathable material can be elastic and/or inelastic. The elastic properties and the curved shape of the body 1014 can be configured to inhibit or prevent the data acquisition device 1001 from slipping during use, such as when the user moves during sleep (e.g., when the user shifts position or when one of their limbs or another person contacts the data acquisition device 1001). The body 1014 can extend partially or completely around a perimeter of a head 1008 of a subject.

The data acquisition device 1001 can be a removably attachable headband, cap, hat, strip (e.g., adhesive or hook-and-loop style fastening strip), biased band, or any combination thereof. The data acquisition device 1001 can have a curved shape, and the shape can include a closed or open loop (e.g., annular or semi-annular shape). The data acquisition device 1001 can extend partially or completely around a perimeter of the head 1008. The data acquisition device 1001 can include the body 1014 that has a curved profile that facilitates improved positioning of the data acquisition device. For example, the curved shape of the body 1014 facilitates a horizontal or nearly horizontal portion 1020 of the body 1014 that is positioned at and extends across a forehead 1021 of the head 1008 above the eyebrows of the subject. The body 1014 includes one or more notches 1022 that are positioned such that the body 1014 extends around each ear 1023 of head 1008 with the notches 1022 aligned with each ear 1023. The body 1014 further extends under a nape 1025 of the back of the head 1008. The curved shape of the body 1014 facilitates proper positioning of the data acquisition device 1001 on the head 1008 by inhibiting or preventing the data acquisition device 1001 from slipping during use, such as when the user moves during sleep (e.g., when the user shifts position or when one of their limbs or another person contacts the data acquisition device 1001).

The body 1014 can include slip resistant edges that are configured to keep one or more sensors of the data acquisition device 1001 in position during use such that there is strong contact and less resistance to movement at the point where the sensors come into contact with the skin. This can advantageously ensure that the device sensors can have reliable contact with the skin.

The data acquisition device 1001 can be configured to measure and collect one or more physiological parameters during sleep. For example, the data acquisition device 1001 can be configured to detect, measure, monitor, and record brain activity, eye activity, muscle activity (e.g., body posture, limb movements), cardiac activity (e.g., heart rate, heart rate variability (HRV)), respiration activity (e.g., respiration rate), blood oxygen saturation, blood flow rates, or any combination thereof. For example, the data acquisition device 1001 can be configured to detect, measure, monitor, and record brain activity using electroencephalography (EEG), eye activity using electrooculography (EOG), muscle activity using electromyography (EMG), cardiac activity using electrocardiography (ECG), respiration rate (e.g., using respiratory inductance plethysmography (RIP), pressure sensor, and/or a temperature sensor), oxygen saturation (e.g., using pulse oximetry), heart rate (HR), blood flow, actigraphy during sleep, or any combination thereof. The data acquisition device 1001 can be configured to detect, measure, monitor, and record pressure and temperature, for example, using one or more pressure sensors and/or one or more temperature sensors. The data acquisition device 1001 can perform polysomnography (PSG) tests and can collect polysomnographic data. The data that is collected is referred to throughout as acquired data, raw data, and/or sleep data.

Figure 10C:
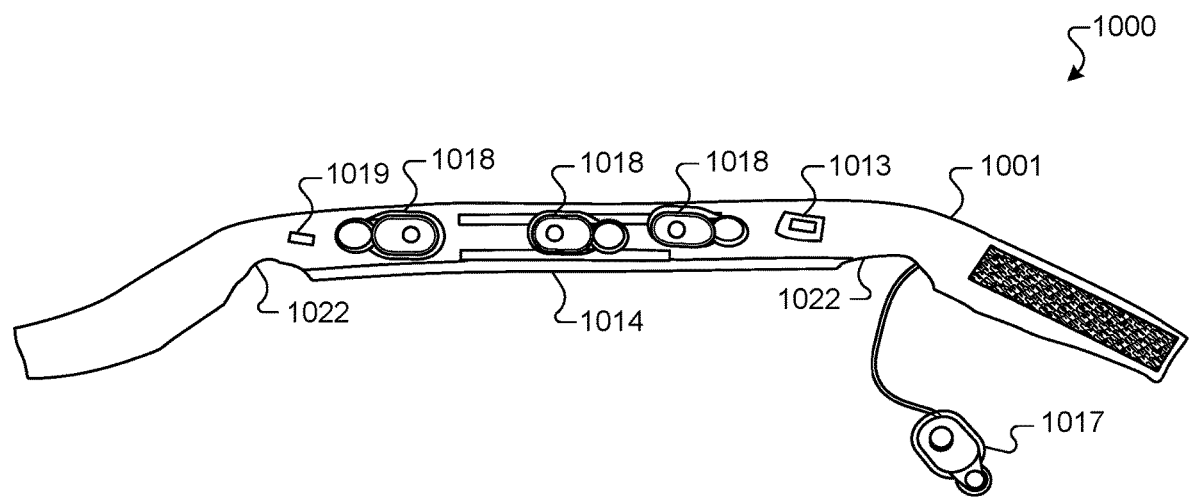
FIG. 10C shows the data acquisition device of FIGS. 2A and 2B removed from the head of the subject.
Figure 10D:
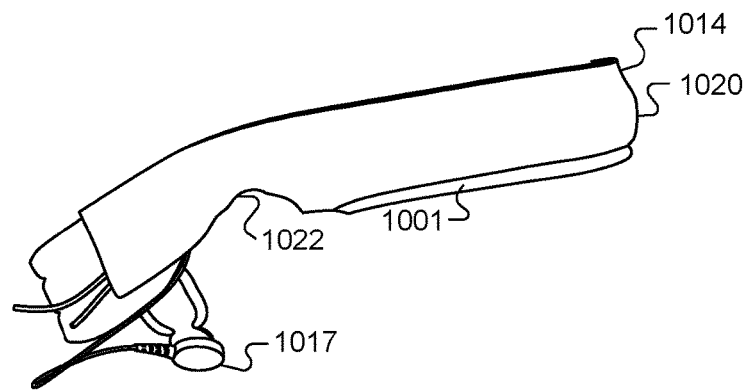
FIG. 10D shows the data acquisition device of FIGS. 2A and 2B removed from the head of the subject.

As shown in FIGS. 10C and 10D, the data acquisition device 1001 can have one or more data acquisition modules 1018 (also referred to as electronics modules 1018), for example, 9 to 13 data acquisition modules 1018, including every 1 module increment within this range (e.g., 2 electronics modules). For example, the data acquisition device 1001 can have one electronics module 1018. In another example, the data acquisition device 1001 can have a plurality of data acquisition modules 1018 spaced apart around the data acquisition device 1001 to provide sensors at a variety of positions around the head 1008 of the subject to optimize data collection.

The one or more data acquisition modules 1018 can be configured to monitor and record one or more physiological activities during sleep. For example, the data acquisition modules 1018 can be configured to detect, measure, monitor, and record brain activity, eye activity, muscle activity, cardiac activity, respiration activity, blood oxygen saturation, blood flow, actigraphy, or any combination thereof (e.g., using EEG, EOG, EMG, ECG, RIP, pulse oximetry, or any combination thereof, respectively). The one or more data acquisition modules 1018 can be computer interfaces, for example, brain computer interfaces (BCIs).

The data acquisition modules 1018 can have one or more electrodes, sensors (e.g., biosensors), accelerometers, or any combination thereof. For example, the data acquisition modules 1018 can have one or more EEG biosensors, EOG biosensors, EMG biosensors, ECG biosensors, respiration rate biosensors, pulse oximetry biosensors, HRV biosensors, temperature sensors, pressure sensors, or any combination thereof, including one or more reference sensors and/or one or more ground electrodes.

The data acquisition modules 1018 can have a single-channel and/or a multi-channel EEG system. The multi-channel EEG system can be operated as a single channel EEG system. The EEG system (single or multi-channel) can include one or more EEG sensors. The data acquisition device 1001 (e.g., the data acquisition modules 1018) can have 1 to 10 EEG sensors, including every 1 EEG sensor within this range (e.g., 4 EEG electrodes). The data acquisition modules 1018 can have more than 10 sensors (e.g., 1 to 100 EEG sensors). The data acquisition modules 1018 can have an EEG sensor array or an EEG sensor network (e.g., of 2 to 10 or more sensors). One of the EEG sensors can be a ground electrode. The EEG system can have one or multiple reference electrodes (e.g., one or two reference electrodes). The electronics module 1018 can have, for example, three channels of frontal EEG and one EEG reference sensor or three channels of prefrontal EEG and one EEG reference sensor. The EEG electrodes can be positioned on the forehead, for example, the EEG electrodes can be placed at forehead positions such as Fp1 and Fp2. The EEG electrodes can be placed according to the international 10-20 system.

The data acquisition modules 1018 can have 2, 3, or 4 EOG sensors. Two EOG sensors can detect/measure movement of one or both eyes. For example, two EOG sensors can be positioned to detect/measure eye movement of the left and right eyes (e.g., a first EOG sensor can be positioned on the right outer edge of the right eye and a second EOG sensor can be positioned on the left outer edge of the left eye), two EOG sensors can be positioned to detect/measure eye movement of only the left eye (e.g., a first EOG sensor can be positioned on the right outer edge and a second EOG sensor can be positioned on the left outer edge of the left eye), or two EOG sensors can be positioned to detect/measure eye movement of only the right eye (e.g., a first EOG sensor can be positioned on the right outer edge and a second EOG sensor can be positioned on the left outer edge of the right eye). Three EOG sensors can be positioned to detect/measure eye movement of the left and right eyes (e.g., a first EOG sensor can be positioned on the right outer edge of the right eye, a second EOG sensor can be positioned on the left outer edge of the left eye, and a third EOG sensor can be positioned between the left and right eyes). The three EOG sensors can selectively detect/measure eye movement of the left and/or right eyes, with the first and third EOG sensors configured to detect/measure movement of the right eye, with the second and third EOG sensors configured to detect/measure movement of the left eye, and with the first and second EOG sensors configured to detect/measure movement of the left and right eyes together. Four EOG sensors can be positioned to detect/measure eye movement of the left and right eyes (e.g., first and second EOG sensors can be positioned on first and second sides of the left eye and third and fourth EOG sensors can be positioned on first and second sides of the right eye). The "outer edges" of the eyes can be in line with the eyes, above the eyes and/or below the eyes.

The data acquisition system 1000 can have 1 to 6 EMG sensors, including every 1 EMG electrode increment within this range (e.g., 2 EMG electrodes). The data acquisition system 1000 (e.g., the data acquisition device 1001 and/or the data acquisition modules 1018) can have 1 to 10 ECG sensors, including every 1 ECG electrode increment within this range (e.g., 1, 2, or 3 ECG electrodes). The ECG sensors can be used to measure HRV. The ECG sensors can be used to determine HRV.

The data acquisition system 1000 (e.g., the data acquisition device 1001 and/or the data acquisition modules 1018) can have 1 to 10 heart rate sensors (e.g., photoplethysmography (PPG) sensor), including every 1 heart rate sensor increment within this range (e.g., 1, 2, or 3 heart rate sensors). The heart rate sensors can be used to measure HRV. The heart rate sensors can be used to determine HRV.

The data acquisition system 1000 (e.g., the data acquisition device 1001 and/or the data acquisition modules 1018) can have one or multiple pressure sensors (e.g., pressure transducers) and/or temperature sensors (e.g., thermocouples) configured to monitor respiration. For example, the data acquisition device 1001 can have 1 to 4 pressure sensors, including every 1 pressure sensor increment within this range (e.g., 1 or 2 pressure sensors). The data acquisition device 1001 can have 1 to 4 temperature sensors, including every 1 temperature sensor increment within this range (e.g., 1 or 2 temperature sensors). The pressure and/or temperature sensors can be positionable near the nostrils and can be configured to detect the pressure/temperature changes that occur when a user inhales and exhales. The pressure and/or temperature sensors can be attached to or integrated with the data acquisition device 1001 such that when the data acquisition device 1001 is removably secured to a head, the pressure and/or temperature sensors are positioned in a breathing flow path (e.g., near the nostrils and/or mouth, for example, for mouth breathers).

The data acquisition device 1001 can have a pulse oximetry sensor that can be removably attachable to an ear, for example, to an ear lobe. The data acquisition system 1000 can have a pulse oximetry sensor that can be removably attachable to a finger. The finger pulse oximetry sensor can be in wired or wireless communication with the data acquisition device 1001 (e.g., to the electronics module 1018) and/or to the data display device. The ear pulse oximetry sensor can be attached to or integrated with the data acquisition device 1001. The pulse oximetry sensor (ear and finger sensor) can be a component of a clip. The clip can attach to (e.g., clip to) an ear lobe or a finger. The clip can be attached to or integrated with the data acquisition device 1001, for example, to the body 1014. The pulse oximetry sensor can be placed on the forehead. The forehead pulse oximetry can be attached to or integrated in the data acquisition device 1001.

The data acquisition device 1001 can have one or more pressure sensors (e.g., 1, 2, 3, 4, 5, 6 or more) configured to detect when the data acquisition device 1001 is attached to a head, for example, by measuring the amount of force exerted against each of the pressure sensors. The data acquisition system 1000 can be configured to detect whether the data acquisition device 1001 is properly positioned on the head, for example, by detecting and/or comparing the different pressures measured by the one or more pressure sensors (e.g., by calculating one or more pressure differentials). The pressure sensors can also be used to determine whether the position can be improved or further optimized, for example, for more accurate and/or reliable data collection. The data acquisition device 1001 can be activated (e.g., automatically or manually) when positioned on the head 1008 as a result of one or more pressure sensors exceeding a pressure threshold. The data acquisition device 1001 can be activated (e.g., automatically or manually) when positioned on the head 1008 as a result of one or more differential pressure differentials (e.g., between two sensors) falling below a differential pressure threshold.

For example, a first pressure sensor can be on a first side of the data acquisition device 1001 and a second pressure sensor can be on a second side of the data acquisition device 1001. The pressure sensors can be separated by about 9 degree to about 980 degrees as measured from a center of the data acquisition device 1001 (e.g., along a longitudinal and/or transverse axis), including every 1 degree increment within this range. The center of the data acquisition device 1001 can fall between two inner sides of the device such that the device center is not on the body and/or edges of the data acquisition device 1001. A 180 degree separation can correspond to a configuration in which the first and second pressure sensors are diametrically opposed from one another. Angles less than 180 degrees can correspond to configurations in which the first and second pressure sensors are on opposite sides of the device, determined for example relative to a reference axis. Angles less than 180 degrees can correspond to configurations in which the first and second pressure sensors are on the same side of the device, determined for example relative to a reference axis. The first and second pressure sensors can be used to determine a side-to-side or a front-to-back pressure differential of the data acquisition device 1001 (i.e., the pressure levels on the left side, right side, front side, and/or back side of the data acquisition device 1001). Four pressure sensors can be used to determine side-to-side and/or front-to-back pressure differentials of the device when removably attached to a head. The angles between sensors can be from about 1 degree to about 180 degrees, including every 1 degree increment within this range.

The data acquisition system 1000 (e.g., the data acquisition device 1001, a user's device, and/or a remote server) can determine whether the data acquisition device 1001 is properly or improperly positioned by analyzing the pressure readings of the one or more pressure sensors. The data acquisition system 1000 can assess the quality of the data signals from the data acquisition modules 1018 to ensure proper stability and contact of data acquisition modules 1018 is occurring to ensure high quality data is being obtained by the data acquisition device 1001. If properly positioned, the data acquisition device 1001 can automatically begin collecting data (e.g., immediately or after one or more additional conditions are satisfied). The data acquisition device 1001 can collect data when not positioned properly, however, some of the data may have accuracy, precision and/or reliability issues, or some of the data may be missing altogether (e.g., pulse oximetry data). The data acquisition system 1000 can notify the user that the data acquisition device 1001 is not positioned properly. Additionally or alternatively, the data acquisition system 1000 can be configured to determine whether the data acquisition device 1001 is properly positioned by measuring the voltage drop across one or more sensors of the data acquisition modules 1018).

The data acquisition device 1001 can begin collecting data when one or more conditions are satisfied (e.g., 1 to 10 or more conditions). The data acquisition device 1001 can begin collecting data when a proper position is detected. The data acquisition device 1001 can begin collecting data when the data acquisition system 1000 detects that the user is in a sleeping position and/or when the user is in a sleeping location, for example, for a predetermined amount of time (e.g., immediately (no time), or after 1 min to 5 min or more have elapsed). The sleeping location can be established or otherwise settable by the user. For example, the data acquisition device 1001 can begin collecting data after first, second, third, and/or fourth conditions are satisfied. The data acquisition device 1001 can begin collecting data immediately after any one condition or combination of conditions is satisfied. The first condition can correspond to correct device placement (e.g., of the data acquisition device 1001). The second condition can correspond to user input (e.g., selection of a command prompt). The third condition can correspond to a position of the device relative to the environment, for example, whether the orientation of the data acquisition device 1001 is in a position indicative of a sleeping position of the user (e.g., lying down, either prone, supine, or on side). The fourth condition can correspond to a location of the user (e.g., on a bed). Sleep data collection can begin when the pressure sensors detect that the data acquisition device 1001 is properly attached to a head, when the data acquisition modules 1018 begin collecting data, or when the acquired data meets quality thresholds.

The data acquisition device 1001 can have one or more temperature sensors (e.g., 1, 2, 3, 4 or more temperature sensors) configured to monitor a user's body temperature. The temperature sensors can be temperature transducers (e.g., thermocouples). The temperature sensor can be attached to or integrated with the data acquisition device 1001. The temperature sensors can be configured to detect when the data acquisition device 1001 is attached to a head, for example, by detecting a body temperature. An environment temperature sensor can be configured to measure environmental temperature. The environment temperature sensor can be one of the temperature sensors of the data acquisition device 1001. The environment temperature sensor can be a temperature sensor of a sleeping location (e.g., house or apartment). The data acquisition system 1000 can determine a user's optimum sleeping temperature and suggest a sleeping temperature for the user, for example, from about 60 degrees Fahrenheit to about 85 degrees Fahrenheit, including every 1 degree increment within this range.

The data acquisition system 1000 (e.g., the data acquisition device 1001 and/or the data acquisition modules 1018) can have one or more accelerometers (e.g., one accelerometer). The accelerometer can be attached to the data acquisition device 1001 or can be wirelessly connected (e.g., located at the subject's wrist, finger, or other location). In some aspects, the accelerometer can detect limb movements of the subject. The accelerometer can detect a user's positional state, for example, a user's movement or sleeping pose (e.g., prone, on side). The accelerometer can be a two-axis accelerometer. The accelerometer can be a three-axis accelerometer. The accelerometer can be configured to detect head, body, and/or limb movements, or any combination thereof. The accelerometer can be used to detect lack of movement as well, for example, the length of time in a single position without movement or with movement within a specified tolerance (e.g., voltage level or movement amount, for example, 5 cm or less).

The electronics modules (e.g., data acquisition modules 1018) can include, for example, three channels of prefrontal EEG and one EEG reference sensor to detect brain wave activity, a heart rate sensor (e.g., a pulse oximetry sensor, an ECG sensor, or other sensors described throughout) to monitor cardiac activity (e.g., RR variability), an accelerometer (e.g., two or three axis accelerometer) to detect head, body, and/or limb movements, or any combination thereof.

The electronics module 1018 can be configured to contact a user's skin (e.g., a user's forehead) during use. The data acquisition device 1001 can press the EEG sensors and/or ECG sensor(s) against the user's skin (e.g., forehead) when secured to the head 1008, for example, with an elastic fit or with an interference fit. Alternatively or additionally, the sensors can be adhered to the user's skin (e.g., forehead) using an adhesive with or without the data acquisition device 1001.

The electronics module 1018 can be configured to measure brain activity, for example, during light sleep, during rapid eye movement (REM) sleep, during slow-wave sleep (SWS) (also referred to as deep sleep), or any combination thereof. The electronics module 1018 can be configured to measure cardiac activity, for example, HRV such as RR intervals. The electronics module 1018 can be configured to detect a user's motion and/or a user's lack of motion. These sensors may be integral to other components (e.g., stitched into a headband), may be removable (e.g., by removable snap or friction fit), or may be otherwise used with headbands or other worn devices.

The electronics module components (e.g., channels, sensors, accelerometers, stimuli generators) can be attached to or integrated with the data acquisition module 1018. The data acquisition module 1018 can be permanently attached to, removably attached to, or integrated with the data acquisition device 1001 (e.g., to and/or with the body 1014). Additionally or alternatively, the various activity-measuring components (e.g., channels, sensors, accelerometers) can be attached to or integrated with an attachment portion of the data acquisition device 1001, for example the body 1014 separate and apart from the module 1018. The module 1018 can be interchangeable with one or more other modules (not shown) having a different number of sensors, one or more different types of sensors, or otherwise having at least one different parameter-measuring capability relative to the electronics module 1018. The electronics module 1018 can be interchangeable with another module having the same exact module or otherwise with another module having the same exact parameter-measuring capabilities. Different electronics modules 1018 can have different sizes relative to one another. Different modules 1018 can have different shapes relative to one another.

The data acquisition device 1001, a user device, and/or a remote server can analyze the sleep data collected, as described in further detail below. The data acquisition device 1001, the user device, and/or a remote server can determine one or more parameters from the data collected, for example, using one or more programmable processors. The parameters can include total light sleep, total SWS (also referred to as total deep sleep), total REM sleep, total non-REM sleep (total light sleep and total SWS added together), total sleep (total REM and non-REM sleep added together), longest deep sleep duration, deep sleep amplitude, strength of deep sleep, heart rate, heart rate variability, total time in bed, time to fall asleep, time awake between falling asleep and waking up, various sleep microstructure features (e.g., number of sleep slow oscillation (SO) events described in further detail below), or any combination thereof. The time-based parameters (e.g., the "total," "duration," and "time" parameters) can be measured in the time domain, for example, using seconds, minutes, hours. Days, weeks and years can be used for accumulated and/or running totals.

The total time in bed parameter can be measured from a start point to an end point. The start point can correspond to when the user manually activates the data acquisition device 1001, for example, by selecting a start instruction (e.g., "ready to sleep") on the display 102. The start point can correspond to when the data acquisition device 1001 is activated (e.g., automatically or manually). The data acquisition device 1001 can be automatically activated, for example, when a voltage is detected across two or more sensors of the module 1018 (e.g., across two or more of the EEG electrodes). The voltage can indicate contact with skin and cause the data acquisition device 1001 to begin measuring the total time in bed. The data acquisition device 1001 can have a timer. The data acquisition device 1001 can be automatically activated when positioned on the head 1008 as a result of one or more pressure sensors exceeding a pressure threshold. The end point can correspond to when the user manually deactivates the data acquisition device 1001, for example, by selecting an end instruction (e.g., "turn off alarm" or "get sleep report") on the display 102. The end point can correspond to when the device is automatically deactivated. The data acquisition device 1001 can be automatically deactivated, for example, when the accelerometer indicates the user is walking around or has taken the data acquisition device 1001 off their head.

The data acquisition system 1000 can provide audio stimulation (also referred to as audio entrainment) using, for example, one or more sound wave generators 1017 (e.g., 1 to 4 sound wave generators). The sound wave generators can be, for example, speakers. A portion of the data acquisition device 1001 can be positionable over and/or engageable with a left and/or right ear of a user such that the sound wave generators 1017 can emit sound into a user's ears. The sound wave generators 1017 can be attached to, embedded in, or integrated with the device body 1014. The sound wave generators 1017 can be in wired or wireless communication with the data acquisition device 1001, a user device, a remote server, or any combination thereof. The sound wave generators 1017 can be micro speakers. The sound wave generators 1017 can be in wired or wireless communication with the data acquisition device 1001 and can be attached Additionally or alternatively, the data acquisition system 1000 can provide audio stimulation via bone conduction by transmitting sound signals through bone to a user's inner ear. The data acquisition system 1000 can have one or more actuator assemblies 1013 to provide bone conduction sound transmission. The actuator assemblies 1013 can have an actuator (e.g., a transducer). The actuator can be vibratable (e.g., the actuator can be configured to vibrate). The actuator assemblies 1013 can have a transceiver coupled to the actuator. The transceiver can cause the actuator to vibrate to generate sound, for example, when the transceiver is electronically driven with sound signals (e.g., from a driver and/or a controller, for example, from the data acquisition device 1001). The actuator can be a piezoelectric actuator. The piezoelectric actuator can be configured to move a mass to provide sound through bone. The actuator assemblies 1013 (e.g., the actuator) can be positioned near the ear and/or on the cheek. For example, the actuator assemblies 1013 can be positioned on a user's skin proximate the zygomatic bone, the zygomatic arch, the mastoid process, or any combination thereof. The data acquisition system 1000 can have 9 to 14 actuator assemblies, or 9 to 14 actuators, including every 1 actuator assembly/actuator increment within these ranges.

The data acquisition system 1000 can provide visual/optical stimulation (also referred to as light entrainment) using, for example, one or more light emitting sources 1019 (e.g., 9 to 100 light emitting sources). A portion of the data acquisition device 1001 can be positionable over and/or engageable with a left and/or right eye of a user such that the light sources 1019 can emit light into a user's eyes (e.g., through the user's closed eyelids). The data acquisition device 1001 can be configured to partially or completely cover one, both, or no eyes. The data acquisition device 1001 can be configured for temporary securement above or proximate to a user's eyes/eyelids. For example, a portion of the data acquisition device 1001 can be configured to rest against and/or adhere to an eyebrow, the area proximate an eyebrow, the glabella, the nose (e.g., dorsal bridge, dorsal base, tip), cheek, or any combination thereof. The light sources 1019 can be attached to, embedded in, or integrated with the data acquisition device 1001.

The data acquisition system 1000 can provide audio entrainment, optical entrainment, cranial electrotherapy stimulation (CES), or any combination thereof, in addition to or in lieu of the data collection and associated analyses described below.

Figure 11A:
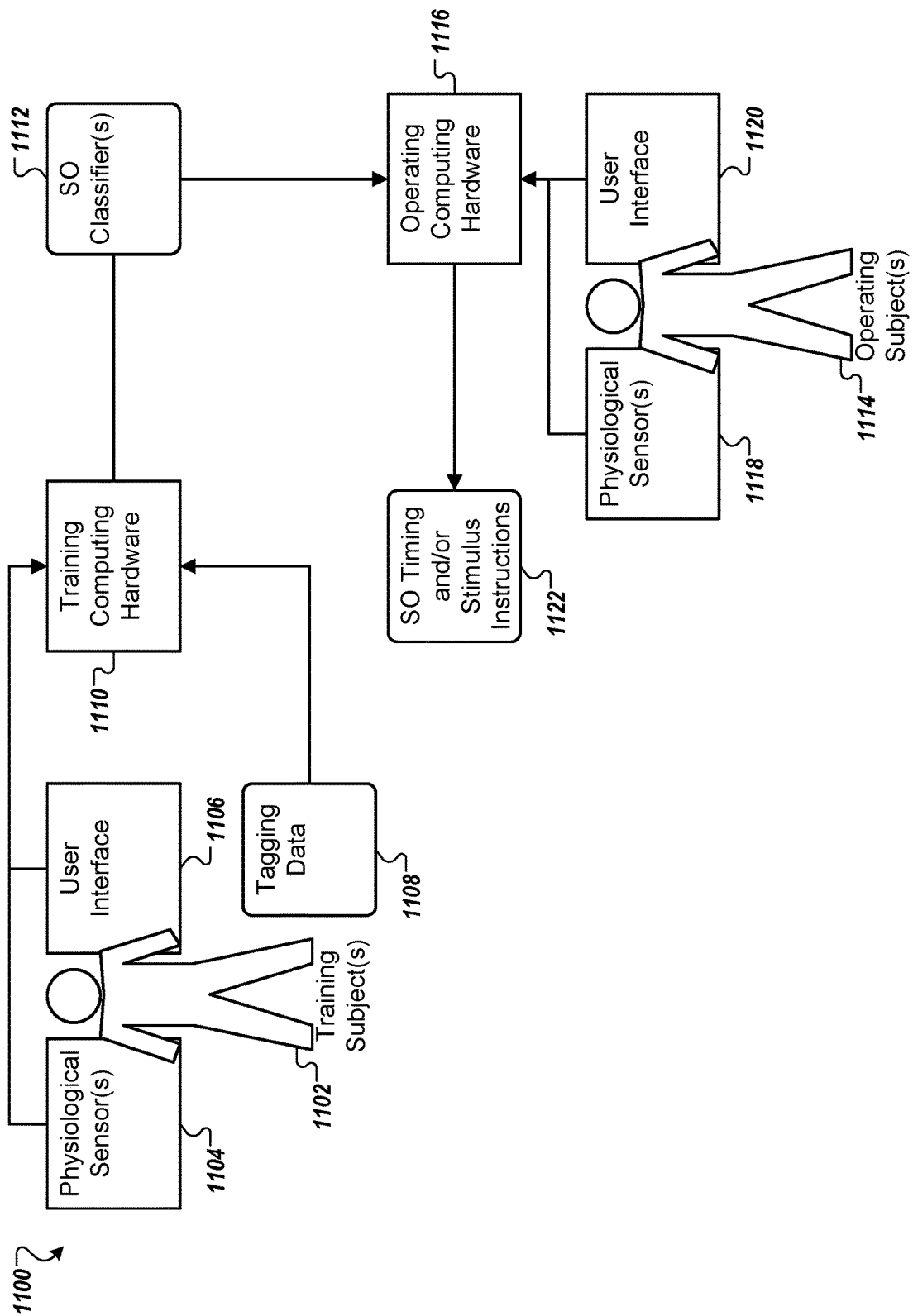
FIGS. 11A-11C show an example system and data for determining timing of electrophysiological events of a subject.

FIG. 11A shows an example system 1100 for determining metrics of a subject, such as SO timing data for a user of a head-worn sensing device (e.g., data acquisition device 1001) as previously described. In this system, one or more training subjects 1102 provide training data through physiological sensors 1104 and user interfaces 1106 (either directly or by another user such as an administrator or health-care provider), which can be combined with tagging data 1108 by training computing hardware 1110 to generate one or more function-metric classifiers 1112. Operating subjects 1114 can then use operating computing hardware 1116 to collect data through physiological sensors 1118 and/or user interfaces 1120 to generate one or more function metrics 1122. The data provided through the user interface 1106 can include information about the subject 1102 useful for tagging data collected from the subject using the physiological sensors 1104. For example, name, age, and other demographic data may be used to create subpopulation samples of sensed data. Instructions can be presented to the subject 1102 to don the physiological sensors 1104 and, upon pressing an interface element (e.g., a button on a screen) confirming the sensors 1104 are in place, sensing can begin.

Training subjects 1102 are a group of subjects (e.g., human or other animals) that contribute data to be used as training data. For example, the subjects 1102 may be patients who, under a program of informed consent, provide some of their medical records for research purposes. In another example, the subjects 1102 may be generally healthy representatives of a population that have agreed to contribute training data. The training subjects 1102 may be organized by physiological (e.g., healthy vs having a known medical issue, menopausal status, menstrual cycle phase, sleep disorders, hypertension, diabetes, mental or behavioural health condition), demographic details (e.g., age, gender, geographic location, location of residence, education level, professional level), and/or groups based on lifestyle factors (e.g., activity level, past or current behaviours, schedule such as shift work, short sleepers). Thus, classifiers 1112 may be created for the population as a whole, or for particular subpopulations (e.g., stratified by health status, age, or other factors expected to impact the operation of the classifiers). In some cases, each classifier 1112 may be personalized, using a single subject 1102 to create or modify a classifier, where the training subject 1102 is also the operating subject 1114 so that their personal classifier is used later in operation.

Physiological sensors 1104 include one or more sensors that can sense one or more physiological phenomena of the subjects 1102. In some cases, the sensors 1104 can include sensors mounted in a head-worn device such as the data acquisition modules 1018 of the data acquisition device 1001 and the physiological sensors 904 of the data acquisition device 901. However, other arrangements are possible such as bespoke training sensors used only for the collection of training data, or use of data collected with other sensors for other purposes (e.g., use of some of, but not all, data generated in clinical sleep studies).

The user interface 1106 can include hardware and corresponding software to present user interfaces to a user (e.g., subject 1102 or another user) to collect data about the subject 1106. This can include the demographic data described, can present information to the subject 1102 about the use of data collected and aid in the development of informed consent, etc. The user interface 1106 can include a personal computing device such as a desktop or laptop, a mobile computing device such as a phone, tablet, raspberry pi or other appropriate elements for user input and output.

Tagging data 1108 includes data that annotates data from the physiological sensors 1104 and/or the user interface 1106. For example, a user (shown or not shown) and/or an automated system (shown or not shown) can annotate data from the physiological sensors 1104 to mark the subject 1102 as in states such as sleep-states, and to mark the data related to SOs (e.g., SO peak timing, SO peak values, SO-spindle coupling). These tags in the tagging data 1108 can also include other data that can be used in the creation of the classifiers.

The training computer hardware 1110 can receive the tagging data 1108, data from the physiological sensors 1104, and/or data from the user interface 1106 to generate one or more SO classifiers 1112. Example processes for such classifier creation are described in greater detail elsewhere in this document. The classifier 1112 can, given a particular set of inputs, generate one or more predictions of SO value. These SO value predictions can include values that give an indication of the expected state of EEG signals (or other signals) of training subjects 1102 while they are being monitored with the physiological sensors 1104.

Figure 11B:
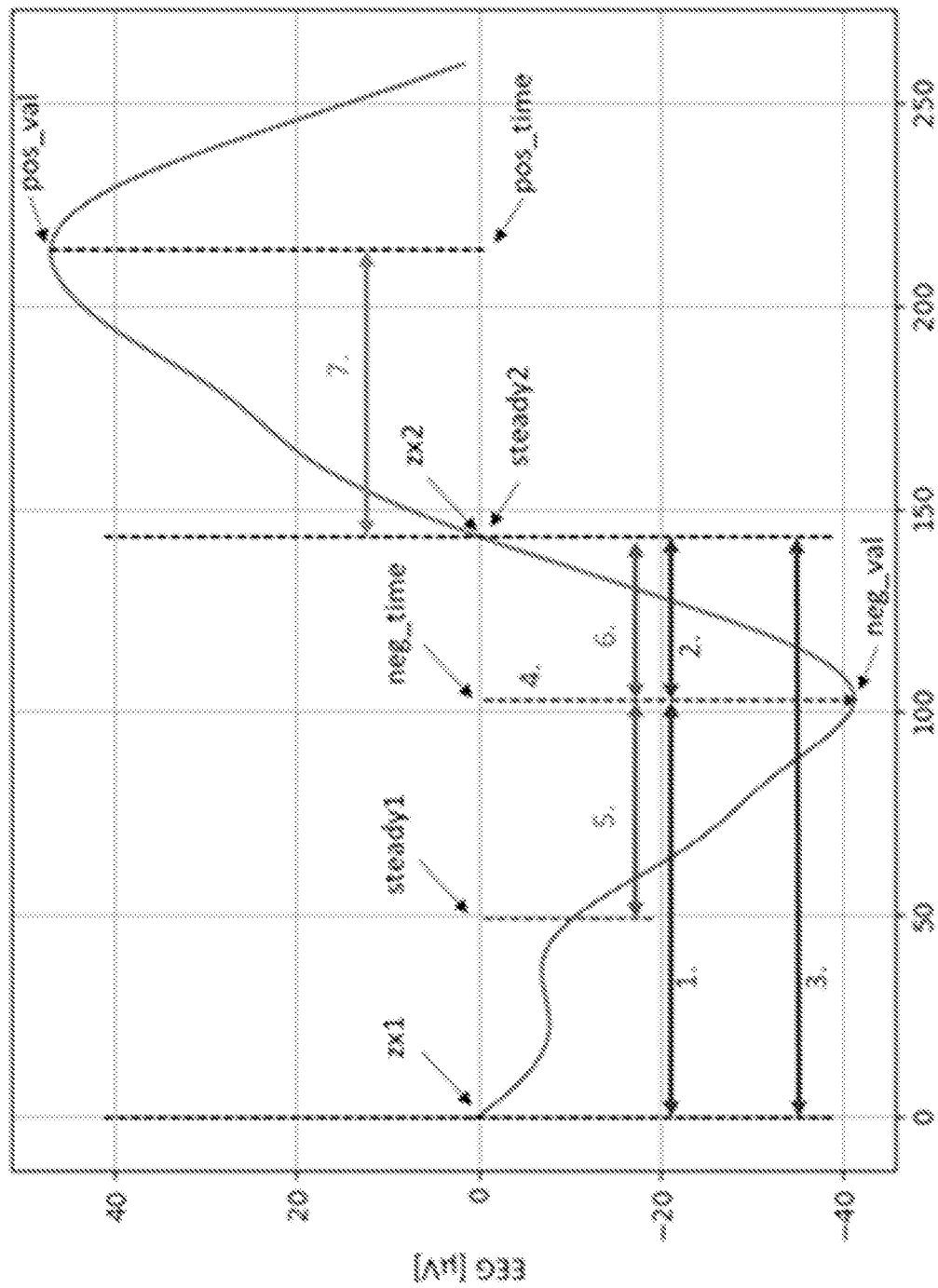

These SO value predictions can be generated for the subject 1114 within the same sleep session, and even within the same single wave. FIG. 11B shows an example of a single wave of the subject 1114, annotated with a number of possible event points. In an example, a SO classifier 1112 may be provided with EEG data for wave from time 0 milliseconds to time 50 milliseconds (i.e., at point steady1), and the classifier 1112 can predict the timing of zx2 at 150 milliseconds. Importantly, the operation of the classifier can be completed in less than 100 milliseconds, meaning the prediction of the timing of zx2 is generated before the subject actually experiences activity of zx2, allowing for the timing of stimulation at xz2. For a system with 17 milliseconds of lead time between instructing actuation of stimulation and performance of the stimulation, the actuation instruction can be issued at time 133 milliseconds, resulting in delivery of the stimulus at time 150 milliseconds—the predicted time of zx2. This timing can use a data value for a decision point (e.g., a point a given number of milliseconds from the start of an SO waveform, a point at or referenced to a particular point in the waveform). This point of decision can be used as the last point in time at which an instruction can be issued while still accounting for all delays, including filtering delays, actuation delays, etc.

Returning to FIG. 11A, after the classifier 1112 has been created, one or more operating subjects 1114 can use the physiological sensors 1118 and/or user interface 1106 to provide new data to the operating computing hardware 1116. The computing hardware can use this new data with the classifier 1112 to create new SO classifiers 1112 for the operating subjects 1114. Said another way, the users 1114 can wear a headband (e.g., data acquisition device 1001) to bed as previously described, and they can receive stimulus as previously described. In addition to tracking the subject's 1114 EEG for delivery of the stimulus, the hardware 1116 can also refine the classifiers 1112 with the tracked EEG of the subject 1114. As will be appreciated, this can advantageously provide the users 1114 with a system that both i) improves their health or wellness, resulting in a beneficial change in neurophysiological behavior and ii) updates for the changing neurophysiological behavior. The users 1114 can also be provided with assessments or reports of their changing neurophysiological behavior.

FIG. 11B shows a subject brain 1150. Schematically shown is brain activity 1152, for example the subject sleeps. As will be understood, brain activity generally includes electrochemical or other processes within the subject brain, and the depiction 1152 is a schematic representation of these activities shown for illustrative purposes. EEG data 1154 represents EEG readings and/or other data streams generated from sensing of the activity of the brain 1150. As will be appreciated, in the depicted data a current time is shown at time 1156. Earlier activity is shown farther to the left of the current time 1156. To the right of current time 1156, no activity 1152 or EEG data 1154 is shown, as the activity has not occurred yet.

Individual SO waveforms 1158, 1160, and 1162 can be identified in real-time. That is to say, as the waveform 1158 was being sensed in the activity 1152, it may be identified.

Then, when waveform 1160 was being sensed in the activity 1152, it may be identified. Now, at the current time 1156, the current SO waveform 1162 may be sensed, even as it is not yet completed.

Callout box 1164 shows the current SO waveform 1162 in greater detail. As will be appreciated, a current SO record can be stored in computer memory to record data for the current SO waveform 1162. In real-time, concurrently with the sensing and identification of the current SO waveform 1162. Various fiducial points before the current time are identified in real time (zx1, steady1, neg_time, neg_val, zx2, and steady2 in this example). Predictions for electrophysiological points or fiducial points that have not yet occurred (e.g., predicted_pos_time=225 milliseconds for pos_time and predicted_pos_val=43 µV for pos_val), can be generated before those electrophysiological events or fiducial points of the waveform occur in the activity 1152. In this way, an expected time, voltage, or other value can be predicated and stored in computer memory before the corresponding brain activity 1152 occurs. This can advantageously allow for the timing of automated events such as the delivery of subject stimulation targeted at a particular portion of SO.

Features may be generated from the fiducial points. For example, measures in time between two fiducial points may be used as a feature. In addition or in the alternative, other types of features may be used. A feature may be a measure of magnitude at a fiducial point. Some features are in different domains. For example, a frequency domain feature may include a measure related to frequency. For example, a spindle domain feature may include measures related to spindle coupling, timing of spindle maximum, the maximum value itself, etc.

Figure 12:
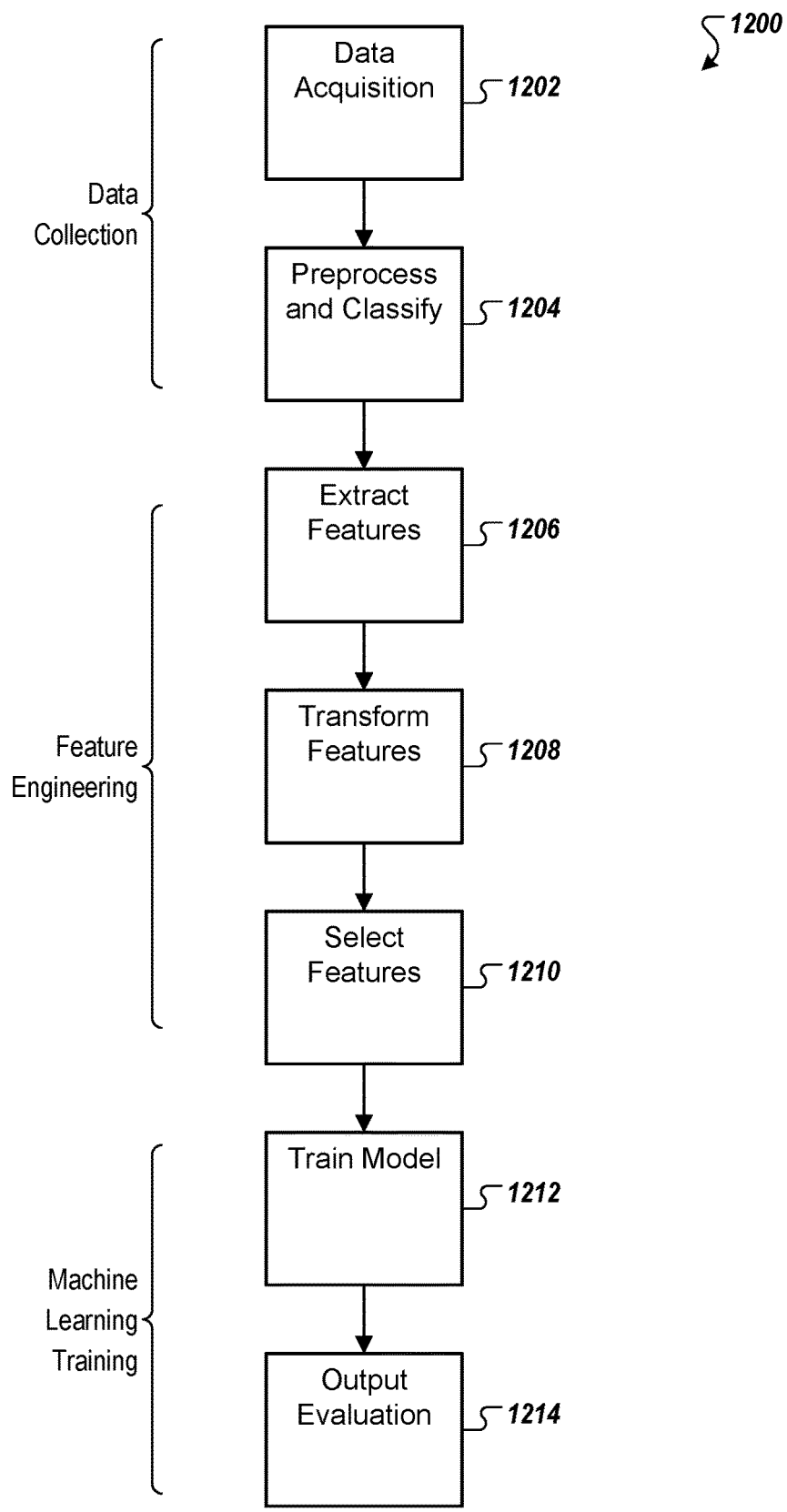
FIG. 12 shows an example process that can be used to produce classifiers able to evaluate subject data and generate stimulus to a subject based on determined timings of electrophysiological events of the subject.

FIG. 12 shows an example process that can be used to produce classifiers able to evaluate subject data (e.g., sleep data) and generate stimulus to a subject based on determined timings of electrophysiological events of the subject. For example, the process 1200 can be performed by the elements of the system 1100 and will be described with reference to those elements. However, other systems can be used to perform the process 1200 or similar processes.

Generally speaking, the process 1200 includes data collection 1202-404, feature engineering 1206-410, and machine learning training 1212-414. In the data collection 1202-404, data is gathered in formats in which it is generated or transmitted, then reformatted, decorated, aggregated, or otherwise processed for use. In the feature engineering 1206-410, data is analyzed to find those portions of the data that are sufficiently predictive of a physiological function (e.g., brain function) to be used to train the classifiers. This can allow the discarding of extraneous or unneeded data, improving computational efficiency and/or accuracy. The machine learning training 1212-414 can then use those features to build one or more models that characterize relationships in the data for use in future classifications.

In the data acquisition 1202 for example, the computing hardware 1110 can collect data from the sensors 1104, from the user interface 1106, and the tagging data 1108. As will be understood, this acquisition may happen over various lengths of time and some data may be collected after other data is collected.

In the preprocessing and classifying 1204 for example, the computing hardware 1110 can perform operations to change the format or representation of the data. In some cases, this may not change the underlying data (e.g., changing integers to equivalent floating point numbers, marking epochs of time in time-series data), may destroy some underlying data (e.g., reducing the length of binary strings used to represent floating point numbers, applying filters to time-series data), and/or may generate new data (e.g., averaging two prefrontal EEG channels such as Fp1 and Fp2 to create a single, virtual prefrontal EEG signal; mapping annotations to the data).

In the feature extraction 1206 for example, the computing hardware 1110 can extract features from, e.g., fiducial points recorded in the processed and classified data. Some of these features can be related to SOs of EEG signals. For example, individual waves can be isolated, tagged with timing data, and various features of wave morphology can be annotated. These waves can be filtered (e.g., removing anomalous waves) and aggregated into representative samples (e.g., by taking a weighted or unweighted average of various values), with one such example shown in FIG. 11B. Fiducial points can be identified according to heuristic rules applied to the morphology or local shape of various points of the wave data. For example, a rule for generating a neg_time tag may be to identify a minimum value in the wave as neg_time.

One example scheme of fiducial points is as follows. Various other SO fiducial points (or features) can also be defined, e.g. the points at which EEG signal value exceeds a defined percentage of the SO negative peak amplitude, either in the negative or the positive direction.

Zx1 can be defined as timing of the first positive-to-negative zero-crossing in the real-time filtered EEG signal, for a given SO Steady1 can be defined as timing of the point after zx1 at which the EEG signal slope exceeds in negativity a predefined negative slope threshold Neg_time can be defined as timing of the SO negative peak Neg_val can be defined as the amplitude of the SO negative peak Steady2 can be defined as timing of the point before zx2 at which the EEG signal slope exceeds in positivity a predefined positive slope threshold Zx2 can be defined as timing of the first negative-to-positive zero-crossing in the real-time filtered EEG signal, for a given SO Features 1-7 in FIG. 11B can be used to record the time (e.g., in milliseconds), or the difference in EEG amplitude (e.g., in microvolts) between various fiducial points and features in the wave as shown.

In the feature transformation 1208 for example, the computing hardware 1116 can modify the features in ways that preserve all data, destroy some data, and/or generate new data. For example, values may be mapped to a given scale (e.g., mapped to a log scale, mapped to scale of 0 to 1). In some cases, statistical aggregates can be created (e.g., mean values, standard variation). These aggregates may be generated from data for each sleep session, across the detected sleep stages, or may aggregate data across multiple sleep sessions.

In the feature selection 1210 for example, the computing hardware 1116 can select some of the features for use in training the model. This can include selecting a proper subset (e.g., some, but not all) of the features.

In particular, some wave data can be tagged for use in training, and some wave data can be tagged for exclusion from training. In some instances, some waves can exhibit morphology consistent with 'typical' or 'normal' brain activity while some waves can exhibit morphology that is not consistent with 'typical' or 'normal' brain activity. These waves are sometimes referred to as "well-behaved" and "poorly-behaved". As such, waves can be tagged with an inclusion/exclusion tag to designate if the wave should be used or excluded from model training and/or model deployment (e.g., preventing stimulation when such a SO wave is observed).

As will be appreciated, "poorly-behaved" waves may be the product of noisy data collection by sensors. Additionally or alternatively, the "poorly-behaved" waves may be the product of accurate sensing of atypical—but potentially normal and healthy—brain activity that does not conform to typical SO wave morphology or patterns. Regardless of the cause, these "poorly-behaved" waves tagged for exclusion can be handled as having low predictive value and excluded from model training, while the "well-behaved" waves tagged for inclusion can be handled as having high predictive value and included in model training.

In the model training 1212 for example, the computing hardware 1116 can train one or more machine-learning models using the selected features (e.g., wave data marked for inclusion and excluding wave data marked for exclusion). In some cases, one or more models are created that propose mappings between the features and tagged data indicating timing of features (e.g., in milliseconds from the onset of a particular wave) for those features. Then, the computing hardware 1116 modifies those mappings to improve the model's accuracy.

In the output evaluation 1214 for example, the computing hardware 1116 can generate one or more functions, sometimes called classifiers, which include a model. This inclusion can involve including the whole model, or may involve only including instructions generated from the model allowing for the classifier to have a smaller memory footprint than the model itself.

Described now will be one example implementation of the process 1200. While a particular number, type, and order of details are selected for this implementation, it will be understood that other numbers, types, and order of details may be used to implement the process 1200 or other processes that accomplish the same goals.

In the data acquisition 1202 in this implementation, basic information about a subject can be acquired such as one or more of a subject's: name or identification (ID), age, gender, other sociodemographic data, health-related information, physiological information (e.g., menopausal status and menstrual cycle information), and information related to lifestyle or behaviors (including but not limited to sleep habits, tobacco/alcohol consumption, exercise, meditation, among others). This data can be user inputted or integrated from other devices.

The system(s) described above can enable the real-time open-loop or closed-loop delivery of stimuli, which include at least one or more of audio, light, vibratory, or electrical stimuli, as part of the data acquisition procedure.

The subject's raw biological information can be collected, which can include of at least one or more sleep recordings where each recording includes at least one prefrontal EEG channel and can include additional sensors such as: additional EEG channels, forehead photoplethysmogram (PPG), blood oxygen saturation ($SpO_2$), EMG, EOG, electrodermal activity (EDA), and actigraphy (movement) sensors. In some cases, systems can use two prefrontal EEG channels (Fp1 and Fp2), with or without PPG, $SpO_2$, and actigraphy. The data can be collected from full night recordings and/or less-than full nights (e.g., naps).

The output of the data acquisition 1202 can include each subject's raw biological signals and stimulus types and timings, from one or multiple recordings, as well as the subject's age and other basic information.

In the preprocessing and classifying 1204 in this implementation, preprocessing and automated sleep-stage classification can include various operations that may be performed on the output of the data acquisition 1202. For example, two bandpass-filtered (0.2-40 Hz) prefrontal EEG signals are averaged to obtain a single virtual prefrontal EEG channel. Heartbeat times are extracted from the filtered and demodulated PPG signal using peak detection.

The data is segmented into discrete overlapping and/or non-overlapping epochs and each epoch is described using a set of time-domain, frequency-domain and other EEG and HRV features typically used for sleep stage classification. Each epoch is classified as either wakefulness (W), rapid eye movement (REM) sleep, non-REM sleep stage 1 (N1), non-REM sleep stage 2 (N2), or deep sleep (N3), using an automatic sleep stage classification algorithm based on machine learning (ML) and the extracted sleep EEG features.

Each epoch can be annotated as containing a SO wave, containing the beginning of such a wave (e.g., containing zx1), and/or containing other fiducial points of a wave. This annotation may in some cases be automated for example with offline (e.g., after all data is gathered and after the sleep session has ended) analysis or online (e.g., during the sleep session, for past SOs) analysis. This annotation may in some cases be manual, with a technician reviewing and tagging the data. This annotation may in some cases be automated, with a computational analysis being performed using a pre-defined ruleset to annotate the data. This annotation may in some cases be a mix of manual and automated operations.

The output of the preprocessing and classifying 1204 can include each subject's preprocessed biological data, from one or multiple recordings, segmented into time-based epochs. For example, the time-based epochs can be segmented into epochs corresponding to the length of a single SO wave (e.g., 250 to 300 milliseconds in one example).

In the feature extraction 1206 in this implementation, SO wave features are computed. These features may be recorded, for example, in a count of milliseconds from the onset of the given wave, in distances (in time) between fiducial points, in amplitudes or maximum or minimum values, etc.

The output of the feature extraction 1206 can include each of the subject's recordings, either one or multiple, described with an array of wave features, as well as EEG-based, HRV-based and $SpO_2$-based sleep microstructure features.

In the feature transformation 1208 in this implementation, the computed features are transformed using lossy or lossless data compression for advantageously efficient storage and transmission.

In the feature selection 1210 data for various SO waves of various demographics and SO wave types are examined to be tagged for inclusion or exclusion in model training. In some examples, a reference wave is defined which exhibits morphology of SO waves identified as "typical" or otherwise highly predictive. A difference value for each candidate wave is then calculated to represent a measure of difference between the candidate wave and the reference wave. Candidate waves with a difference value less than a threshold value can be marked for inclusion, while waves with a difference value greater than the threshold value can be marked for exclusion. In some cases, candidate waves can be defined based on rules created by a human user or generated from automated analysis of wave data (e.g., clustering analysis).

In the model training 1212 in this implementation, a final set of all wave data marked for inclusion is used to train the prediction model. The model hyperparameters are determined using a non-convex optimization algorithm (e.g., the Bayesian optimization algorithm), with the goal of optimizing the average model performance in repeated k-fold cross-validation. Multiple approaches are possible: classical regression; regression with a custom loss function, classification approach, etc.

In the output evaluation 1214 in this implementation, output of the model is evaluated on new SOs which were not used in the training. The subject's SO wave features are calculated according to steps 1202-408, and a set of ground-truth annotated SO wave features are created as a ground truth for this analysis. If the calculated and manual SO wave features are similar enough, the model passes the output evaluation.

Figure 13:
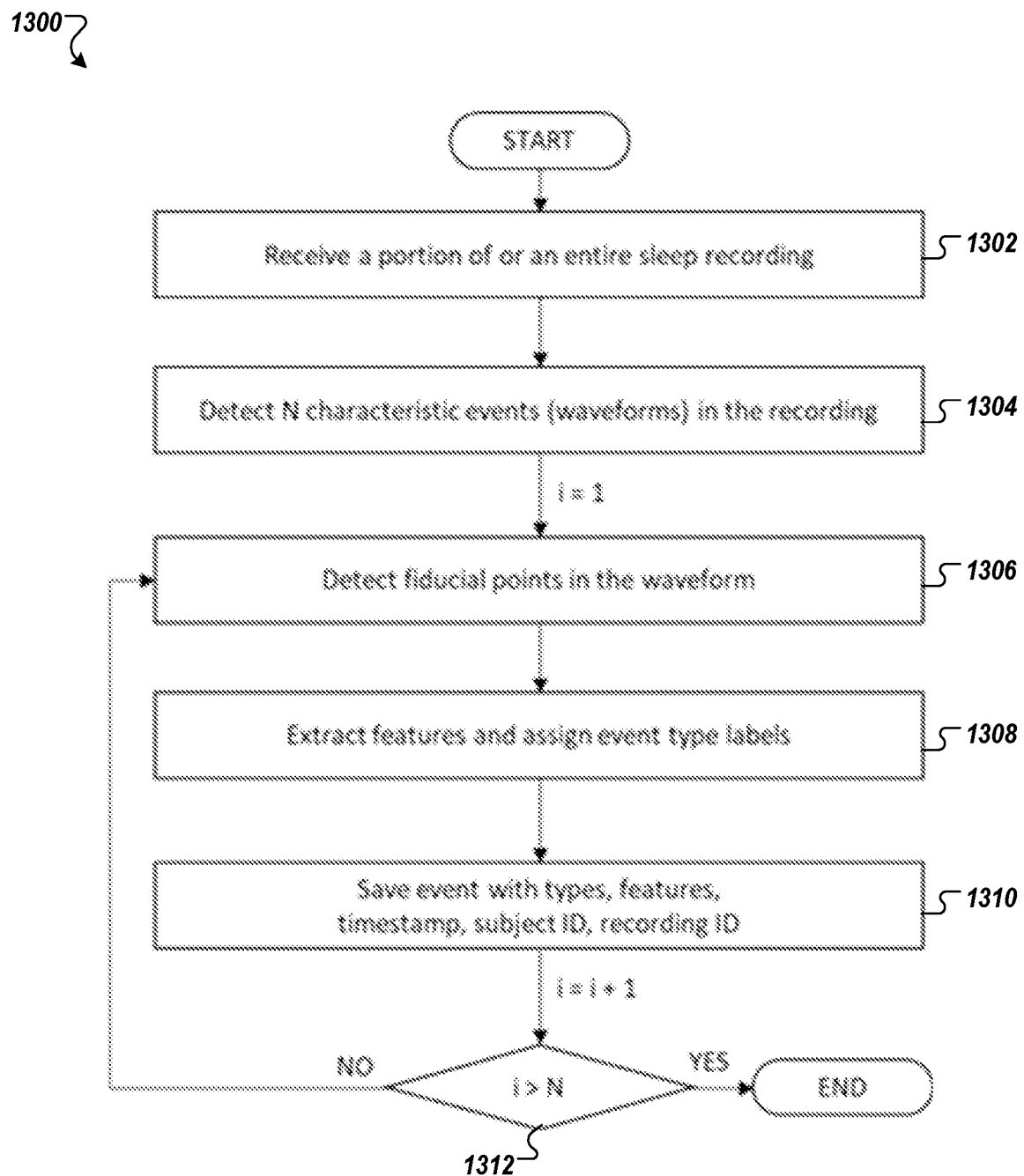
FIG. 13 shows an example process that can be performed by the system.

FIG. 13 shows an example process 1300 that can be performed by the system 1100. For example, the process 1300 can be performed to process a portion of, or an entire, sleep recording and storing the resulting data for offline or real-time analysis.

In the process 1300, data of a portion or entire sleep session is received 1302. For example, a headband worn by a subject is used to generate EEG data while the subject is sleeping. N characteristic events such as waveforms are detected 1304 in the data. Fiducial points are identified 1306 in a waveform, for example to mark a point of measurement within the waveform. Features are extracted and labels are assigned to events 1308 in a waveform, for example finding a difference in timing of various fiducial points. Event data is saved 1310 to record information such as types, fiducial points, features, timestamps, subject identification (ID) data, recording ID data, etc. 1306-1310 can be repeated for each of the N events.

Figure 14:
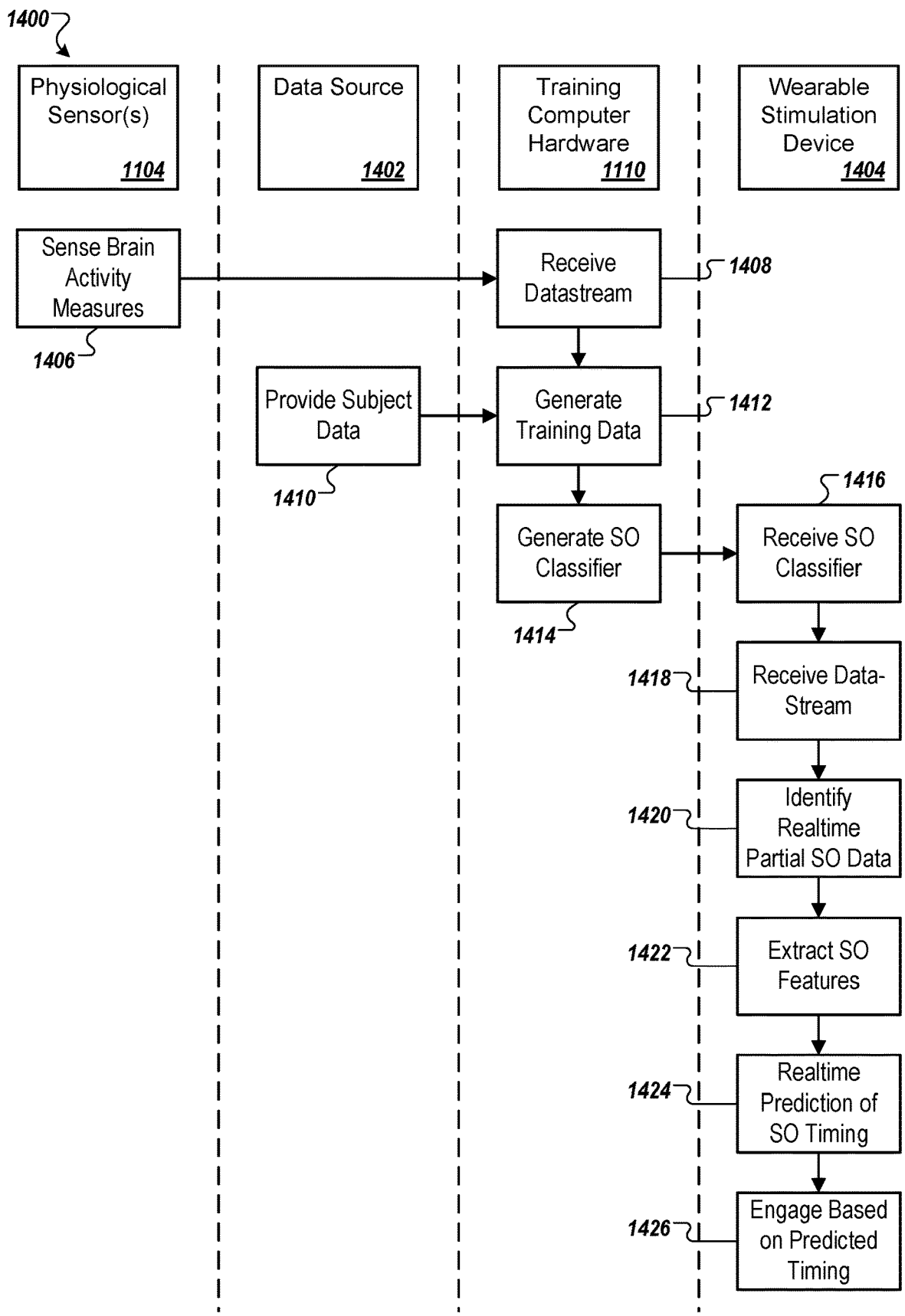
FIG. 14 shows an example process for generating stimulus to a subject based on determined timings of electrophysiological events of the subject.

FIG. 14 shows an example process 1400 for generating stimulus to a subject based on determined timings of electrophysiological events of the subject. The process 1400 can be performed, for example, by the physiological sensors 1104, a data source 1402, the training computer hardware 1110, and a wearable stimulation device 1404 (e.g., data acquisition device 1001 that includes at least one stimulation device such as sound wave generator 1017), though other components may be used to perform the process 1400 or other similar processes.

The physiological sensors 1104 sense brain activity measures 1406 and the training computer hardware 1110 can receive data-streams from the sensors 1104. For example, training subjects can be identified and given a head-worn device with one or more sensors 1104 to wear while they sleep. EEG data, or data used to generate EEG data, is sensed from the training subjects and used by the training computer hardware 1110.

One or more data sources 1402 provide 1410 subject data. For example, metadata for the EEG data can be stored and provided by the data source 1402. This metadata can include information about the subject (e.g., demographic data, records of informed consent), tagging data created after the EEG data is generated and stored to disk (e.g., well after the training subject's sleep session has ended), or other appropriate data.

The training computer hardware 1110 can generate 1412 training data. For example, EEG data and subject data can be aggregated to match relevant EEG data with corresponding subject data. Epochs of the EEG data can be identified and examined to identify waveforms that conform to target-waveforms, with waveforms lacking sufficiently similar morphology excluded from the training data, etc. Features of the morphology (or other properties, e.g., frequency-domain properties) of the waves can be generated according to a ruleset stored in computer memory and applied to a waveform.

The training computer hardware 1110 can generate 1414 one or more SO classifiers with the training data. For example, a machine-learning model can be given, as input, a subset of early features of a waveform and given, as target output (e.g., a point of decision value), the later (e.g., occurring after a defined point of decision) features of the waveform, and the model can be trained to identify relationships between the input and output data.

A wearable stimulation device (and/or related controlling computer hardware) 1404 can receive 1416 the SO classifier. For example, a user of the device 1404 may set up a user profile and provide their demographic information, and a demographically-matched or subject-specific classifier can be accessed and used for that user.

The wearable stimulation device 1404 receives 1418 a data-stream for the subject. For example, the data-stream can include a real-time EEG signal generated by one or more EEG sensors of the device 1404. As the subject wears the device 1404 and sleeps, the EEG sensors can gather data of ongoing brain activity of the subject within a single sleep session.

The wearable stimulation device 1404 identifies 1420 real-time data recording a partial SO (e.g., the start of the SO up to the point of decision as defined by a particular classifier). For example, the user may be sleeping and experiencing a SO. At the beginning of the SO, the device 1404 can identify the start of the SO based on the EEG data and mark that as time=0 for that SO. Before the end of that SO, the EEG will therefore record an incomplete SO of the ongoing brain activity.

Figure 11C:
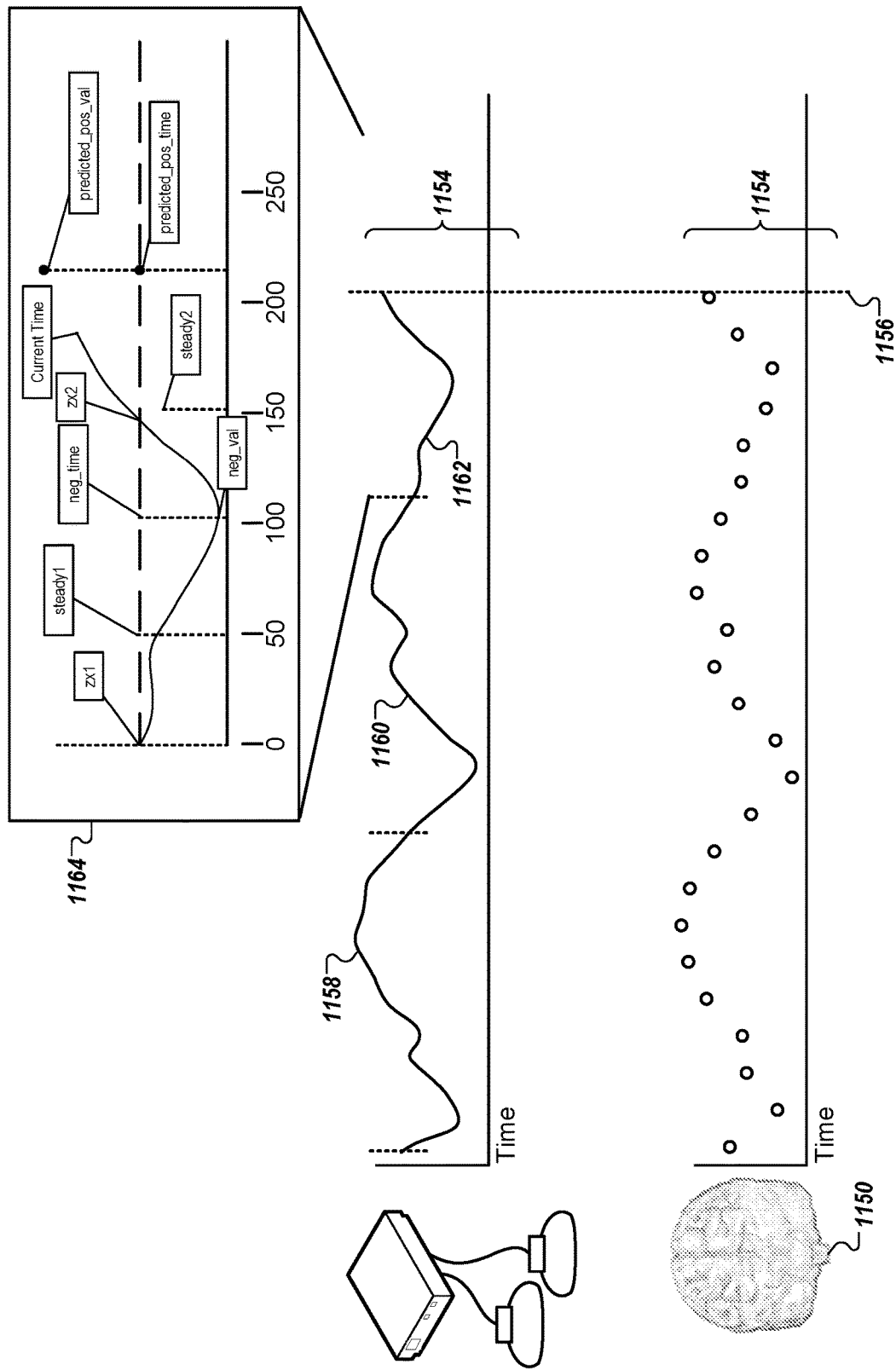

Waveform detection (e.g. detection of recordings of a partial SO from real-time data) can be conducted using specific criteria on amplitudes and durations which can be determined from the fiducial points of the detected waveform (see, e.g., FIG. 11C). These criteria form rules that define a waveform to be detected in real-time, and are adjusted to the properties of the real-time signal, either manually or by automated processes. In many cases waveform does not have the same morphology in the offline-filtered signal (the ground-truth morphology) as it has in the real-time-filtered signal with phase/amplitude filter distortions. Therefore, real-time waveform detection rules can be optimised to achieve highest real-time detection accuracy of waveforms which are annotated using an offline-filtered signal.

The wearable stimulation device 1404 extracts 1422 SO features for the SO. For example, before the end of the SO, while the subject is experiencing the SO, the device 1404 can identify one or more timestamps of one or more features (e.g., some, but not all, of the features shown in FIG. 11B). These features may be identified by a number of milliseconds after the time=0 point discussed previously, or by another technologically-appropriate scheme.

In some cases, the SO features that are extracted are created using one or more fiducial points selected from the group (SO Group) consisting of i) a positive-to-negative zero-crossing (zx1), ii) a negative-to-positive zero-crossing (zx2), iii) a point after zx1 at which a slope of the data-stream falls under a negative threshold (steady1), iv) SO negative peak timing (neg_time), v) a point before zx2 at which the data-stream falls under a defined positive threshold (steady2), vi) a SO positive peak timing (pos_time), and vii) a points at which data-stream value exceeds a defined percentage of the SO negative peak amplitude (neg_percent). In some cases, the features are measures of timing or EEG signal value differences of two fiducial points. In some cases, a fiducial point may be used as a feature. As will be appreciated, the SO features may be fewer than these features, and/or may include other features.

The wearable stimulation device 1404 determines 1424, in real-time, one or more predicted SO timings. For example, before this SO is completed, the device 1404 can generate a prediction of a time point for an as-of-yet not experienced or sensed feature or target morphology of the waveform. In some cases, this predicted SO timing is selected from the SO Group. In some cases, this predicted SO timing is different than the SO Group.

To create the predicted SO timings, the device 1404 can submit, to the SO classifier, the already-sensed features of the SO before the SO ends, while the SO is ongoing, concurrent with the subject experiencing the SO. As described in this document, the SO classifier can be created by use of training on a dataset of training-SO and matching training-SO timings (e.g., 1406-612).

The wearable stimulation device 1404 engages 1426 a stimulation based on the predicted SO timing. For example, the device 1404 can engage the stimulation to provide the subject with a stimulation signal at the predicted SO timing so that the signal is received by the subject while the brain activity of the subject is still generating the same SO as has been discussed in 1420. As will be appreciated, the process 1426 can include determinations, for a given SO, to or not to engage stimulation. That is to say, the process 1426 can determine i) to stimulate and ii) when to stimulate, or can determine i) not to stimulate in which case ii) no stimulation timing need be determined for that SO. This technology may be configured to account for previous stimulation determinations when determining an upcoming stimulation timing. For example, the threshold to determine not to stimulate may begin at a lower value (e.g., 0.6) and increase for each sequential determination to stimulate (e.g., by 0.05) to a maximum value (e.g., 0.8). By use of such a scheme, the threshold to skip a stimulation is lower when a sequence of recent stimulations were provided, but higher to skip a stimulation if no stimulation has been provided recently.

In some cases, engaging the stimulation signal involves calculating a delay interval to account for, for example, hardware delay, estimated real-time filtering delay, etc. This can include determining a delay interval based on the predicted SO timing within a waveform (e.g., at time=973) minus the current time in the waveform (e.g., at time 933, for a difference of 120). Then, after delaying for the time interval (e.g., 40 milliseconds) from the completion of the calculation, sending an activation command to the stimulation device.

In some cases, engaging the stimulation signal involves determining if a waveform is an atypical waveform and refraining from engaging the stimulation for that waveform. In some cases, engaging the stimulation signal involves determining that a waveform is a typical waveform and engaging the stimulation for the waveform responsive to determining that the waveform is a typical waveform.

With the method 1400, real-time stimulation of a sleeping subject can be supplied relative to an ongoing SO event. This can allow for superior stimulation timing, providing stimulation to improve the health, wellness, or other function of the subject. Because the prediction can be performed in much less time than the length of time that a given SO takes, the beginning portion of a SO can be used to predict timing of later portions of the SO when stimulation is to be provided. As will be appreciated, this is an advantage compared to other systems in which historical SO or EEG data is used to retrodict (sometimes called a postdiction) timing of events that are already experienced, recorded, saved to disk, and only then analyzed.

As previously described, the use of a brain age metric (or another metric that measures brain function can be combined with these techniques to delivery stimulation. Some examples of such a combination are described here.

Neurostimulation can be applied to enhance brain function, which can be measured using the brain age metric. For example, a baseline brain age metric can be collected for a subject before treatment (e.g., at Time=$T_0$). Then neurological stimulation can be applied using the timing determinations described above to rejuvenate brain function(s) activated in slow-wave sleep such as memory consolidation, processing speed, hormone activation, glymphatic flow (clearing toxic metabolic byproducts) and HRV (mood, interpersonal relationships). After treatment (e.g., after a single stimulation exposure in one sleep session, after a course of treatment over many sleep sessions), a post-treatment brain age metric can be collected at a later time (e.g., at Time=$T_1$). Then, depending on the outcome, the same treatment can be continued, treatment can be modified, etc. and subsequent brain age metrics can be collected (e.g., at Time=$T_2, T_3, T_4 \ldots T_N$).

In some cases, audio stimulation can be combined with other therapeutics (e.g., drug therapy) to enhance the efficacy. In some cases, Schizophrenia, believed to be associated with spindle deficit, can be treated with drugs and audio stimulation to enhance spindle activity and accelerate the treatment compared to drug treatment alone.

In some cases, TBI patients can be treated with combination of audio stimulation and drug therapy. It is believed that TBI patients suffer from poor synchronization between SOs and spindles. Therefore, audio stimulation can work in conjunction with drug treatment to enhance spindle coupling and accelerate recovery.

In some cases, audio stimulation can be used to alleviate side effects of a given medication or disease. As will be appreciated, many mental disorders and their traditional drug therapies can produce unwanted side effects that either reduce the quality of life of the patients, or cause them to halt the drug therapy because they perceive the side effects to be worse than the condition being treated. Use of audio stimulation, even if not used to treat the mental disorders itself, it could have a tremendous impact on the quality of life for individuals with these disorders by reducing the side effects discussed above. By reducing the side effect of a drug with audio stimulation, a patient may be able to tolerate the drug where they would not be able to otherwise. Some of the symptoms and side effects that can be reduced include, but are not limited to, impaired memory, reduced HRV, increased sympathetic nervous system, elevated cortisol levels, chronic inflammation, decreased immune response, fatigue, and increased insulin resistance. Audio stimulation provided with technology described in this document can be beneficial for each of these.

Brain age metrics can be used for diagnostics and risk assessments. For example, by using brain function assessments and pattern recognition of unique brain wave characteristics (e.g. changes in sleep architecture, sleep spindle deficits, SO-Spindle coupling) clinicians can perform earlier diagnosis or assess severity of various conditions. Examples of these conditions include, but are not limited to, the following. Pre-symptomatic risk assessment for mild cognitive impairment (MCI) or Alzheimer's Disease may be performed. Audio stimulation can be used by early stage MCI patients to slow degradation in brain signalling/communication (i.e. SO-spindle coupling). For TBI patients, loss of synchronization (i.e. poorer SO-spindle coupling) is common. Therefore, a brain age metric can be used as a diagnostic to measure severity of TBI. For example, severe changes in brain age and brain age explanations (e.g., SHapley Additive exPlanations or SHAP) in post vs. pre injury. Audio stimulation of SWS can enhance neuronal communication and restore synchronization between the hippocampus and prefrontal cortex.

For Long COVID patients, objective measure of brain function can be used to assess presence or severity of Long COVID's brain fog. Furthermore, recovery of these symptoms can be accelerated with audio stimulation.

Early pre-symptom detection, risk detection, and diagnosis can be performed for many diseases, e.g., mild cognitive impairment (MCI), pre-symptomatic Alzheimer's disease (AD), or Schizophrenia. For example, prodromal Schizophrenia can be identified with this technology based on objective measures, even before the subject is aware of the symptoms or before the symptoms have any noticeable impact on their quality of life. Schizophrenia (and other diseases) have unique brain wave characteristics (e.g. sleep spindle deficits) which can be identified with this technology. By performing objective diagnostics, Schizophrenia can be detected early in subjects where subjective diagnostic criteria is likely to miss the symptoms for diagnosis. For example, a patient with excellent executive function and a robust support structure may mask or camouflage symptoms—even from themselves—in the early stages of the disease. By earlier diagnosis with this technology treatment can be delivered to slow or halt the progression before it does impact the subject.

This technology can be used to measure the impact of an intervention or combination of interventions. For example, this technology is able to provide an assessment that is specific enough to measure the impact of various treatments such as lifestyle changes, behavioral choices, medical management (managing hypertension, diabetes, etc.) on brain age.

Bi-directional relationships between sleep and medical conditions can be measured. Said another way, this technology can be used to create a virtuous cycle of reducing a symptom that impairs sleep, allowing for more sleep causing for better outcomes of the disease that was impairing sleep in the first place. For example, enhancing SWS can help address the negative symptoms of diseases (cognitive deficits associated with schizophrenia and depression, improved HRV), and improved disease states can enhance the brain age metric for a subject. Enhanced SWS can then result in the reduction of medical comorbidities of mental illness, inflammation, stress, etc., that lead to premature death and neurodegeneration.

Example embodiments include:
1. A method for providing stimulation to a subject, the method comprising:
   receiving a data-stream for the subject, the data-stream comprising a real-time EEG signal generated by one or more EEG sensors gathering data of ongoing brain activity of the subject;
   identifying in the data-stream a record of a current slow oscillation (SO) that contains data of an incomplete SO of the ongoing brain activity;
   extracting one or more SO features for the current SO from the record of the current SO;
   determining, from the SO features, one or more predicted SO values, the predicted SO values each being a prediction of a future event at which the current SO will exhibit a target morphology.
2. The method of embodiment 1, wherein the method further comprises:
   engaging a stimulation device to provide the subject with a stimulation signal based on the predicted SO values such that the subject receives the stimulation signal while the brain activity of the subject is generating the current SO.
3. The method of embodiment 2, wherein engaging the stimulation device comprises:
   determining a delay interval based on the predicted SO values;
   delaying for the delay interval; and
   sending an activation command to the stimulation device upon expiration of the delay interval.
4. The method of embodiment 2, wherein engaging the stimulation device comprises determining that the current SO is a typical SO.
5. The method of embodiment 1, wherein the one or more SO features that are extracted are selected from the group (SO Group) consisting of i) a positive-to-negative zero-crossing (zx1), ii) a negative-to-positive zero-crossing (zx2), iii) a point after zx1 at which a slope of the data-stream falls under a negative threshold (steady1), iv) SO negative peak timing (neg_time), v) a point before zx2 at which the data-stream falls under a defined positive threshold (steady), vi) a SO positive peak timing (pos_time), and vii) a points at which data-stream value exceeds a defined percentage of the SO negative peak amplitude (neg_percent).
6. The method of embodiment 5, wherein the one or more predicted SO values are also selected from the SO Group.
7 The method of embodiment 5, wherein the one or more SO values are different than the SO Group.
8. The method of embodiment 2, wherein determining, from the SO features, one or more predicted SO values comprises submitting, to a SO-classifier, the SO features and receiving the predicted SO values.
9. The method of embodiment 8, wherein the SO-classifier produces a point of decision.
10. The method of embodiment 8, wherein the SO-classifier is created via training on a dataset of training-SO features and matching training-SO values.
11. The method of embodiment 8, wherein the dataset is constructed to exclude atypical training-SO features.
12. The method of embodiment 8, wherein the classifier is retrained using the SO features of a single night's sleep during the single night's sleep.
13. The method of embodiment 8, wherein the classifier is trained for a specific morphological type of SO.
14. The method of embodiment 8, wherein the classifier is trained for the subject using training data from the subject.
15. The method of embodiment 8, wherein the classifier is trained in real-time using the data from a current sleep session.
16. The method of embodiment 1, wherein determining of one or more predicted SO values is responsive to determining that the subject is in a particular sleep stage
17. A system for providing stimulation to a subject, the system comprising:
   a data acquisition device comprising a body, one or more EEG sensors, and at least one stimuli generator;

one or more processors; and
memory storing instructions that, when executed by the processors, cause the processors to perform operations comprising:
receiving a data-stream for the subject, the data-stream comprising a real-time EEG signal generated by the one or more EEG sensors gathering data of ongoing brain activity of the subject;
identifying in the data-stream a record of a current slow oscillation (SO) that contains data of an incomplete SO of the ongoing brain activity;
extracting one or more SO features for the current SO from the record of the current SO;
determining, from the SO features, one or more predicted SO, the predicted SO timings each being a prediction of a future time at which the current SO will exhibit a target morphology.

18. The system of embodiment 16, wherein the body is a headband that includes a curved shape that is configured to extend around each ear of a subject and under a nape of the back of a subject's head.

19. The system of embodiment 16, wherein the operations further comprise:
engaging the at least one stimuli generator to provide the subject with a stimulation signal at the predicted SO values such that the subject receives the stimulation signal while the brain activity of the subject is generating the current SO.

20. The system of embodiment 16, wherein the stimuli generator generates audio stimuli.

21. The system of embodiment 16, wherein determining, from the SO features, one or more predicted SO values comprises submitting, to a SO-classifier, the SO features and receiving the predicted SO values.

22. The system of embodiment 16, wherein the one or more SO features that are extracted are selected from the group (SO Group) consisting of i) a positive-to-negative zero-crossing (zx1), ii) a negative-to-positive zero-crossing (zx2), iii) a point after zx1 at which a slope of the data-stream falls under a negative threshold (steady1), iv) SO negative peak timing (neg_time), v) a point before zx2 at which the data-stream falls under a defined positive threshold (steady), vi) a SO positive peak timing (pos_time), and vii) a points at which data-stream value exceeds a defined percentage of the SO negative peak amplitude (neg_percent).

Although a few implementations have been described in detail above, other modifications are possible. Moreover, other mechanisms for performing the systems and methods described in this document may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A system for use in determining metrics of a subject, the system comprising:
one or more processors; and
memory storing instructions that, when executed by the one or more processors, cause the one or more processors to perform operations comprising:
receiving physiological measures of brain activity of the subject recorded at least partly while the subject is asleep;
receiving demographic data for the subject, the demographic data comprising a chronological age for the subject when the physiological measures were recorded;
generating, using the physiological measures and from the demographic data, segmented training-data that specifies a plurality of epochs of time, and data for the subject in each epoch;
generating, using the segmented training-data, sleep-structure features for the subject;
selecting a subset of the sleep-structure features as selected features;
generating one or more function-metric classifiers using the selected features, comprising training a model that defines at least one relationship between the physiological measures and the chronological age, the function-metric classifier configured to:
receive, as input, new physiological measures of the subject; and
provide, as output, a function-metric value determined based on the defined relationship between the new physiological measures and the chronological age, the function-metric value comprising a variance-from-chronological-age value that comprises an indication of the subject's brain function as compared to the subject's expected brain function based on the subject's chronological age.

2. The system of claim 1, wherein the demographic data further comprises at least one of the group consisting of an identifier, a gender, sociodemographic data, medical data, behavioral data, and lifestyle data that have been entered by the subject into an input device of the system.

3. The system of claim 1, wherein the physiological measures of the subject comprise at least one of the group consisting of a frontal electroencephalography (EEG) channel, two EEG channels, forehead photoplethysmography (PPG), blood oxygen saturation (SpO2), electromyography (EMG), electrooculography (EOG), electrodermal activity (EDA), and actigraphy data.

4. The system of claim 1, wherein:
the physiological measures of the subject were recorded at least partly while the subject is asleep and provided with at least one stimuli of the group consisting of audio stimuli, light stimuli, vibratory, electrical stimuli, open-loop stimuli, and closed-loop stimuli; and
the physiological measures comprising timing info defining timing of the stimuli provided to the subject.

5. The system of claim 1, wherein generating, using the physiological measures and from the demographic data, the segmented training-data comprises:
applying band-pass filters to at least some of the physiological measures comprising at least two EEG signals and at least one PPG signal;
combining at least two of the at least two EEG signals to create a virtual EEG signal;
extracting heartbeat times from the at least one PPG signal by detecting peaks in the at least one PPG signal;
segmenting the physiological measures into the plurality of epochs of time;
generating, for each epoch of time, at least one of the group consisting of multiple time-domain features, frequency domain features, and nonlinear or complex signal descriptives; and
accessing tagging data that tags each epoch of time with a sleep stage from the group consisting of wakefulness, rapid eye movement (REM) sleep, non-REM sleep stage 1 (N1), non-REM sleep stage 2 (N2), non-REM sleep stage 3 (N3), and non-REM sleep stage 4 (N4).

6. The system of claim 1, wherein generating, using the segmented training-data, the sleep-structure features for the subject comprises:
   determining macrostructure features for the subject describing at least one of the group consisting of sleep-stage duration, sleep-stage percentage, sleep-stage transition probability, sleep fragmentation, and awakenings;
   determining microstructure features for the subject describing at least one of the group consisting of stage-specific EEG features, waveform-specific EEG features, and stimulus-response EEG features;
   determining cardiac features for the subject using at least one of the group consisting of i) heartbeat times and ii) tagging data that tags epochs of time in the segmented training-data with sleep stage; and
   determining respiratory features for the subject describing at least one of the group consisting of blood oxygenation, and sleep apnea, using at least one of the group consisting of blood oxygen saturation (SpO2) and the tagging data.

7. The system of claim 1, wherein selecting the subset of the sleep-structure features as the selected features comprises:
   transforming at least one of a plurality of features selected from the group consisting of macrostructure features, microstructure features, cardiac features, and respiratory features; and
   aggregating the sleep-structure features from multiple sleep-sessions.

8. The system of claim 1, wherein selecting the subset of the sleep-structure features as the selected features comprises:
   identifying the subset of the sleep-structure features as those features most predictive of the chronological age.

9. The system of claim 1, wherein selecting the subset of the sleep-structure features as the selected features comprises sequentially calculating a cross-validated mean absolute error (MAE) with a regression model, wherein the regression model is an extreme learning machine (ELM) regressor.

10. The system of claim 1, wherein training the model that defines the at least one relationship between the physiological measures and the chronological age comprises determining hyperparameters for the model using a Bayesian optimization algorithm targeting a repeated k-fold cross-validation using at least one of the group consisting of a first regression; a second regression with a loss function based on a residual-label covariance analysis, and a deep label distribution algorithm.

11. The system of claim 1, wherein training the model that defines the at least one relationship between the physiological measures and the chronological age comprises refining the model to reduce age-dependent bias.

12. The system of claim 1, wherein the function-metric value further comprises at least one of the group consisting of a model interpretation, an interpretation of the model's output, a human-readable instruction displayable to a user of an output device, and an automation-instruction that, when executed by an automated device causes the automated device to actuate.

13. The system of claim 1, wherein the operations further comprise distributing the function-metric classifiers to a plurality of user devices that are configured to sense new physiological measures of other subjects at least partly while the other subjects are asleep.

14. A system for use in determining metrics of a subject, the system comprising:
   one or more processors; and
   memory storing instructions that, when executed by the one or more processors, cause the one or more processors to perform operations comprising:
      receiving physiological measures of brain activity of the subject recorded at least partly while the subject is asleep;
      receiving demographic data for the subject, the demographic data comprising a chronological age for the subject when the physiological measures were recorded;
      generating, using the physiological measures and from the demographic data, segmented training-data that specifies a plurality of epochs of time, and data for the subject in each epoch;
      generating, using the segmented training-data, sleep-structure features for the subject;
      selecting a subset of the sleep-structure features as selected features;
      generating one or more function-metric classifiers using the selected features, comprising training a model that defines at least one relationship between the physiological measures and the chronological age, the function-metric classifier configured to:
         receive, as input, new physiological measures; and
         provide, as output, a function-metric value determined based on the defined relationship between the new physiological measures and the chronological age; and
      estimating a predicted function-metric for the subject to represent a measure of predicted future physiological measures based on an expected change to the brain activity of the subject due to advancing in chronological age.

15. A system for use in determining metrics of a subject, the system comprising:
   one or more processors; and
   memory storing instructions that, when executed by the one or more processors, cause the one or more processors to perform operations comprising:
      receiving physiological measures of brain activity of the subject recorded at least partly while the subject is asleep;
      receiving demographic data for the subject, the demographic data comprising a chronological age for the subject when the physiological measures were recorded;
      generating one or more function-metric classifiers using selected features, comprising training a model that defines at least one relationship between the physiological measures and the chronological age, the function-metric classifier configured to:
         receive, as input, new physiological measures; and
         provide, as output, a function-metric value determined based on the defined relationship between the new physiological measures and the chronological age, the function-metric value comprising a variance-from-chronological-age value that comprises an indication of the subject's brain function as compared to the subject's expected brain function based on the subject's chronological age;

wherein the selected features are created by:
generating, using the physiological measures and from the demographic data, segmented training-data that specifies a plurality of epochs of time, and data for the subject in each epoch;
generating, using the segmented training-data, sleep-structure features for the subject; and
selecting a subset of the sleep-structure features the selected features.

16. The system of claim 15, the physiological measures of the subject were recorded at least partly while the subject is asleep and provided with at least one stimuli of the group consisting of audio stimuli, light stimuli, vibratory, electrical stimuli, open-loop stimuli, and closed-loop stimuli; and
the physiological measures comprising timing info defining timing of stimuli provided to the subject.

17. The system of claim 15, wherein generating, using the physiological measures and from the demographic data, segmented training-data comprises:
applying band-pass filters to at least some of the physiological measures comprising at least two EEG signals and at least one PPG signal;
combining at least two of the EEG signals to create a virtual EEG signal;
extracting heartbeat times from the at least one PPG signal by detecting peaks in the at least one PPG signal;
segmenting the physiological measures into a plurality of epochs of time;
generating, for each epoch of time, at least one of the group consisting of multiple time-domain features, frequency domain features, and nonlinear or complex signal descriptives; and
accessing tagging data that tags each epoch of time with a sleep stage from the group consisting of wakefulness, rapid eye movement (REM) sleep, non-REM sleep stage 1 (N1), non-REM sleep stage 2 (N2), non-REM sleep stage 3 (N3), and non-REM sleep stage 4 (N4).

18. The system of claim 15, wherein generating, using the segmented training-data, sleep-structure features for the subject comprises:
determining macrostructure features for the subject describing at least one of the group consisting of sleep-stage duration, sleep-stage percentage, sleep-stage transition probability, sleep fragmentation, and awakenings;
determining microstructure features for the subject describing at least one of the group consisting of stage-specific EEG features, waveform-specific EEG features, and stimulus-response EEG features;
determining cardiac features for the subject using at least one of the group consisting of i) heartbeat times and ii) tagging data that tags epochs of time in the segmented training-data with sleep stage; and
determining respiratory features for the subject describing at least one of the group consisting of blood oxygenation, and sleep apnea, using at least one of the group consisting of blood oxygen saturation (SpO2) and the tagging data.

19. The system of claim 15, wherein selecting a subset of the sleep-structure features as selected features comprises:
transforming at least one of a plurality of features selected from the group consisting of macrostructure features, microstructure features, cardiac features, and respiratory features; and
aggregating sleep-structure features from multiple sleep-sessions.

* * * * *